US007691973B2

(12) United States Patent
de Sauvage et al.

(10) Patent No.: US 7,691,973 B2
(45) Date of Patent: Apr. 6, 2010

(54) GFRα3 POLYPEPTIDES

(75) Inventors: Frederic J. de Sauvage, Foster City, CA (US); Robert D. Klein, Palo Alto, CA (US); Heidi S. Phillips, San Carlos, CA (US); Arnon Rosenthal, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 654 days.

(21) Appl. No.: 11/529,680

(22) Filed: Sep. 27, 2006

(65) Prior Publication Data

US 2007/0232535 A1 Oct. 4, 2007

Related U.S. Application Data

(60) Continuation of application No. 11/448,387, filed on Jun. 6, 2006, which is a division of application No. 10/621,855, filed on Jul. 16, 2003, now abandoned, which is a division of application No. 09/272,835, filed on Mar. 19, 1999, now Pat. No. 7,026,138.

(60) Provisional application No. 60/079,124, filed on Mar. 23, 1998, provisional application No. 60/081,569, filed on Apr. 13, 1998.

(51) Int. Cl.
*C07K 14/71* (2006.01)

(52) U.S. Cl. ...................................... 530/350; 530/402

(58) Field of Classification Search ....................... None
See application file for complete search history.

(56) References Cited

U.S. PATENT DOCUMENTS

| | | | | |
|---|---|---|---|---|
| 5,709,858 A | 1/1998 | Godowski et al. | ........ | 424/143.1 |
| 6,677,135 B1 | 1/2004 | Sanicola-Nadel et al. | .. | 435/69.1 |

FOREIGN PATENT DOCUMENTS

| | | |
|---|---|---|
| EP | 307247 | 3/1989 |
| EP | 846764 | 6/1998 |
| WO | WO 93/06116 | 4/1993 |
| WO | WO 97/33912 | 9/1997 |
| WO | WO 97/44356 | 11/1997 |
| WO | WO 98/53069 | 11/1998 |
| WO | WO 98/54213 | 12/1998 |

OTHER PUBLICATIONS

*Arenas et al., "GDNF Prevents Degeneration and Promotes the Phenotype of Brain Noradrenergic Neurons in Vivo" *Neuron* 15:1465-1473 (1995).
*Baloh et al., "Artemin, A Novel Member of the GDNF Ligand Family, Supports Peripheral and Central Neurons and Signals through the GFRa3-RET Receptor Complex", *Neuron* 21(6):1291-1302 (Dec. 1998).
*Beck et al., "Mesencephalic Dopaminergic Neurons Protected by GDNF from Axotomy-Induced Degeneration in the Adult Brain" *Nature* 373:339-341 (1995).
*Berkemeier et al., "Neurotrophin-5: A Novel Neurotrophic Factor That Activates trk and trkB" *Neuron* 7:857-866 (Nov. 1991).
*Bolivar et al., "Construction and Characterization of New Cloning Vehicles. II. A Multipurpose Cloning System" *Gene* 2:95-113 (1977).
*Buj-Bello et al., "GDNF is an Age-Specific Survival Factor for Sensory and Autonomic Neuron" *Neuron* 15:821-828 (1995).
*Cash et al., "Parkinson's Disease and Dementia: Norepinephrine and Dopamine in Locus Ceruleus" *Neurology* 37:42-46 (1987).
*Chan-Palay et al., "Alterations in Catecholamine Neurons of the Locus Coeruleus in Senile Dementia of the Alzheimer Type and in Parkinson's Disease with and Without Dementia and Depression" *The Journal of Comparative Neurology* 287:373-392 (1989).
*Durbec et al., "GDNF Signalling Through the Ret Receptor Tyrosine Kinase" *Naature* 381:789-793 (1996).
*Hefti, F., "Nerve Growth Factor Promotes Survival of Septal Cholingergic Neurons After Fimbrial Transections" *J. of Neuroscience* 6(8):2155-2162 (Aug. 1986).
*Henderson et al., "GDNF: A Potent Survival Factor for Motoneurons Present in Peripheral Nerve and Muscle" *Science* 266:1062-1064 (1994).
*Heumann, R., "Regulation of the Synthesis of Nerve Growth Factor" *J. Exp. Biol.* 132:133-150 (1987).
*Hirano, A., "Cytopathology of Amyotrophic Lateral Sclerosis" *Advances in Neurology: Amyotrophic Lateral Sclerosis and Other Motor Neuron Diseases*, Lewis P. Rowland, Raven Press, Ltd., Chapter 8, vol. 56:91-101 (1991).
*Hirsch et al., "Melanized dopaminergic neurons are differentially susceptible to degeneration in Parkinson's disease" *Nature* 334:345-348 (1988).
*Holmes et al., "Structure and Functional Expression of a Human Interleukin-8 Receptor" *Science* 253 (5025):1278-1280 (Sep. 13, 1991).
*Hornykiewicz, O., "Neurochemical Pathology and the Etiology of Parkinson's Disease: Basic Facts and Hypothetical Possibilities" *Mt. Sinai J. Med.* 55:11-20 (1988).
*Jing et al., "GDNF-Induced Activation of the Ret Protein Tyrosine Kinase Is Mediated by GDNFR-∀, a Novel Receptor for GDNF" *Cell* 85:1113-1124 (1996).
*Kaisho et al., "Cloning and expression of a cDNA encoding a novel human neurotrophic factor" *FEBS Letters* 266 (1,2):187-191 (Jun. 1990).
*Kearns et al., "GDNF protects nigral dopamine neurons against 6-hydroxydopamine in vivo" *Brain Research* 672:104-111 (1995).
*Kotzbauer et al., "Neurturin, a relative of glial-cell-line-derived neurotrophic factor" *Nature* 384:467-470 (1996).
*Leibrock et al., "Molecular Cloning and Expression of Brain-derived Neurotrophic Factor" *Nature* 341:149-152 (Sep. 14, 1989).

(Continued)

*Primary Examiner*—Robert C Hayes
(74) *Attorney, Agent, or Firm*—Jennifer L. Elliott; James A. Fox; Ginger R. Dreger

(57) ABSTRACT

The present invention relates to nucleotide sequences, including expressed sequence tags (ESTs), oligonucleotide probes, polypeptides, vectors and host cells expressing, and immunoadhesions and antibodies to mammalian GFRα3, a novel α-subunit receptor of the GDNF (i.e. GFR) receptor family. It further relates to an assay for measuring activation of an α-subunit receptor by detecting tyrosine kinase receptor activation (i.e., autophosphorylation) or other activities related to ligand-induced α-subunit receptor homo-dimerization or homo-oligomerization.

11 Claims, 16 Drawing Sheets

OTHER PUBLICATIONS

*Lin et al., "GDNF: A Glial Cell Line-Derived Neurotrophic Factor for Midbrain Dopaminergic Neurons" *Science* 260:1130-1132 (1993).
*Maisonpierre et al., "Neurotrophin-3: A Neurotrophic Factor Related to NGF and BDNF" *Science* 247:1446-1451 (Mar. 23, 1990).
*Marcyniuk et al., "The Topography of Cell Loss from Locus Caeruleus in Alzheimer's Disease" *J. Neurol. Sci.* 76:335-345 (1986).
*Melton et al., "Efficient in vitro synthesis of biologically active RNA and RNA hybridization probes from plasmids containing a bacteriophage SP6 promoter" *Nucleic Acids Research* 12 (18):7035-7056 (Sep. 25, 1984).
*Moore et al., "Renal and neuronal abnormalities in mice lacking GDNF" *Nature* 382:76-79 (1996).
*Oppenheim et al., "Developing motor neurons rescued from programmed and axotomy-induced cell death by GDNF" *Nature* 373:344-346 (1995).
*Phillips et al., "Widespread expression of BDNF but not NT3 by target areas of basal forebrain cholinergic neurons" *Science* 250 (4978):290-294 (Oct. 12, 1990).
*Pichel et al., "Defects in enteric innervation and kidney development in mice lacking GDNF" *Nature* 382:73-76 (1996).
*Rosenthal et al., "Primary Structure and Biological Activity of a Novel Human Neurotrophic Factor" *Neuron* 4:767-773 (May 1990).
*Ruppert et al., "Cloning and Expression of Human $TAF_{II}250$: a TBP-associated Factor Implicated in cell-cycle Regulation" *Nature* 362:175-179 (1993).
*Sanchez et al., "Renal agenesis and the absence of enteric neurons in mice lacking GDNF" *Nature* 382:70-73 (1996).
*Sompayrac et al., "Efficient infection of monkey cells with DNA of simian virus 40" *Proc. Natl. Acad. Sci. USA* 78 (12):7575-7578 (Dec. 1981).
*Stromberg et al., "Glial Cell Line-Derived Neurotrophic Factor is Expressed in the Developing but Not Adult Striatum and Stimulates Developing Dopamine Neurons In Vivo" *Exp. Neurol.* 124:401-412 (1993).
*Thimmappaya et al., "Adenovirus VAI RNA is required for efficient translation viral mRNAs at late times after infection" *Cell* 31 (3 Pat 2):543-551 (Dec. 1982).
*Thoenen et al., "Physiology of Nerve Growth Factor" *Physiological Reviews* 60 (4):1284-1335 (Oct. 1980).
*Tomac et al., "Protection and repair of the nigrostriatal dopaminergic system by GDNF in vivo" *Nature* 373:335-339 (1995).
*Treanor et al., "Characterization of a multicomponent receptor for GDNF" *Nature* 382:80-83 (1996).
*Trupp et al., "Functional receptor for GDNF encoded by the c-ret proto-oncogene" *Nature* 381:785-789 (1996).
*Yan et al., "In vivo neurotrophic effects of GDNF on neonatal and adult facial motor neurons" *Nature* 373:341-344 (1995).
*Classen-Welsh, L., "Signal Transduction by the PDGF Receptors", Progress in Growth Factor Research— 5:37-54 (1994).
*Kammer, W., et al., "Homodimerization of Interleukin-4 Receptor a Chain Can Induce Intracellular Signalling", The Journal of Biological Chemistry—271(39):23634-23637 (1996).
*Nakamura, N., et al., "An Epideraml Growth Factor Receptor/Jak2 Tyrosine Kinase Domain Chimera Induces Tyrosine Phosphorylation of Stat5 and Transduces α Growth Signal in Hematopoietic Cells", The Journal of Biological Chemistry—271(32):19483-19488 (1996).
*Nishino, J., et al., "GFRα3, A Component of the Artemin Receptor, is Required for Migration and Survival of the Superior Cervical Ganglion", Neuron-23:725-736 (1999).
*Rudinger, J., "Peptide Hormones", (ed. J.A. Parsons) University Park Press, Baltimore, pp. 1-7 (1976).
*Andres et al., Development 128(10):3685-3695 (2001) . . . Multiple Effects of Artemin On Sympathetic Neurone Generation, Survival and Growth.
*Esteva, "Monocional Antibodies, Small Molecules, and Vaccines in the Treatment of Breast Cancer," The Oncologist 9 (Suppl 3):4-9 (2004), p. 6, col. 1, lines 8-16).
*Negro et al., Recent Prog Horm Res. 59:1-12 (2004). Essential roles of Her2/erbB2 in Cardiac Development and Function.
*Rosická et al., Physiological Research 51-435-441 (2002) Gherlin-A New Endogenous Growht Hormone Secretogogue.
*Smith et al., Best Pract Res Clin Endocrinol Metab. 18(3):333-347 (2004) Growth Hormone Secretogogues: Prospects and Potential Pitfalls.
*Thilenius et al., Eur. J. Immunol. 27(5):1108-1114 (1997) Aagonist Antibody and Fas Ligand Mediate Different Sensitivity to Death in the Signaling Pathways of Fas and Cytoplasmic mutants.

```
  1 GAATTTGGCC CTCGAGGCCA AGAATTCGGC ACGAGGCGCG GCGCCCAGCG CAGGCAGAGC GCTGTCGCAT CCCGGGCGTC CACCCGCCAT GGGGCTCTCC
    CTTAAACCGG GAGCTCCGGT TCTTAAGCCG TGCTCCGCGC CGCGGGTCGC GTCCGTCTCG CGACAGCGTA GGGCCCGCAG GTGGGCGGTA CCCCGAGAGG
  1                                                                                                 Me tGlyLeuSer

101 TGGAGCCCGC GACCTCCACT GCTGATGATC CTGCTACTGG TGCTGTCGTT GTGGCTGCCA CTTGGAGCAG GAAACTCCCT TGCCACAGAG AACAGGTTTG
    ACCTCGGGCG CTGGAGGTGA CGACTACTAG GACGATGACC ACGACAGCAA CACCGACGGT GAACCTCGTC CTTTGAGGGA ACGGTGTCTC TTGTCCAAAC
  5 TrpSerProA rgProProLe uLeuMetIle LeuLeuLeuV alLeuSerLe uTrpLeuPro LeuGlyAlaG lyAsnSerLe uAlaThrGlu AsnArgPheVal

201 TGAACAGCTG TACCCAGGCC AGAAAGAAAT GCGAGGCTAA TCCCGCTTGC AAGGCTGCCT ACCAGCACCT GGGCTCCTGC ACCTCCAGTT TAAGCAGGCC
    ACTTGTCGAC ATGGGTCCGG TCTTTCTTTA CGCTCCGATT AGGGCGAACG TTCCGACGGA TGGTCGTGGA CCCGAGGACG TGGAGGTCAA ATTCGTCCGG
 39   AsnSerCy sThrGlnAla ArgLysLysC ysGluAlaAs nProAlaCys LysAlaAlaT yrGlnHisLe uGlySerCys ThrSerSerL euSerArgPro

301 GCTGCCCTTA GAGGAGTCTG CCATGTCTGC AGACTGCCTA GAGGCAGCAG AACAACTCAG GAACAGCTCT CTGATAGACT GCAGGTGCCA TCGGCGCATG
    CGACGGGAAT CTCCTCAGAC GGTACAGACG TCTGACGGAT CTCCGTCGTC TTGTTGAGTC CTTGTCGAGA GACTATCTGA CGTCCACGGT AGCCGCGTAC
 72  LeuProLeu GluGluSerA laMetSerAl aAspCysLeu GluAlaAlaG luGlnLeuAr gAsnSerSer LeuIleAspC ysArgCysHi sArgArgMet

401 AAGCACCAAG CTACCTGTCT GGACATTTAT TGGACCGTTC ACCCTGCCCG AAGCCTTGGT GACTACGAGT TGGATGTCTC ACCCTATGAA GACACAGTGA
    TTCGTGGTTC GATGGACAGA CCTGTAAATA ACCTGGCAAG TGGGACGGGC TTCGGAACCA CTGATGCTCA ACCTACAGAG TGGGATACTT CTGTGTCACT
105 LysHisGlnA laThrCysLe uAspIleTyr TrpThrValH isProAlaAr gSerLeuGly AspTyrGluL euAspValSe rProTyrGlu AspThrValThr

501 CCAGCAAACC CTGGAAAATG AATCTTAGCA AGTTGAACAT GCTCAAACCA GACTCGGACC TCTGCCTCAA ATTTGCTATG CTGTGTACTC TTCACGACAA
    GGTCGTTTGG GACCTTTTAC TTAGAATCGT TCAACTTGTA CGAGTTTGGT CTGAGCCTGG AGACGGAGTT TAAACGATAC GACACATGAG AAGTGCTGTT
139   SerLysPr oTrpLysMet AsnLeuSerL ysLeuAsnMe tLeuLysPro AspSerAspL euCysLeuLy sPheAlaMet LeuCysThrL euHisAspLys

601 GTGTGACCGC CTGCGCAAGG CCTACGGGGA GGCATGCTCA GGGATCCGCT GCCAGCGCCA CCTCTGCCTA GCCCAGCTGC GCTCCTTCTT TGAGAAGGCA
    CACACTGGCG GACGCGTTCC GGATGCCCCT CCGTACGAGT CCCTAGGCGA CGGTCGCGGT GGAGACGGAT CGGGTCGACG CGAGGAAGAA ACTCTTCCGT
172  CysAspArg LeuArgLysA laTyrGlyGl uAlaCysSer GlyIleArgC ysGlnArgHi sLeuCysLeu AlaGlnLeuA rgSerPhePh eGluLysAla

701 GCAGAGTCCC ACGCTCAGGG TCTGCTGCTG TGTCCCTGTG CACCAGAAGA TGCGGGCTGT GGGGAGCGGC GGCGTAACAC CATCGCCCCC AGTTGCGCCC
    CGTCTCAGGG TGCGAGTCCC AGACGACGAC ACAGGGACAC GTGGTCTTCT ACGCCCGACA CCCCTCGCCG CCGCATTGTG GTAGCGGGGG TCAACGCGGG
205 AlaGluSerH isAlaGlnGl yLeuLeuLeu CysProCysA laProGluAs pAlaGlyCys GlyGluArgA rgArgAsnTh rIleAlaPro SerCysAlaLeu

801 TGCCTTCTGT AACCCCCAAT TGCCTGGATC TGCGGAGCTT CTGCCGTGCG GACCCTTTGT GCAGATCACG CCTGATGGAC TTCCAGACCC ACTGTCATCC
    ACGGAAGACA TTGGGGGTTA ACGGACCTAG ACGCCTCGAA GACGGCACGC CTGGGAAACA CGTCTAGTGC GGACTACCTG AAGGTCTGGG TGACAGTAGG
239   ProSerVa lThrProAsn CysLeuAspL euArgSerPh eCysArgAla AspProLeuC ysArgSerAr gLeuMetAsp PheGlnThrH isCysHisPro

901 TATGGACATC CTTGGGACTT GTGCAACTGA GCAGTCCAGA TGTCTGCGGG CATACCTGGG GCTGATTGGG ACTGCCATGA CCCCAAACTT CATCAGCAAG
    ATACCTGTAG GAACCCTGAA CACGTTGACT CGTCAGGTCT ACAGACGCCC GTATGGACCC CGACTAACCC TGACGGTACT GGGGTTTGAA GTAGTCGTTC
272  MetAspIle LeuGlyThrC ysAlaThrGl uGlnSerArg CysLeuArgA laTyrLeuGl yLeuIleGly ThrAlaMetT hrProAsnPh eIleSerLys
```

FIG. 1A

```
1001 GTCAACACTA CTGTTGCCTT AAGCTGCACC TGCCGAGGCA GCGGCAACCT ACAGGACGAG TGTGAACAGC TGGAAAGGTC CTTCTCCCAG AACCCCTGCC
     CAGTTGTGAT GACAACGGAA TTCGACGTGG ACGGCTCCGT CGCCGTTGGA TGTCCTGCTC ACACTTGTCG ACCTTTCCAG GAAGAGGGTC TTGGGGACGG
 305 ValAsnThrT hrValAlaLe uSerCysThr CysArgGlyS erGlyAsnLe uGlnAspGlu CysGluGlnL euGluArgSe rPheSerGln AsnProCysLeu

1101 TCGTGGAGGC CATTGCAGCT AAGATGCGTT TCCACAGACA GCTCTTCTCC CAGGACTGGG CAGACTCTAC TTTTTCAGTG GTGCAGCAGC AGAACAGCAA
     AGCACCTCCG GTAACGTCGA TTCTACGCAA AGGTGTCTGT CGAGAAGAGG GTCCTGACCC GTCTGAGATG AAAAAGTCAC CACGTCGTCG TCTTGTCGTT
 339   ValGluAl aIleAlaAla LysMetArgP heHisArgGl nLeuPheSer GlnAspTrpA laAspSerTh rPheSerVal ValGlnGlnG lnAsnSerAsn

1201 CCCTGCTCTG AGACTGCAGC CCAGGCTACC CATTCTTTCT TTCTCCATCC TTCCCTTGAT TCTGCTGCAG ACCCTCTGGT AGCTGGGCTT CCTCAGGGTC
     GGGACGAGAC TCTGACGTCG GGTCCGATGG GTAAGAAAGA AAGAGGTAGG AAGGGAACTA AGACGACGTC TGGGAGACCA TCGACCCGAA GGAGTCCCAG
 372  ProAlaLeu ArgLeuGlnP roArgLeuPr oIleLeuSer PheSerIleL euProLeuIl eLeuLeuGln ThrLeuTrp

1301 CTTTGTCCTC TCCACCACAC CCAGACTGAT TTGCAGCCTG TGGTGGGAGA GAACTCGCCA GCCTGTGGAA GAAGACGCAG CGTGCTACAC AGCAACCCGG
     GAAACAGGAG AGGTGGTGTG GGTCTGACTA AACGTCGGAC ACCACCCTCT CTTGAGCGGT CGGACACCTT CTTCTGCGTC GCACGATGTG TCGTTGGGCC

1401 AACCAACCAG GCATTCCGCA GCACATCCCG TCTGCTCCAG AAGAGGTCTT AGAAGTGAGG GCTGTGACCC TTCCGATCCT GAGCGGCTAG TTTTCAAACC
     TTGGTTGGTC CGTAAGGCGT CGTGTAGGGC AGACGAGGTC TTCTCCAGAA TCTTCACTCC CGACACTGGG AAGGCTAGGA CTCGCCGATC AAAAGTTTGG

1501 TCCCTTGCCC CTGCTTCCTT CTGGCTCAGG CTGCTCCTCC TTAGGACTTT GTGGGTCCAG TTTTGCCTTC TGTTCTGATG GTGATTAGCG GCTCACCTCC
     AGGGAACGGG GACGAAGGAA GACCGAGTCC GACGAGGAGG AATCCTGAAA CACCCAGGTC AAAACGGAAG ACAAGACTAC CACTAATCGC CGAGTGGAGG

1601 AGCGCTTCTT CCTGTTTCCC AGGACCACCC AGAGGCTAAG GAATCAGTCA TTCCCTGTTG CCTTCTCCAG GAAGGCAGGC TAAGGGTTCT GAGGTGACTG
     TCGCGAAGAA GGACAAAGGG TCCTGGTGGG TCTCCGATTC CTTAGTCAGT AAGGGACAAC GGAAGAGGTC CTTCCGTCCG ATTCCCAAGA CTCCACTGAC

1701 AGAAAAATGT TTCCTTTGTG TGGAAGGCTG GTGCTCCAGC CTCCACGTCC CTCTGAATGG AAGATAAAAA CCTGCTGGTG TCTTGACTGC TCTGCCAGGC
     TCTTTTTACA AAGGAAACAC ACCTTCCGAC CACGAGGTCG GAGGTGCAGG GAGACTTACC TTCTATTTTT GGACGACCAC AGAACTGACG AGACGGTCCG

1801 AATCCTGAAC ATTTGGGCAT GAAGAGCTAA AGTCTTTGGG TCTTGTTTAA CTCCTATTAC TGTCCCCAAA TTCCCCTAGT CCCTTGGGTC ATGATTAAAC
     TTAGGACTTG TAAACCCGTA CTTCTCGATT TCAGAAACCC AGAACAAATT GAGGATAATG ACAGGGGTTT AAGGGGATCA GGGAACCCAG TACTAATTTG

1901 ATTTGACTT AAAAAAAAAA AAAAAAAAAA AAAAA
     TAAAACTGAA TTTTTTTTTT TTTTTTTTTT TTTTT
```

FIG. 1B

```
hGFRa3    1  MVRPL NPRPL PPVVLML LLL LPPSPLPLAAGDPLPTE SRLMNSCLQARRK
mGFRa3    1  ..MGL SWSPRPPLLMI LLLVLSLW.LPLGAGNSLATENRFVNSCTQARKK

hGFRa3   51  CQADPTCSAAYHHLDSCTSSISTPLPSEEPSVPADCLEAAQLRNSSLIG
mGFRa3   48  CEANPACKAAYQHLGSCTSSLSRPLPLEESAMSADCLEAAEQLRNSSLID

hGFRa3  101  CMCHRRMKNQVACLDIYWTVHRARSLGNYELDVSPYEDTVTSKPWKMNLS
mGFRa3   98  CRCHRRMKHQATCLDIYWTVHPARSLGDYELDVSPYEDTVTSKPWKMNLS

hGFRa3  151  KLNMLKPDSDLCLKFAMLCTLNDKCDRLRKAYGEACSGPHCQRHVCLRQL
mGFRa3  148  KLNMLKPDSDLCLKFAMLCTLHDKCDRLRKAYGEACSGIRCQRHLCLAQL

hGFRa3  201  LTFFEKAAEPHAQGLLLCPCAPNDRGCGERRRNTIAPNCALPPVAPNCLE
mGFRa3  198  RSFFEKAAESHAQGLLLCPCAPEDAGCGERRRNTIAPSCALPSVTPNCLD

hGFRa3  251  LRIRLCFSDPLCRSRLVDFQTHCHPMDILGTCATEQSRCLRAYLGLIGTAM
mGFRa3  248  LRISFCRADPLCRSRLMDFQTHCHPMDILGTCATEQSRCLRAYLGLIGTAM

hGFRa3  301  TPNFVSNVNTSVALSCTCRGSGNLQEECEMLEGFFSHNPCLTEAIAAKMR
mGFRa3  298  TPNFISKVNTTVALSCTCRGSGNLQDECEQLERSFSQNPCLVEAIAAKMR

hGFRa3  351  FHSQLFSQDWPHPTFAVMAHQNENPAVRPQPWVPSLFSCTLPLILLSLW
mGFRa3  348  FHRQLFSQDWADSTFSVVQQQNSNPALRLQPRLPILSFSILPLILLQTLW
```

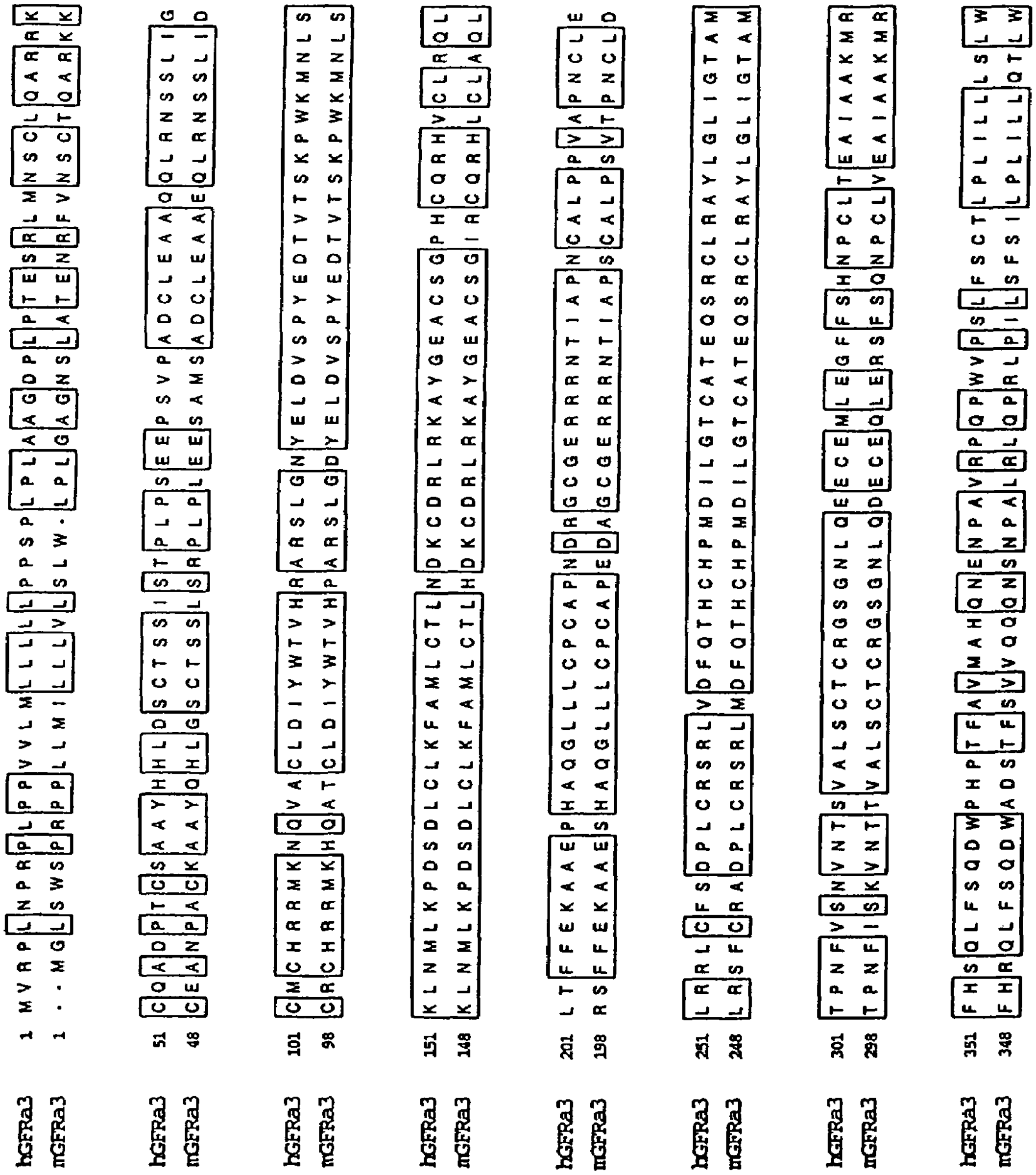

FIG. 3

```
48613    1  MVRPLNPRPLPPVVLMLLLLLPPSPLPLAAGDPLPTESRLMNSCLQARRK
48614    1  MVRPLNPRPLPPVVLMLLLLLPPSPLPLAAGDPLPTESRLMNSCLQARRK

48613   51  CQADPTCSAAYHHLDSCTSSISTPLPSEEPSVPADCLEAAQQLRNSSLIG
48614   51  CQADPTCSAAYHHLDSCTSSISTPLPSEEPSVPADCLEAAQQLRNSSLIG

48613  101  CMCHRRMKNQVACLDIYWTVHRARSLGNYELDVSPYEDTVTSKPWKMNLS
48614  101  CMCHRRMKNQVACLDIYWTVHRARSL........................

48613  151  KLNMLKPDSDLCLKFAMLCTLNDKCDRLRKAYGEACSGPHCQRHVCLRQL
48614  127  .......DSDLCLKFAMLCTLNDKCDRLRKAYGEACSGPHCQRHVCLRQL

48613  201  LTFFEKAAEPHAQGLLLCPCAPNDRGCGERRRNTIAPNCALPPVAPNCLE
48614  170  LTFFEKAAEPHAQGLLLCPCAPNDRGCGERRRNTIAPNCALPPVAPNCLE

48613  251  LRRLCFSDPLCRSRLVDFQTHCHPMDILGTCATEQSRCLRAYLGLIGTAM
48614  220  LRRLCFSDPLCRSRLVDFQTHCHPMDILGTCATEQSRCLRAYLGLIGTAM

48613  301  TPNFVSNVNTSVALSCTCRGSGNLQEECEMLEGFFSHNPCLTEAIAAKMR
48614  270  TPNFVSNVNTSVALSCTCRGSGNLQEECEMLEGFFSHNPCLTEAIAAKMR

48613  351  FHSQLFSQDWPHPTFAVMAHQNENPAVRPQPWVPSLFSCTLPLILLLSLW
48614  320  FHSQLFSQDWPHPTFAVMAHQNENPAVRPQPWVPSLFSCTLPLILLLSLW
```

FIG. 4

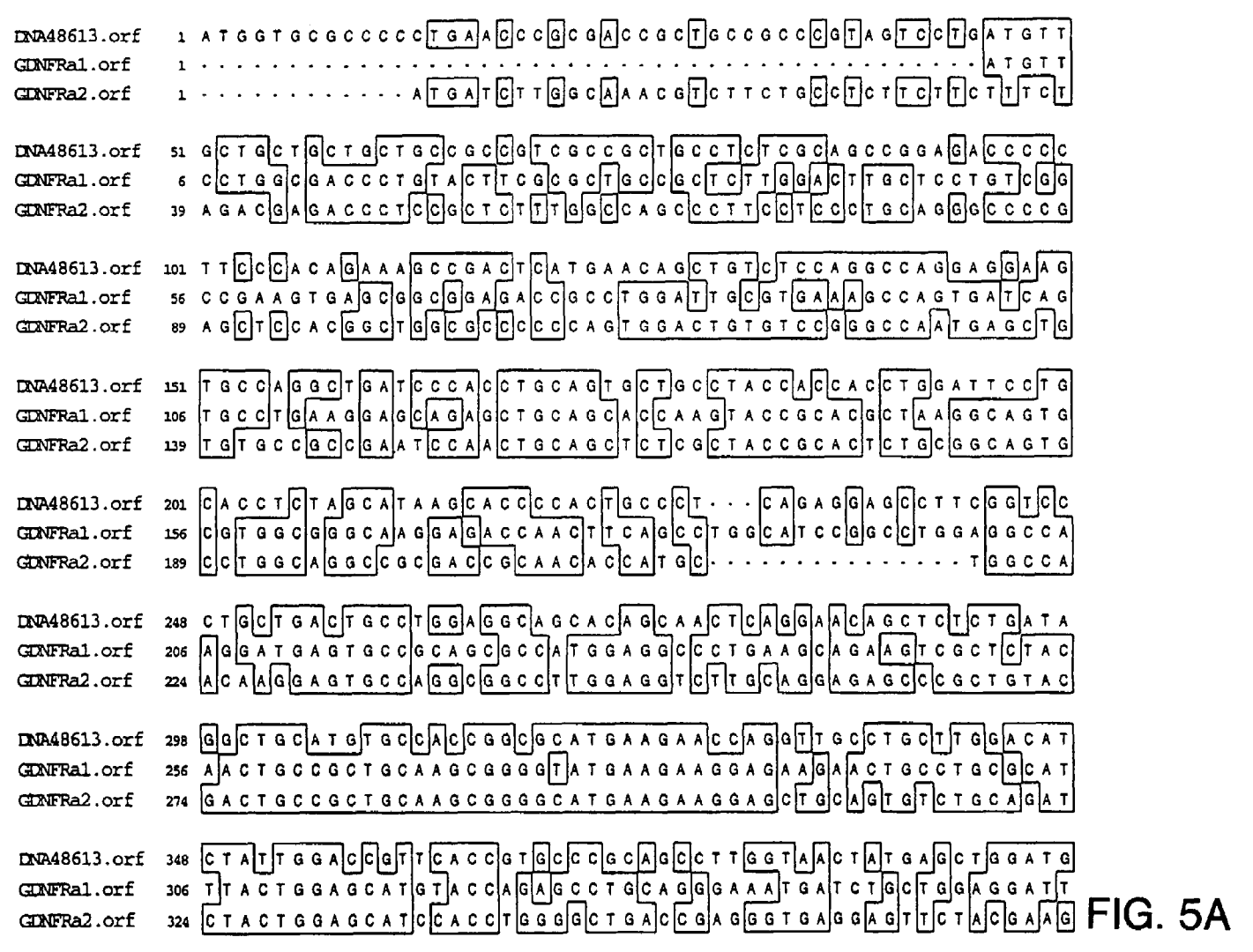

```
DNA48613.orf    1 ATGGTGCGCCCCCTGAACCCGCGACCGCTGCCGCCCGTAGTCCTGATGTT
GDNFRa1.orf     1 .............................................ATGTT
GDNFRa2.orf     1 ............ATGATCTTGGCAAACGTCTTCTGCCTCTTCTTCTTTCT

DNA48613.orf   51 GCTGCTGCTGCTGCCGCCGTCGCCGCTGCCTCTCGCAGCCGGAGACCCCC
GDNFRa1.orf     6 CCTGGCGACCCTGTACTTCGCGCTGCCGCTCTTGGACTTGCTCCTGTCGG
GDNFRa2.orf    39 AGACGAGACCCTCCGCTCTTTGGCCAGCCCTTCCTCCCTGCAGGGCCCCG

DNA48613.orf  101 TTCCCACAGAAAGCCGACTCATGAACAGCTGTCTCCAGGCCAGGAGGAAG
GDNFRa1.orf    56 CCGAAGTGAGCGGCGGAGACCGCCTGGATTGCGTGAAAGCCAGTGATCAG
GDNFRa2.orf    89 AGCTCCACGGCTGGCGCCCCCCAGTGGACTGTGTCCGGGCCAATGAGCTG

DNA48613.orf  151 TGCCAGGCTGATCCCACCTGCAGTGCTGCCTACCACCACCTGGATTCCTG
GDNFRa1.orf   106 TGCCTGAAGGAGCAGAGCTGCAGCACCAAGTACCGCACGCTAAGGCAGTG
GDNFRa2.orf   139 TGTGCCGCCGAATCCAACTGCAGCTCTCGCTACCGCACTCTGCGGCAGTG

DNA48613.orf  201 CACCTCTAGCATAAGCACCCCACTGCCCCT...CAGAGGAGCCTTCGGTCC
GDNFRa1.orf   156 CGTGGCGGGCAAGGAGACCAACTTCAGCCTGGCATCCGGCCTGGAGGCCA
GDNFRa2.orf   189 CCTGGCAGGCCGCGACCGCAACACCATGC...............TGGCCA

DNA48613.orf  248 CTGCTGACTGCCTGGAGGCAGCACAGCAACTCAGGAACAGCTCTCTGATA
GDNFRa1.orf   206 AGGATGAGTGCCGCAGCGCCATGGAGGCCCTGAAGCAGAAGTCGCTCTAC
GDNFRa2.orf   224 ACAAGGAGTGCCAGGCGGCCTTGGAGGTCTTGCAGGAGAGCCCGCTGTAC

DNA48613.orf  298 GGCTGCATGTGCCACCGGCGCATGAAGAACCAGGTTGCCTGCTTGGACAT
GDNFRa1.orf   256 AACTGCCGCTGCAAGCGGGGTATGAAGAAGGAGAAGAACTGCCTGCGCAT
GDNFRa2.orf   274 GACTGCCGCTGCAAGCGGGGCATGAAGAAGGAGCTGCAGTGTCTGCAGAT

DNA48613.orf  348 CTATTGGACCGTTCACCGTGCCCGCAGCCTTGGTAACTATGAGCTGGATG
GDNFRa1.orf   306 TTACTGGAGCATGTACCAGAGCCTGCAGGGAAATGATCTGCTGGAGGATT
GDNFRa2.orf   324 CTACTGGAGCATCCACCTGGGGCTGACCGAGGGTGAGGAGTTCTACGAAG
```

FIG. 5A

```
DNA48613.orf 398 TCTCCCCCTATGAAG---------------------ACACAGTGACCAGC
GDNFRa1.orf  356 CCCCATATGAACCAGTTA------------------ACAGCAGATTGTCA
GDNFRa2.orf  374 CCTCCCCCTATGAGCCGGTGACCTCCCGCCTCTCGGACATCTTCAGGCTT

DNA48613.orf 427 AAACCCTGGAAAATGAATCTCAGCAAACTGAACATGCTCAAACCAGACTC
GDNFRa1.orf  388 GATATATTCCGGGTGGTCCCATTCATATCAGTGGAGCACATTCCCAAAGG
GDNFRa2.orf  424 GCTTCAATCTTCTCAGGGACAGGGGCAGACCCGGTGGTCAGCGCCAAGAG

DNA48613.orf 477 AGACCTCTGCCTCAAGTTTGCCATGCTGTGTACTCTCAATGACAAGTGTG
GDNFRa1.orf  438 GAACAACTGCCTGGATGCAGCGAAGGCCTGCAACCTCGACGACATTTGCA
GDNFRa2.orf  474 CAACCATTGCCTGGATGCTGCCAAGGCCTGCAACCTGAATGACAACTGCA

DNA48613.orf 527 ACCGGCTGCGCAAGGCCTACGGGGAGGCGTGCTCCGGGCCCCACTG---C
GDNFRa1.orf  488 AGAAGTACAGGTCGGCGTACATCACCCCGTGCACCACCAGCGTGTC---C
GDNFRa2.orf  524 AGAAGCTGCGCTCCTCCTACATCTCCATCTGCAACCGCGAGATCTCGCCC

DNA48613.orf 574 CAGCGCCACGTCTGCCTCAGGCAGCTGCTCACTTTCTTCGAGAAGGCCGC
GDNFRa1.orf  535 AATGATGTCTGCAACCGCCGCAAGTGCCACAAGGCCCTCCGGCAGTTCTT
GDNFRa2.orf  574 ACCGAGCGCTGCAACCGCCGCAAGTGCCACAAGGCCCTGCGCCAGTTCTT

DNA48613.orf 624 CGAG------CCCCACGCGCAGGGCCTGCTACTGTGCCCATGTGCCCCCA
GDNFRa1.orf  585 TGACAAGGTCCCGGCCAAGCACAGCTACGGAATGCTCTTCTGCTCCTGCC
GDNFRa2.orf  624 CGACCGGGTGCCCAGCGAGTACACCTACCGCATGCTCTTCTGCTCCTGCC

DNA48613.orf 668 ACGACCGGGGCTGCGGGGAGCGCCGGCGCAACACCATCGCCCCCAACTGC
GDNFRa1.orf  635 GGGACATCGCCTGCACAGAGCGGAGGCGACAGACCATCGTGCCTGTGTGC
GDNFRa2.orf  674 AAGACCAGGCGTGCGCTGAGCGCCGCCGGCAAACCATCCTGCCCAGCTGC
```

FIG. 5B

```
DNA48613.orf  718  GCGCTGCC...GCCTGTGGCCCCCAACTGCCTGGAGCTGCGGCGCCTCTG
GDNFRa1.orf   685  TCCTATGAAGAGAGGGAGAAGCCCAACTGTTTGAATTTGCAGGACTCCTG
GDNFRa2.orf   724  TCCTATGAGGACAAGGAGAAGCCCAACTGCCTGGACCTGCGTGGCGTGTG

DNA48613.orf  765  CTTCTCCGACCCGCTTTGCAGATCACGCCTGGTGGATTTCCAGACCCACT
GDNFRa1.orf   735  CAAGACGAATTACATCTGCAGATCTCGCCTTGCGGATTTTTTTACCAACT
GDNFRa2.orf   774  CCGGACTGACCACCTGTGTCGGTCCCGGCTGGCCGACTTCCATGCCAATT

DNA48613.orf  815  GCCATCCCATGGACATCCTAGGAACTTGTGCAACAGAGCAGTCCAGA...
GDNFRa1.orf   785  GCCAGCCAGAGTCAAGGTCTGTCAGCAGCTGTCTAAAGGAAAACTACGCT
GDNFRa2.orf   824  GTCGAGCCTCCTACCAGACGGTCACCAGCTGCCCTGCGGACAATTACCAG

DNA48613.orf  862  ...TGTCTACGAGCATACCTGGGGCTGATTGGGACTGCCATGACCCCCAA
GDNFRa1.orf   835  GACTGCCTCCTCGCCTACTCGGGGCTTATTGGCACAGTCATGACCCCCAA
GDNFRa2.orf   874  GCGTGTCTGGGCTCTTATGCTGGCATGATTGGGTTTGACATGACACCTAA

DNA48613.orf  909  CTTTGTCAGCAATGTCA------ACACCAGTGTTGCCTTAAGCTGCACCT
GDNFRa1.orf   885  CTACATAGACTCCAGTA------GCCTCAGTGTGGCCCCATGGTGTGACT
GDNFRa2.orf   924  CTATGTGGACTCCAGCCCCACTGGCATCGTGGTGTCCCCCTGGTGCAGCT

DNA48613.orf  953  GCCGAGGCAGTGGCAACCTGCAGGAGGAGTGTGAAATGCTGGAAGGGTTC
GDNFRa1.orf   929  GCAGCAACAGTGGGAACGACCTAGAAGAGTGCTTGAAATTCTTGAATTTC
GDNFRa2.orf   974  GTCGTGGCAGCGGGAACATGGAGGAGGAGTGTGAGAAGTTCCTCAGGGAC

DNA48613.orf 1003  TTCTCCCACAACCCCTGCCTCACGGAGGCCATTGCAGCTAAGATGCGTTT
GDNFRa1.orf   979  TTCAAGGACAATACATGTCTTAAAAATGCAATTCAAGCCTTTGGCAATGG
GDNFRa2.orf  1024  TTCACCGAGAACCCATGCCTCCGGAACGCCATCCAGGCCTTTGGCAACGG
```

FIG. 5C

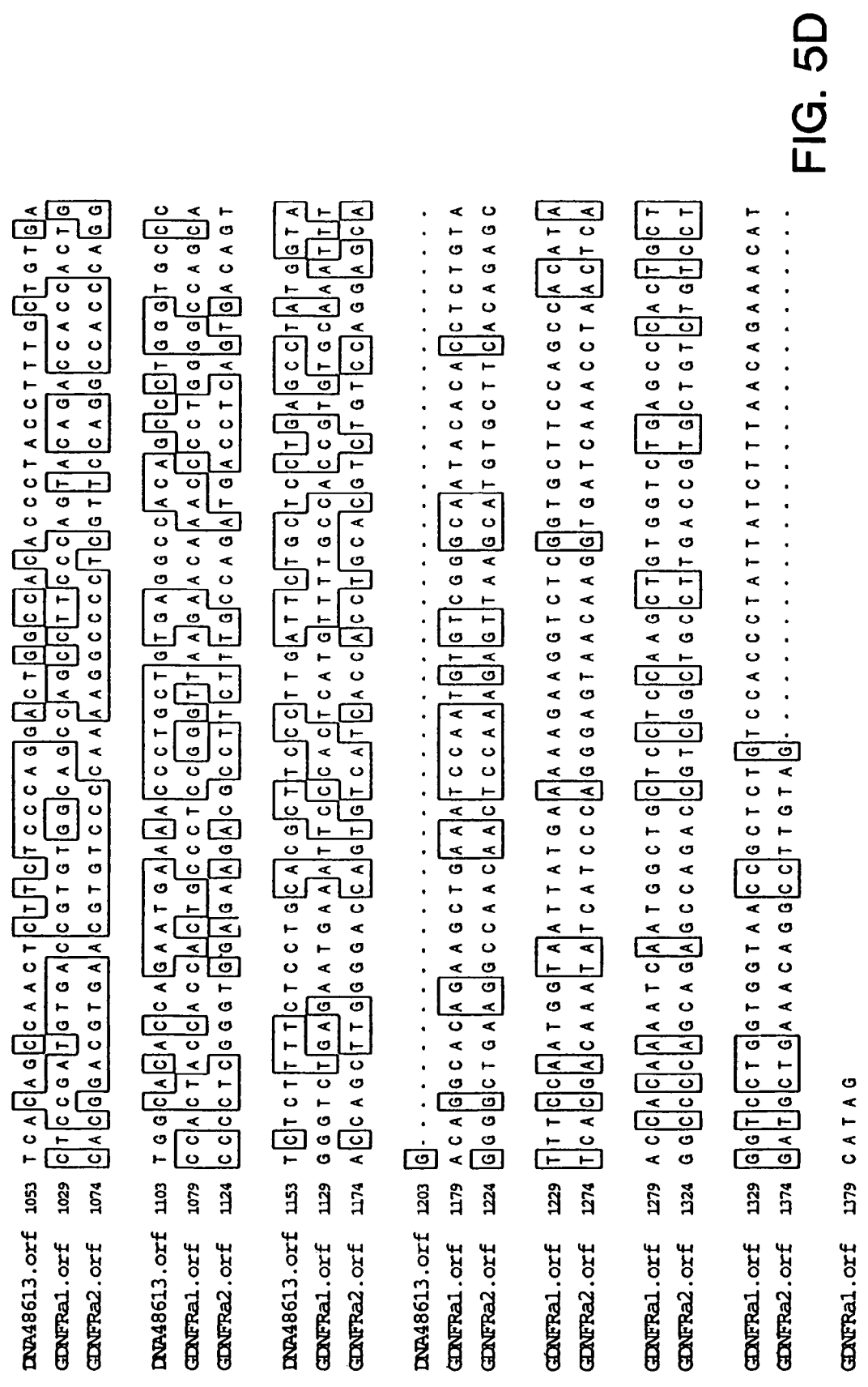

```
DNA48613.orf  1053 TCACAGCCAACTCTTCTCCCAGGACTGGCCACACCCTACCTTTGCTGTGA
GDNFRa1.orf   1029 CTCCGATGTGACCGTGTGGCAGCCAGCCTTCCCAGTACAGACCACCACTG
GDNFRa2.orf   1074 CACGGACGTGAACGTGTCCCCAAAAGGCCCCTCGTTCCAGGCCACCCAGG

DNA48613.orf  1103 TGGCACACCAGAATGAAAACCCTGCTGTGAGGCCACAGCCCTGGGTGCCC
GDNFRa1.orf   1079 CCACTACCACCACTGCCCTCCGGGTTAAGAACAAACCCCTGGGGCCAGCA
GDNFRa2.orf   1124 CCCCTCGGGTGGAGAAGACGCCTTCTTTGCCAGATGACCTCAGTGACAGT

DNA48613.orf  1153 TCTCTTTTCTCCTGCACGCTTCCCTTGATTCTGCTCCTGAGCCTATGGTA
GDNFRa1.orf   1129 GGGTCTGAGAATGAAATTCCCACTCATGTTTTGCCACCGTGTGCAAATTT
GDNFRa2.orf   1174 ACCAGCTTGGGGACCAGTGTCATCACCACCTGCACGTCTGTCCAGGAGCA

DNA48613.orf  1203 G.................................................
GDNFRa1.orf   1179 ACAGGCACAGAAGCTGAAATCCAATGTGTCGGGCAATACACACCTCTGTA
GDNFRa2.orf   1224 GGGGCTGAAGGCCAACAACTCCAAAGAGTTAAGCATGTGCTTCACAGAGC

GDNFRa1.orf   1229 TTTCCAATGGTAATTATGAAAAAGAAGGTCTCGGTGCTTCCAGCCACATA
GDNFRa2.orf   1274 TCACGACAAATATCATCCCAGGGAGTAACAAGGTGATCAAACCTAACTCA

GDNFRa1.orf   1279 ACCACAAAATCAATGGCTGCTCCTCCAAGCTGTGGTCTGAGCCCACTGCT
GDNFRa2.orf   1324 GGCCCCAGCAGAGCCAGACCGTCGGCTGCCTTGACCGTGCTGTCTGTCCT

GDNFRa1.orf   1329 GGTCCTGGTGGTAACCGCTCTGTCCACCCTATTATCTTTAACAGAAACAT
GDNFRa2.orf   1374 GATGCTGAAACAGGCCTTGTAG............................

GDNFRa1.orf   1379 CATAG
```

FIG. 5D

```
DNA48613    1   M V R P L N P R P L P P V V L M L L L L L P P S P L P L A A G D P L P T E S R L M N S C L Q A R R K
GDNFRa1     1   M F L A T . . . L Y F A L . . P L L D L L L S A . . E V S G G D . . . . . R L . . D C V K A S D Q
GDNFRa2     1   M I L A N V F C L F F F L D E T L R S L A S P S . . S L Q G P E L H G W R P P V . . D C V R A N E L

DNA48613   51   C Q A D P T C S A A Y H H L D S C T S S I S T P L P . S E E P S V P A D C L E A A Q Q L R N S S L I
GDNFRa1     36  C L K E Q S C S T K Y R T L R Q C V A G K E T N F S L A S G L E A K D E C R S A M E A L K Q K S L Y
GDNFRa2     47  C A A E S N C S S R Y R T L R Q C L A G R D R N . . . . . T M L A N K E C Q A A L E V L Q E S P L Y

DNA48613  100   G C M C H R R M K N Q V A C L D I Y W T V H R A R S L G N Y E L D V S P Y E D T V T S K P W K M N L
GDNFRa1     86  N C R C K R G M K K E K N C L R I Y W S M Y Q S L . Q G N D L L E D S P Y E P V N S R L S D I F R V
GDNFRa2     92  D C R C K R G M K K E L Q C L Q I Y W S I H L G L T E G E E F Y E A S P Y E P V T S R L S D I F R L

DNA48613  150   S K L . . . . . . . N M L K P D S D L C L K F A M L C T L N D K C D R L R K A Y G E A C S . . . . .
GDNFRa1    135  V P F I S . . . V E H I . . P K G N N C L D A A K A C N L D D I C K K Y R S A Y I T P C T T S V S .
GDNFRa2    142  A S I F S G T G A D P V V S A K S N H C L D A A K A C N L D N C K K L R S S Y I S I C N R E I S P

DNA48613  188   G P H C Q R H V C L R Q L L T F F E K A A E P H A Q G L L L C P C A P N D R G C G E R R R N T I A P
GDNFRa1    179  N D V C N R R K C H K A L R Q F F D K V P A K H S Y G M L F C S C . . R D I A C T E R R R Q T I V P
GDNFRa2    192  T E R C N R R K C H K A L R Q F F D R V P S E Y T Y R M L F C S C . . Q D Q A C A E R R R Q T I L P

DNA48613  238   N C A L P P V A . P N C L E L R R L C F S D P L C R S R L V D F Q T H C H P . M D I L G T C A T E Q
GDNFRa1    227  V C S Y E E R E K P N C L N L Q D S C K T N Y I C R S R L A D F F T N C Q P E S R S V S S C L K E N
GDNFRa2    240  S C S Y E D K E K P N C L D L R G V C R T D H L C R S R L A D F H A N C R A S Y Q T V T S C P A D N

DNA48613  286   . S R C L R A Y L G L I G T A M T P N F V S N V . . N T S V A L S C T C R G S G N L Q E E C E M L E
GDNFRa1    277  Y A D C L L A Y S G L I G T V M T P N Y I D S S . . S L S V A P W C D C S N S G N D L E E C L K F L
GDNFRa2    290  Y Q A C L G S Y A G M I G F D M T P N Y V D S S P T G I V V S P W C S C R G S G N M E E E C E K F L

DNA48613  333   G F F S H N P C L T E A I A A . . . . . . . . . . . . . . . . . . . . . . K M R F H S Q L F S
GDNFRa1    325  N F F K D N T C L K N A I Q A F G N G S D V T V W Q P A F P V Q T T T A T T T T A L R V K N K P L G
GDNFRa2    340  R D F T E N P C L R N A I Q A F G N G T D V N V S P K G P S F Q A T Q A P R V E K T P S L P D D L S

DNA48613  358   Q . . . . . . . . . D W P H P T F A V M A H Q N E N P A V R P Q . . . . . . . . . . . . . . . . . .
GDNFRa1    375  P A G S E N E I P T H V L P P C A N L Q A Q K L K S N V S G N T H L C I S N G N Y E K E G L G A S S
GDNFRa2    390  D S T S . . . L G T S V I T T C T S V Q E Q G L K A N N S K E L S M C F T . . E L T T N I I P G S N

DNA48613  381   . . . . P W V P S L F S C T L P L I L L S L W . . . . . . . . . . . . . .
GDNFRa1    425  H I T T K S M A A P P S C G L S P L L V L V V T A L S T L L S L T E T S
GDNFRa2    435  K V I K P N S G P S R A R P S A A L T V L S V L M L K Q A L . . . . . .
```

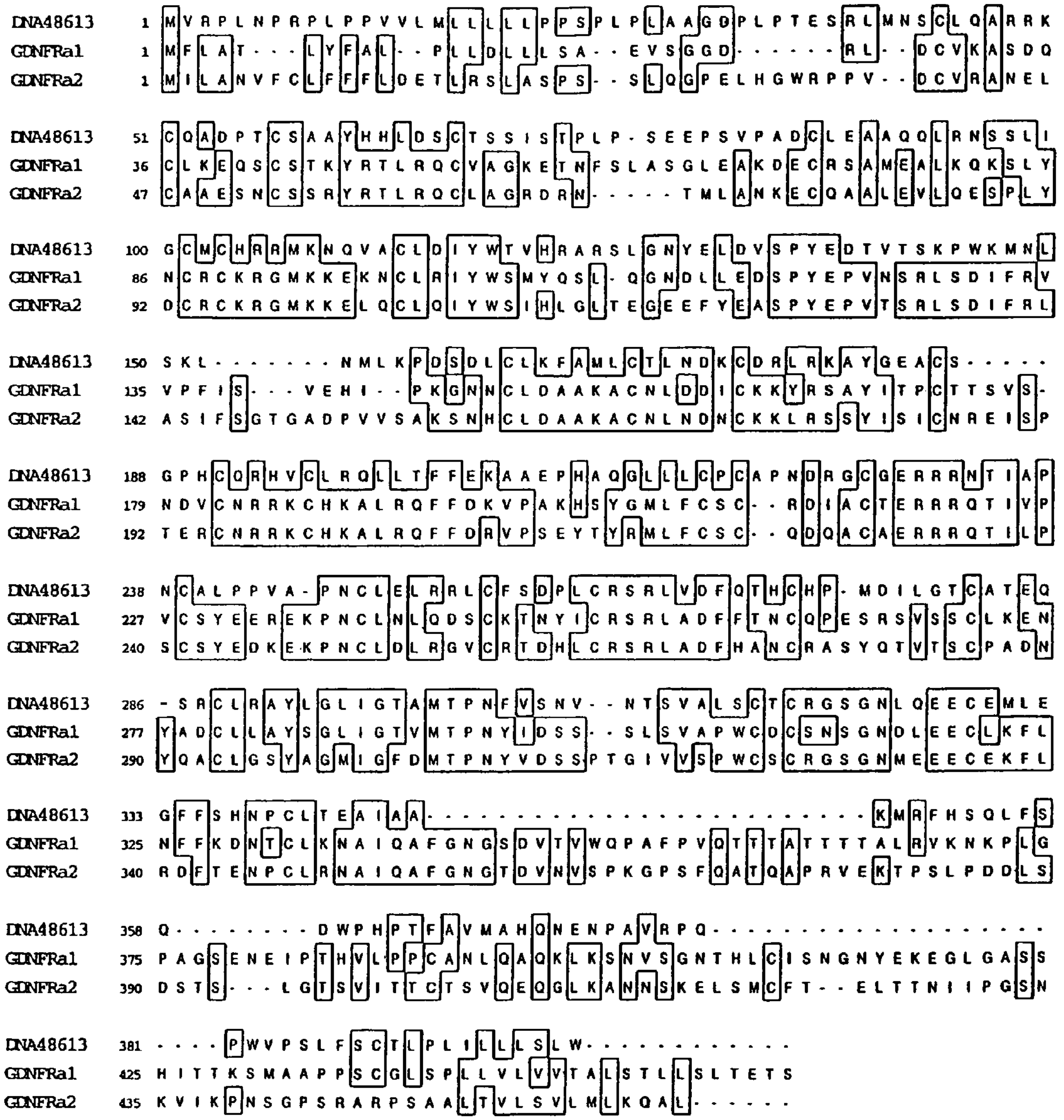

FIG. 6

| | ug/ml | 3C8 | 5B6 | 2272 |
|---|---|---|---|---|
| a | 1 | 1.409 | 1.211 | 1.463 |
| b | 0.4 | 1.791 | 1.600 | 1.511 |
| c | 0.16 | 1.684 | 1.267 | 0.915 |
| d | 0.064 | 1.017 | 0.749 | 0.562 |
| e | 0.0256 | 0.589 | 0.490 | 0.439 |
| f | 0.01024 | 0.427 | 0.406 | 0.371 |
| g | 0.004096 | 0.370 | 0.392 | 0.363 |
| h | 0 | 0.357 | 0.369 | 0.372 |

GFRα3 POLYPEPTIDES

CROSS-REFERENCE TO RELATED APPLICATIONS

This application is a continuation application of U.S. patent application Ser. No. 11/448,387, filed Jun. 6, 2006, which is a divisional application of U.S. patent application Ser. No. 10/621,855, filed Jul. 16, 2003, now abandoned, which is a divisional application of U.S. patent application Ser. No. 09/272,835 filed Mar. 19, 1999, now U.S. Pat. No. 7,026,138, from which priority is claimed under 35 U.S.C. 120, and which claims the benefit under 35 U.S.C. 119(e) of Provisional Applications Ser. No. 60/079,124, filed Mar. 23, 1998, and Ser. No. 60/081,569, filed Apr. 13, 1998, the entire contents of all of which provisional and non-provisional applications are hereby incorporated by reference.

TECHNICAL FIELD

The present invention relates generally to the identification and isolation of novel DNA and to the recombinant production of novel polypeptides which are characterized by the presence of GFRα3 sequences, an α-subunit receptor. It further relates to an assay for measuring ligand-induced activation of an α-subunit receptor by detecting autophosphorylation of a kinase domain of an α-receptor-receptor protein tyrosine kinase (rPTK) fusion using a kinase receptor activation, enzyme-linked immunosorbent assay (KIRA ELISA) or by other means to detect α-subunit homodimerization.

INTRODUCTION

BACKGROUND

Neurotrophic factors such as insulin-like growth factors, nerve growth factors, brain-derived neurotrophic factor, neurotrophin-3, -4/5 and -6, ciliary neurotrophic factor, GDNF, and neurturin have been proposed as potential means for enhancing specific neuronal cell survival, for example, as a treatment for neurodegenerative diseases such as amylotrophic lateral sclerosis, Alzheimer's disease, stroke, epilepsy, Huntington's disease, Parkinson's disease, and peripheral neuropathy. It would be desirable to provide additional therapy for this purpose. Protein neurotrophic factors, or neurotrophins, which influence growth and development of the vertebrate system, are believed to play an important role in promoting the differentiation, survival, and function of diverse groups of neurons in the brain and periphery. Neurotrophic factors are believed to have important signaling functions in neural tissues, based in part upon the precedent established with nerve growth factor (NGF). NGF supports the survival of sympathetic, sensory, and basal forebrain neurons both in vitro and in vivo. Administration of exogenous NGF rescues neurons from cell death during development. Conversely, removal or sequestration of endogenous NGF by administration of anti-NGF antibodies promotes such cell death (Heumann, *J. Exp. Biol.*, 132:133-150 (1987); Hefti, *J. Neurosci.* 6:2155-2162 (1986); Thoenen, et al., *Physiol. Rev.* 60: 1284-1335 (1980)).

Additional neurotrophic factors related to NGF have since been identified. These include brain-derived neurotrophic factor (BDNF)(Leibrock, et al., *Nature*, 341:149-152 (1989)); neurotrophin-3 (NT-3)(Kaisho, et al., *FEBS Lett.*, 266:187 (1990); Maisonpierre, et al., *Science*, 247:1446 (1990); Rosenthal, et al., *Neuron*, 4:767 (1990), and neurotrophin 4/5 (NT-4/5)(Berkemeier, et al., *Neuron*, 7:857-866 (1991)).

Neurotrophins, similar to other polypeptide growth factors, affect their target cells through interactions with cell surface receptors. According to current understanding, two kinds of transmembrane glycoproteins act as receptors for the known neurotrophins. Equilibrium binding studies have shown that neurotrophin-responsive neuronal cells possess a common low molecular weight (65,000-80,000 Daltons), a low affinity receptor typically referred to as $p75^{LNGFR}$ or p75, and a high molecular weight (130,000-150,000 Dalton) receptor. The high affinity receptors are members of the trk family of receptor tyrosine kinases.

Receptor tyrosine kinases are known to serve as receptors for a variety of protein factors that promote cellular proliferation, differentiation, and survival. In addition to the trk receptors, examples of other receptor tyrosine kinases include the receptors for epidermal growth factor (EGF), fibroblast growth factor (FGF), and platelet-derived growth factor (PDGF). Typically, these receptors span the cell membrane, with one portion of the receptor being intracellular and in contact with the cytoplasm, and another portion of the receptor being extracellular. Binding of a ligand to the extracellular portion of the receptor induces tyrosine kinase activity in the intracellular portion of the receptor, with ensuing phosphorylation of various intracellular proteins involved in cellular signaling pathways.

Glial cell line-derived neurotrophic factor ("GDNF") and Neurturin ("NTN") are two, recently identified, structurally related, potent survival factors for sympathetic sensory and central nervous system neurons (Lin et al. *Science* 260:1130-1132 (1993); Henderson et al. *Science* 266:1062-1064 (1994); Buj-Bello et al., *Neuron* 15:821-828 (1995); Kotzbauer et al. *Nature* 384:467-470 (1996)). Recently, GDNF was shown to mediate its actions through a multi-component receptor system composed of a ligand binding glycosyl-phosphatidyl inositol (GPI) linked protein (designated GDNFRα; also designated GFR-α-1) and the transmembrane receptor tyrosine kinase Ret (Treanor et al. *Nature* 382:80-83 (1996); Jing et al. *Cell* 85:1113-1124 (1996); Trupp et al. *Nature* 381:785-789 (1996); Durbec et al. *Nature* 381:789-793 (1996)). The NTN signal is transmitted via GFRα2, which is also Ret associated.

Membrane-bound proteins and receptors can play an important role in the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interaction. The membrane-bound proteins can also be employed for screening of potential peptide or small molecule inhibitors of the relevant receptor/ligand interaction.

The aberrant expression or uncontrolled regulation of any one of these receptor tyrosine kinases can result in different malignancies and pathological disorders. Therefore, there exists a need to identify means to regulate, control and manipulate receptor tyrosine kinases ("RTK"), their ligands, or their α-subunit receptor molecules, e.g., GPI-linked α-subunit receptors, to which they associate, in order to provide new and additional means for the diagnosis and therapy of receptor tyrosine kinase pathway-related disorders and cellular processes. The present application provides the clinician and researcher with such means by providing new molecules that are specific for interacting with certain receptor genes and their gene products. These compounds and their methods of use, as provided herein, allow exquisite therapeutic control and specificity. Accordingly, it is one object of the present invention to provide an improved therapy for the prevention and/or treatment of neurological conditions and other conditions in which certain neurotrophic signaling pathways play a role.

SUMMARY

Applicants have identified a family of cDNAs that encode a novel human polypeptide or its homologs, designated in the present application as "GFRα3." The GFRα3 is an α-subunit receptor, a receptor that complexes with a beta subunit receptor in response to ligand binding. A-subunits provide the ligand binding component and the beta subunit provides the catalytic signal transduction activity, such as tyrosine kinase activity. GFRα receptor family members complex with a beta subunit receptor referred to as Ret. This hetero-complex results in signal transduction. The present invention is based in part on the novel finding that the α-subunit can dimerize upon binding ligand, and further the dimerization can activate a kinase activity of a kinase catalytic domain fused to the ligand-binding domain of the α-subunit receptor.

In one embodiment, the invention provides an isolated nucleic acid molecule having at least about 65% sequence identity to (a) a nucleic acid sequence encoding a GFRα3 polypeptide comprising the sequence of amino acids 27 to 400 of SEQ ID NO: 15, amino acids 27 to 369 of SEQ ID NO: 17 or amino acids 27 to 374 of SEQ ID NO: 5 or (b) the complement of the nucleic acid molecules of (a). In another embodiment, the nucleic molecule sequence above comprises a ligand-binding domain of a GFRα3 polypeptide of amino acids 84 to 360 of SEQ ID NO: 15, amino acids 84 to 329 of SEQ ID NO: 17, or the sequence of amino acids 110 to 386 of SEQ ID NO: 20, or their complementary nucleic acids. The isolated nucleic acid comprises a GFRα3 encoding sequence which preferably hybridizes under stringent conditions to nucleic acid sequences encoding a GFRα3 polypeptide of the invention. The sequence identity preferably is at least about 75%, more preferably at least 85%, even more preferably at least 90%, most preferably at least 95%. In one aspect, the encoded polypeptide has at least about 75%, preferably at least 80%, more preferably at least 85%, even more preferably at least 90%, and most preferably at least about 95% sequence identity with a polypeptide having amino acid residues 27 to 400 of SEQ ID NO: 15, amino acids 27 to 369 of SEQ ID NO: 17, amino acids 27 to 374 of SEQ ID NO: 5, a ligand-binding domain of a GFRα3 polypeptide of amino acids 84 to 360 of SEQ ID NO: 15, amino acids 84 to 329 of SEQ ID NO: 17, or the sequence of amino acids 110 to 386 of SEQ ID NO: 20. Preferably the identity is to amino acid residues 27 to 400 of SEQ ID NO: 15 and DNA encoding it.

In a further embodiment, the isolated nucleic acid molecule comprises DNA encoding a GFRα3 polypeptide having amino acid residues 27 to 400 of SEQ ID NO:15, or is complementary to such encoding nucleic acid sequence, and remains stably bound to it under at least moderate, and optionally, under high stringency conditions. In another aspect, the invention provides a nucleic acid of the full length protein of clone DNA48613 (SEQ ID NO: 14), DNA48614 (SEQ ID NO: 16) or murine GFRα3 (SEQ ID NO: 4, clone 13). DNA48613-1268 (SEQ ID NO: 14) and DNA48614-1268 SEQ ID NO: 16) were deposited with the ATCC under accession numbers ATCC 209752 (Designation: DNA48613-1268) and ATCC 209751 (Designation: DNA48614-1268), respectively, on Apr. 07, 1998.

In yet another embodiment, the invention provides a vector comprising DNA encoding GFRα3 polypeptide. A host cell comprising such a vector is also provided. By way of example, the host cells may be CHO cells, *E. coli*, or yeast. A process for producing GFRα3 polypeptides is further provided and comprises culturing host cells under conditions suitable for expression of GFRα3 and recovering the same from the cell culture.

In yet another embodiment, the invention provides isolated GFRα3 polypeptide. In particular, the invention provides isolated native sequence GFRα3 polypeptide, which in one embodiment, includes an amino acid sequence comprising residues 27 to 400 SEQ ID NO:15. Native GFRα3 polypeptides with or without the native signal sequence (amino acids 1 to 26) in SEQ ID NO: 15, and with or without the initiating methionine are specifically included. In yet another embodiment is provide a polypeptide comprising a sequence of amino acid residues 27 to 400 of SEQ ID NO: 15, amino acids 27 to 369 of SEQ ID NO: 17, amino acids 27 to 374 of SEQ ID NO: 5, a ligand-binding domain of a GFRα3 polypeptide of amino acids 84 to 360 of SEQ ID NO: 15, amino acids 84 to 329 of SEQ ID NO: 17, or the sequence of amino acids 110 to 386 of SEQ ID NO: 20. Alternatively, the invention provides a GFRα3 polypeptide encoded by the nucleic acid deposited under the above accession numbers. The polypeptide optionally is lacking the hydrophobic sequence associated with GPI-anchoring.

In yet another embodiment, the invention provides chimeric molecules comprising a GFRα3 polypeptide fused to a heterologous polypeptide or amino acid sequence. An example of such a chimeric molecule comprises a GFRα3 polypeptide fused to an epitope tag sequence or an Fc region of an immunoglobulin. The chimeric molecules can comprise the ligand-binding domain of an α-subunit receptor, the intracellular catalytic domain of a tyrosine kinase receptor, and a flag epitope.

In yet another embodiment, the invention provides an antibody which specifically binds to GFRα3 polypeptide. Optionally, the antibody is a monoclonal antibody.

In view of the surprising finding herein that the α-subunit receptor can dimerize upon ligand binding, and further that such dimerization can activate a kinase domain fused the α-subunit receptor, a method is provided herein to measure ligand-induced a subunit receptor activation, i.e. homo-dimerizaiton or homo-oligomerization. In one embodiment is provided a sensitive, reliable assay that measures agonist- or ligand-induced α-subunit receptor activation, i.e., homo-dimerization or homo-oligomerization, preferably by measuring receptor protein tyrosine kinase (rPTK) autophosphorylation of a polypeptide fusion comprising the ligand binding domain of an α-subunit receptor and the intracellular catalytic domain of a receptor protein tyrosine kinase. The construct can further optionally comprise a flag epitope to facilitate trapping and detection of the activated (e.g., dimerized, phosphorylated) α-subunit receptor. The assay is desirably useful for qualitatively and quantitatively measuring α-subunit receptor activation as well as facilitating identification and characterization of potential agonists and antagonists for a selected α-subunit receptor. It is a further object of the invention to provide an assay which enables ligand-receptor interactions to be studied for any selected α-subunit receptor, and preferably a GFRα subunit receptor.

This assay must have a capacity for high throughput, that is, the ability to reliably evaluate large numbers of samples in a relatively short period of time (e.g., in one day). The assay ideally does not use radioactive materials and is also amenable to automation.

In at least one embodiment of the invention is provided a generic assay which enables a α-subunit receptor of interest to be studied, regardless of whether or not a receptor-specific capture agent having the desired characteristics is available. Furthermore, it is an object of the invention to provide an assay which substantially represents the ligand-binding activity of the α-subunit receptor in situ. This is desirable insofar as it reduces the possibility that altered interactions between the receptor and the ligand may occur as a consequence of the receptor not being membrane-bound. In one embodiment of the assay is provided a method for measuring ligand binding by detecting serine-threonine kinase phosphorylation, phosphorylation of intracellular kinases and phosphatase activity of a catalytic domain fused to the α-subunit receptor. Accordingly, the invention provides an assay for measuring activation or ligand binding of an α-subunit receptor construct chimera by detecting its homo-dimerization or homo-oligomerization by in turn measuring kinase or phosphatase activity (i.e., by autophosphorylation) of catalytic domain that is fused to the ligand-binding domain of an α-subunit receptor of interest.

The assay can be divided into two major stages, each of which is generally performed in separate assay plates. The first stage of the assay involves activating the α-subunit receptor construct, preferably in a KIRA stage of the assay. The second stage of the assay involves measuring receptor construct activation. Conveniently, this is achieved using an enzyme-linked immunosorbent assay (ELISA) to measure receptor construct activation.

The KIRA stage of the assay involves activating a α-subunit receptor-kinase receptor fusion construct which is located in the cell membrane of an eukaryotic cell such that the extracellular domain of the α-subunit receptor faces the external milieu of the cell, a transmembrane domain is located in the cell membrane and the catalytic kinase domain is located intracellularly. This stage of the overall assay involves steps (a) to (c) below:

(a) The first solid phase (e.g., a well of a first assay plate) is coated with a substantially homogeneous population of cells (usually a mammalian cell line) so that the cells adhere to the solid phase. Often, the cells are adherent and thereby adhere naturally to the first solid phase. In one embodiment of the invention, the cells have been transformed with DNA encoding a polypeptide receptor construct comprising an α-subunit receptor ligand-binding domain fused to a catalytic kinase domain, or a "receptor construct" defined further below, which DNA is expressed by the cells such that the receptor or receptor construct is suitably positioned in the cell membranes thereof.

The receptor construct further, and preferably, comprises a fusion with a flag polypeptide. The flag polypeptide is recognized by the capture agent, often a capture antibody, in the ELISA part of the assay. Use of a receptor construct as disclosed herein is particularly advantageous since it provides a "generic" assay wherein autophosphorylation of any kinase receptor domain can be measured, regardless of whether or not a receptor-specific capture agent having the required characteristics is available. Often, the receptor construct is a fusion protein comprising the ECD of a selected α-subunit receptor, the catalytic ICD (and possibly the transmembrane domain) of another well characterized tyrosine kinase (e.g., the Rse receptor).

(b) An analyte is then added to the wells having the adhering cells, such that the receptor construct is exposed to (or contacted with) the analyte. This assay enables identification of agonist and antagonist ligands for the α-subunit receptor of interest. In order to detect the presence of an antagonist ligand which blocks binding and/or activation of the receptor by an agonist ligand, the adhering cells are exposed to the suspected antagonist ligand first and then to the agonist ligand (or to a mixture of the agonist and antagonist) so that competitive inhibition of receptor binding and activation can be measured. Also, the assay can identify an antagonist which binds to the agonist ligand thereby reduces or eliminates its ability to bind to, and activate, the kinase domain. To detect such an antagonist, the suspected antagonist and the agonist for the receptor are incubated together and the adhering cells are then exposed to this mixture of ligands.

(c) Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. Thus, this assay provides a significant improvement over assays described by Knutson and Buck, supra, Klein et al., supra, and Hagino et al. supra, insofar as it is surprisingly unnecessary to concentrate the cell lysate prior to the ELISA. Furthermore, unlike the other assays, in the instant assay the cells can be lysed in lysis buffer using gentle agitation without the need for homogenizing, centrifuging or clarifying the cells. The cell lysate thus prepared is then ready to be subjected to the ELISA stage of the assay. It has been discovered that, surprisingly, the first assay plate can be stored at freezing temperatures (i.e., at about −20° to −70° C.) for significant periods of time (at least 6 months) before the ELISA stage of the assay. This is a significant finding insofar as the KIRA and ELISA stages of the assay can be performed on separate days.

The ELISA component of the assay comprises steps (d) to (h), described below.

(d) As a first step, the second solid phase (usually a well of an ELISA microtiter plate) is coated with a capture agent (often a capture antibody) which binds specifically to the receptor construct, preferably to an optionally present flag polypeptide. Coating of the second solid phase is carried out so that the capture agent adheres to the second solid phase. The capture agent is generally a monoclonal antibody, but, as is described in the examples herein, polyclonal antibodies may also be used.

(e) The cell lysate obtained in step (c) of the above-mentioned KIRA stage of the assay is exposed to, or contacted with, the adhering capture agent so that the receptor construct adheres to (or is captured in) the second solid phase. Unlike the assay of Klein et al., the instant assay does not require the ligand for the receptor as well as kinase inhibitors to be present to achieve suitable immobilization of the receptor or receptor construct to the second solid phase.

(f) A washing step is then carried out, so as to remove unbound cell lysate, leaving the captured receptor or receptor construct.

(g) The adhering or captured receptor construct is then exposed to, or contacted with, an anti-phosphotyrosine antibody which identifies phosphorylated tyrosine residues in the tyrosine kinase receptor domain. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule.

(h) Finally, binding of the anti-phosphotyrosine antibody to the captured receptor construct is measured, e.g., a color change in the color reagent.

The invention also pertains to a Rse.flag reagent which is particularly useful for use in the KIRA ELISA assay. The Rse.flag reagent is a polypeptide comprising a fusion of a flag polypeptide (usually the gD flag described herein) to the carboxyl terminus of the intracellular domain of the Rse rPTK. Generally, the transmembrane domain of Rse and the extracellular domain of another rPTK of interest are also present in the fusion polypeptide reagent. The nucleic acid encoding this reagent and a cell transformed therewith are also claimed.

In yet a further aspect, the invention relates to a kit which can be used in the KIRA ELISA disclosed above which comprises an anti-flag polypeptide capture agent (e.g. a capture antibody) which is usually bound to the second solid phase as described herein, and a receptor construct. Thus, the kit generally provides an ELISA microtiter plate having an anti-flag polypeptide capture antibody adhering to a well thereof. Optionally, the kite also provides an anti-phosphotyrosine antibody which is often labelled, or reagents for labelling the anti-phosphotyrosine antibody are supplied with the kit. Sometimes, a homogeneous population of cells which have been transformed with a receptor construct as described herein are also provided with the kit. The kit can also suitably includes instructions for carrying out the KIRA ELISA.

BRIEF DESCRIPTION OF THE DRAWINGS

FIGS. 1A-B show the nucleotide sequence (SEQ ID NO: 4) and deduced amino acid sequence (SEQ ID NO: 5) of a native sequence of murine GFRα3.

FIG. 3 shows the alignment comparison between murine (SEQ ID NO: 5) and human (SEQ ID NO: 15) GFRα3 amino acid sequences. Conserved residues are boxed.

FIG. 4 shows the alignment comparison between human GFRα3 (SEQ ID NO: 15 from DNA48613) and its splice variant (SEQ ID NO: 17 from DNA48614). Conserved sequences are boxed. The 30 amino acid deletion sequence is indicated.

FIGS. 5A-D show the nucleic acid sequence alignment of the DNA sequence (SEQ ID NO: 14) encoding human GFRα3 with DNAs encoding human GFRα1 (SEQ ID NO: 6) and human GFRα2 (SEQ ID NO: 7), respectively.

FIG. 6 shows the amino acid sequence alignment of human GFRα3 (SEQ ID NO: 15), human GFRα1 (SEQ ID NO: 6) and human GFRα2 (SEQ ID NO: 7).

DETAILED DESCRIPTION OF THE PREFERRED EMBODIMENTS

I. Definitions

Figure 2:
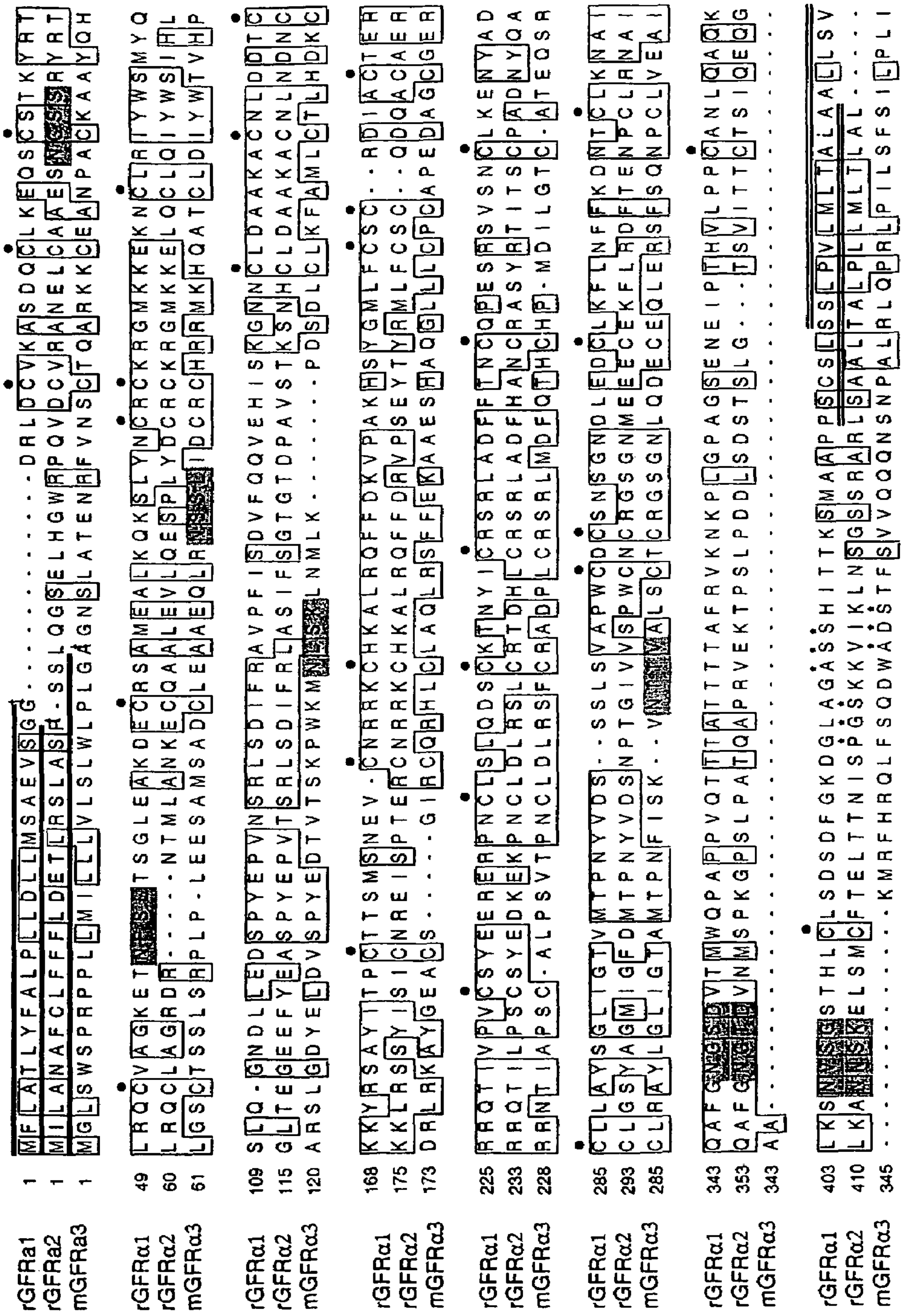
FIG. 2 shows the alignment of the amino acid sequences for murine GFRα3 (SEQ ID NO: 5), rat GFRα1 (SEQ ID NO: 8) and rat GFRα2 (SEQ ID NO: 9). The N-terminal signal peptides are indicated. The C-terminal hydrophobic sequences associated with GPI-anchoring are overlined. Asterisks indicate the amino acids for GPI-anchor attachment. Potential glycosylation sites are marked by shaded boxes. Conserved identical residues are boxed.

The terms "GFRα3" "GFRα3 polypeptide" and "GFRα3-homolog" when used herein encompass native sequence GFRα3 and GFRα3 variants (which are further defined herein). The GFRα3 may be isolated from a variety of sources, such as from human tissue types or from another source, or prepared by recombinant or synthetic methods. A "native sequence GFRα3" comprises a polypeptide having the same amino acid sequence as a GFRα3 derived from nature. Such native sequence GFRα3 can be isolated from nature or can be produced by recombinant or synthetic means. The term "native sequence GFRα3" specifically encompasses naturally-occurring truncated or secreted forms of GFRα3 (e.g., an extracellular domain sequence), naturally-occurring variant forms (e.g., alternatively spliced forms) and naturally-occurring allelic variants of GFRα3. In one embodiment of the invention, the native sequence GFRα3 is a mature or full-length native sequence GFRα3 comprising amino acids 1 to 400 of SEQ ID NO:15, with or without the N-terminal signal sequence, and with or without the initiating methionine at position 1.

"GFRα3 variant" means an active GFRα3 as defined below having at least about 75% amino acid sequence identity to (a) a DNA molecule encoding a GFRα3 polypeptide, with or without its native signal sequence, or (b) the complement of the DNA molecule of (a). In a particular embodiment, the GFRα3 variant has at least about 80% amino acid sequence homology with the GFRα3 having the deduced amino acid sequence shown in SEQ ID NO: 15 for a full-length native sequence GFRα3. Such GFRα3 variants include, for instance, GFRα3 polypeptides wherein one or more amino acid residues are added, or deleted, at the N— or C-terminus of the sequence of SEQ ID NO:15. Preferably, the nucleic acid or amino acid sequence identity is at least about 75%, more preferably at least about 80%, and even more preferably at least about 90%, and yet even more preferably at least about 95%.

"Percent (%) amino acid sequence identity" with respect to the GFRα3 sequences identified herein is defined as the percentage of amino acid residues in a candidate sequence that are identical with the amino acid residues in the GFRα3 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the GFRc sequences identified herein is defined as the percentage of nucleotides in a candidate sequence that are identical with the nucleotides in the GFRα3 sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the GFRα3 natural environment will not be present. Ordinarily, however, isolated polypeptide will be prepared by at least one purification step.

An "isolated" DNA48613 nucleic acid molecule is a nucleic acid molecule that is identified and separated from at least one contaminant nucleic acid molecule with which it is ordinarily associated in the natural source of the DNA48613 nucleic acid. An isolated DNA48613 nucleic acid molecule is other than in the form or setting in which it is found in nature. Isolated DNA48613 nucleic acid molecules therefore are distinguished from the DNA48613 nucleic acid molecule as it exists in natural cells. However, an isolated DNA48613 nucleic acid molecule includes DNA48613 nucleic acid molecules contained in cells that ordinarily express DNA48613 where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel, et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50 EC; (2) employ during hybridization a denaturing agent, such as formamide, for example, 50% (v/v) formamide with 0.1% bovine serum albumin/0.1% Ficoll/0.1% polyvinylpyrrolidone/50 mM sodiumphosphate buffer at pH 6.5 with 750 mM sodiumchloride, 75 mM sodium citrate at 42EC; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42EC, with washes at 42EC in 0.2×SSC (sodium chloride/sodium citrate) and 0.1% SDS; or (4) employ a buffer of 10% dextran sulfate, 2×SSC and 50% formamide at 55EC, followed by a high-stringency wash consisting of 0.1×SSC containing EDTA at 55EC.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37EC in a solution comprising: 20% formamide, 5×SSC (150 mM NaCl, 15 mM trisodium citrate), 50 mM sodium phosphate (pH 7.6), 5× Denhardt's solution 10% dextran sulfate, and 20 mg/mL denatured sheared salmon sperm DNA, followed by washing the filters in 1×SSC at 37-50EC. The skilled artisan will recognize how to adjust the temperature, ionic strength, etc. as necessary to accommodate factors such as probe length and the like.

"rPTK" means a receptor protein tyrosine kinase.

"ECD", "TM domain" and "ICD" refer to the extracellular domain, transmembrane domain and intracellular domain of a rPTK, respectively.

"Kinase Receptor Activation" or "KIRA" when used throughout this application refers to the first stage of the instantly claimed assay wherein a cell-bound receptor construct (typically with a rPTK ICD domain) is exposed to a potential agonist/antagonist ligand which may (or may not) induce phosphorylation of tyrosine residues in the intracellular domain of the rPTK portion of the receptor construct. The KIRA is generally carried out in the "first assay plate" as defined herein. U.S. Pat. No. 5,766,863, and its corresponding WO publication, entitled "Kinase receptor activation assay" are hereby incorporated herein in their entirety for teaching a KIRA assay using a recombinantly expressed protein fusion of a receptor extracellular domain and a substitute enzymatic domain, e.g. tyrosine kinase domain.

"Enzyme-Linked Immunosorbent Assay" or "ELISA" refers to the second stage of the instantly claimed assay and involves measuring tyrosine phosphorylation of the kinase domain of the receptor construct. The ELISA is normally carried out in the "second assay plate" as disclosed in this application. The ELISA is a "sandwich ELISA" insofar as it involves capturing the receptor construct to the second solid phase (usually the well of an ELISA microtiter plate). ELISA assays generally involve the preparation of enzyme-antibody conjugates. The conjugated enzyme cleaves a substrate to generate a colored reaction product that can be detected spectrophotometrically. In this assay, the absorbance of the colored solution in individual microtiter wells is proportional to the amount of phosphotyrosines. A review of ELISA is found in *Current Protocols in Molecular Biology*, Vol. 2, chapter 11 (1991). While the term "ELISA" is used to describe the second stage of the instant assay, it is only preferred embodiment of the invention, since, as disclosed herein, techniques other than enzymatic detection are available for measuring binding of the anti-phosphotyrosine antibody to the activated receptor.

The terms "tyrosine kinase", "tyrosine kinase receptor", "receptor protein tyrosine kinase" and "rPTK" are used interchangeably herein and refer to a protein having at least one phosphate accepting phenolic group in its ICD. The protein is usually a receptor insofar as it has a ligand-binding ECD, TM domain and ICD. The ICD usually comprises a catalytic kinase domain and has one or more phosphate accepting tyrosine residues. Examples of tyrosine kinase receptors include the insulin receptor, insulin related receptor, epidermal growth factor receptor (EGF-R), platelet-derived growth factor receptors A and B (PDGF-R-A and PDGF-R-B), insulin-like growth factor 1 receptor (IGF-1-R), macrophage colony-stimulating factor receptor (M-CSF-R), HER2/neu/c-erbB-2 receptor, HER3/c-erbB-3 receptor, Xmrk receptor, IRR receptor, fibroblast growth factor (FGF) receptors bek and flg, c-kit receptor, Flk/kDR receptor, Rse receptor, the Eph, Elk, Eck, Eek, Erk, Cek4/Mek4/HEK and Cek5 receptors, Ax1 receptor, hepatocyte growth factor receptor (HGF-R), Flt1 VEGF receptor, SAL-S1 receptor, HpTK 5 receptor, trkA receptor, trkB receptor, and trkC receptor. See, for example, Ullrich and Schlessinger *Cell* 81:203-212 (1990); Fantl et al., *Annu. Rev. Biochem.* 62:453-481 (1993); Mark et al., *Journal of Biological Chemistry* 269(14): 10720-10728 (1994); and WO 93/15201.

The terms mentioned above encompass chimeric "receptor" molecules or "receptor constructs" or "α-subunit receptor constructs" which comprise at least the extracellular domain of a selected α-subunit receptor, and the intracellular domain of a kinase receptor (preferably a rPTK), and optionally, the transmembrane domain of the same or another tyrosine kinase, and further optionally a flap epitope. Of course, the α-receptor of interest can provide the transmembrane domain if it has one. The terms also encompass amino acid sequence variants and covalent derivatives of the various α-subunit receptors and rPTKs kinase domains to which they are fused, provided they still display kinase phosphorylation activity in the KIRA ELISA. Therefore, the variants will general have conservative amino acid alterations. The individual domains of the α-subunit receptor kinase can be delineated based on sequence homology to known receptors in the relevant family and hydrophobicity plots. For example, the hydrophobic transmembrane domain can be readily determined and the ECD and ICD, when present, are usually amino-terminal and carboxyl terminal to the transmembrane domain or GPI-anchor, respectively. Conveniently, the transmembrane domain and ICD of the Rse receptor can be fused to the ECD of a α-subunit receptor of interest, typically with the GPI-anchor sequence, thereby forming a chimeric receptor which is encompassed by the terms denoting a receptor construct as mentioned herein.

In the preferred embodiment, the α-subunit receptor is selected from the group consisting of GFRα1, GFRα2, GFRα3, and GFRα4.

By "autophosphorylation" is meant activation of the catalytic kinase domain of the rPTK portion of the receptor construct, whereby at least one intrinsic tyrosine residue is phosphorylated. Generally, autophosphorylation will result when an agonist molecule binds to the extracellular domain of the α-subunit receptor. Without being limited to any particular mechanism of action, it is thought that binding of the agonist molecule results in oligomerization of the receptor construct which causes activation of the catalytic kinase domain.

By "solid phase" is meant a non-aqueous matrix to which the cells (in the KIRA stage of the assay) or the capture agent (in the ELISA stage of the assay) can adhere. Usually, the solid phase comprises the well of an assay plate but the invention is by no means limited to this embodiment. For example, the solid phase can comprise a discontinuous solid phase of discrete particles. The particles can be porous and formed from a number of different materials, e.g., polysaccharides (e.g. agarose), polyacrylamides, polystyrene, polyvinyl alcohol, silicones and glasses. For examples of suitable particulate solid phases, see U.S. Pat. No. 4,275,149.

By "well" is meant a recess or holding space in which an aqueous sample can be placed. The well is provided in an "assay plate". The invention usually employs a "first assay plate" which is formed from a material (e.g. polystyrene) which optimizes adherence of cells (having the receptor or receptor construct) thereto. Generally, the individual wells of the first assay plate will have a high surface area to volume ratio and therefore a suitable shape is a flat bottom well (where the cells are adherent). The "second assay plate" is generally formed from a material (e.g. polystyrene) which optimizes adherence of the capture agent thereto. The second assay plate may have the same general construction and/or characteristics as the first assay plate. However, separate plates are used for the KIRA stage of the assay and the ELISA stage of the assay.

In the preferred embodiment of the invention, both the first assay plate and the second assay plate are "microtiter" plates. The term "microtiter" plate when used herein refers to an assay plate having between about 30 to 200 individual wells, usually 96 wells. Often, the individual wells of the microtiter plate will hold a maximum volume of about 250 μl. Conveniently, the first assay plate is a 96 well polystyrene or plastic, cell culture microtiter plate (such as that sold by Becton Dickinson Labware, Lincoln Park, N.J.), which allows for automation. Often, about 50 μl to 300 μl, more preferably 100 μl to 200 μl, of an aqueous sample comprising cell culture media with the cells suspended therein will be added to each well of the first assay plate in the KIRA stage of the assay. It is desirable to seed between about $1\times10^4$ to $3\times10^5$ cells per well. More preferably, $5\times10^4$ to $1\times10^5$ cells per well are seeded. Usually, the second assay plate will comprise a polystyrene microtiter ELISA plate such as that sold by Nunc Maxisorp, Inter Med, Denmark.

The term "homogeneous population of cells" refers to a substantially homogeneous population of cells wherein at least about 80%, and preferably about 90%, of the cells in the population are of the same cell type. Therefore, it is convenient to use a cell line. The cell line is a eukaryotic cell line, normally an animal cell line and desirably a mammalian cell line.

The cells have, or are transformed to produce, the selected receptor construct. Accordingly, the cell is transformed with a nucleic acid encoding the receptor construct and the nucleic acid is expressed so that the ECD of the receptor faces the external milieu of the cell, the transmembrane domain is located in the cell membrane and the kinase domain is located intracellularly. As a general proposition, a minimum number of about $1\times10^4$ receptors/cell is required.

The term "adherent" when used herein to describe the cell, refers to a cell which naturally adheres to the first solid phase (often the well of the first assay plate), thereby forming a fairly uniform coating of the cells on the inside surface of the well. The uniform coating of cells generally forms following incubation of the cells in the wells of the first assay plate for about 8-16 hours. After incubation, non-adhering cells and cell culture medium are decanted off the first assay plate. Incubation is usually carried out at a temperature which is optimal for cell growth, i.e, about 37° C. Examples of adherent cell lines include CHO cells (Urlaub and Chasin, *Proc. Natl. Acad. Sci. USA* 77:4216 (1980)), MCF-7 cells (ATCC HB 22), 293 cells (Graham et al., *J. Gen Virol.* 36:59 (1977)), Swiss albino 3T3 fibroblast cell line (ATCC No. CCL 92) and U937 macrophage cell line (ATCC No. CRL 1593).

A "flag polypeptide" comprises a short polypeptide which has enough residues to provide an epitope (preferably a linear epitope) against which a "capture agent" thereagainst can be made, yet is short enough such that it does not interfere with activity of the kinase domain or the ligand-binding domain. The flag polypeptide is also sufficiently unique so that the capture agent thereagainst does not bind to other reagents in the assay. Selection of a "unique" flag polypeptide sequence can be accomplished by comparing the sequence of a proposed flag polypeptide against other known sequences in Genbank or EMBL, for example. Suitable flag polypeptides generally have at least 6 amino acid residues and usually between about 8-80 amino acid residues (preferably between about 9-30 amino acid residues).

By "receptor construct" is meant a polypeptide which comprises a fusion of an α-subunit receptor ligand-binding domain and a kinase receptor catalytic domain, and optionally a flag polypeptide as defined above. The flag polypeptide is provided at a location in the receptor construct such that: a) the flag polypeptide does not interfere with ligand binding to the receptor; b) the flag polypeptide does not interfere with autophosphorylation of the receptor and c) the flag polypeptide is presented in a suitable configuration so that it can bind to the capture agent in the ELISA stage of the assay. Often, the polypeptide flag will be present at the N-terminus of the receptor construct. Alternatively, the flag polypeptide may be present at the C-terminus of the receptor construct. An Rse.gD construct is preferred. The Rse construct disclosed herein is particularly useful, since the ICD (and optionally the transmembrane domain) thereof can be fused to the ECD of a receptor of interest, thereby obviating the need to establish where the flag polypeptide should be located with respect to the receptor of interest.

"Rse.gD" refers to a receptor construct which has the Rse receptor protein tyrosine kinase ICD domain with the Herpes Simplex virus glycoprotein D (gD) flag polypeptide fused to the COOH-terminus thereof.

"Rse.flag reagent" refers to a polypeptide which comprises the ICD of the Rse receptor fused at its COOH-terminus to a flag polypeptide (normally the gD flag polypeptide). Sometimes, the TM domain of Rse with the ECD of an α-subunit receptor of interest will also be present in the Rse.gD. reagent. "Receptor ECD/Rse.gD Chimera" refers to a fusion of the ECD of a α-subunit receptor ligand-binding domain of interest to the TM and ICD domains of Rse which are fused COOH-terminally to the gD flag polypeptide.

By "capture agent" is meant a compound or agent which is able to adhere to the second solid phase, as herein defined, and which is selective for a receptor construct. Thus, the capture agent captures the receptor construct to the wells of the second assay plate. Usually, the capture agent binds selectively to the flag polypeptide which has been fused to the receptor of interest. Binding of the capture agent is not affected by the presence or absence of ligand bound to the receptor and does not induce receptor activation upon capture. Furthermore, the capture agent does not sterically block access to the phosphorylated tyrosine(s) by the anti-phosphotyrosine antibody. Means for selecting suitable capture agents are described herein. Generally, the capture agent will comprise an antibody (e.g., an affinity purified polyclonal antibody or a monoclonal antibody), but other selective agents, such as streptavidin which binds selectively to the "strep-tag" polypeptide can also be used (see Schmidt et al., *Protein Engineering* 6(1):109-122 (1993)). Streptavidin can be purchased commercially from Zymed Laboratories, S. San Francisco, Calif., for example. Alternatively, the capture agent can comprise protein A (which binds specifically to immunoglobulins). In this embodiment of the invention, the activated receptor-construct present in the cell lysate is incubated with an antibody which binds specifically thereto, thereby forming a receptor-antibody complex. This complex can be captured by protein A by virtue of its specific binding to the antibody present in the complex. Protein A can be purchased commercially from Pharmacia Biotech, Inc., Piscataway, N.J., for example.

In the most preferred embodiment, the capture agent is a monoclonal antibody which binds specifically to a flag polypeptide (which is present in the receptor construct). Examples of suitable flag polypeptides and their respective capture antibodies include the flu HA flag and its antibody 12CA5, (Field et al., *Mol. Cell. Biol.* 8:2159-2165 (1988)); the c-myc flag and the 8F9, 3C7, 6E10, G4, B7 and 9E10 antibodies thereto (Evan et al., *Molecular and Cellular Biology* 5(12):3610-3616 (1985)); as well as the Herpes Simplex virus glycoprotein D (gD) flag and the 5B6 antibody thereto (Paborsky et al., *Protein Engineering* 3(6):547-553 (1990) and Mark et al., *Journal of Biological Chemistry* 269(14):

10720-10728 (1994)). Other flag polypeptides have been disclosed. Examples include the Flag-peptide (Hopp et al., *Bio-Technology* 6:1204-1210 (1988)); the KT3 epitope peptide (Martin et al., *Science* 255:192-194 (1992)); an α-tubulin epitope peptide (Skinner et al., *J. Biol. Chem* 266:15163-15166 (1991)); and the T7 gene 10 protein peptide tag (Lutz-Freyermuth et al., *Proc. Natl. Acad. Sci. USA* 87:6393-6397 (1990)). Once the flag polypeptide has been selected as discussed above, a capture antibody thereto can be generated using the techniques disclosed herein.

The term "analyte" refers to a compound or composition to be studied, usually to investigate its ability to activate (or prevent activation of) the α-subunit receptor of interest. The analyte can comprise a bodily fluid (such as plasma or amniotic fluid) or a composition known to contain, or suspected of containing, a ligand for the tyrosine kinase receptor. The analyte can also comprise a cell which has a ligand to the α-subunit receptor of interest.

"Ligand" when used herein refers to a molecule which is able to bind to the extracellular α-subunit receptor of interest or to a known agonist thereof. The ligand will usually be an agonist or antagonist for the receptor.

By "agonist" is meant a molecule which is able activate the intracellular kinase domain of the receptor construct upon binding to the extracellular α-subunit receptor portion. Often, the agonist will comprise a growth factor (i.e., a polypeptide that is able to stimulate cell division). Exemplary growth factors include artemin, neurturin, GDNF and persephin. Alternatively, the agonist can be an antibody against the receptor or even its flag sequence as shown here in the Examples. However, other non-protein agonists such as small organic molecules are also encompassed by the invention.

By "antagonist" is meant a molecule which blocks agonist action. Usually, the antagonist will either: (a) bind to the α-subunit receptor portion and thereby block binding and/or activation of the receptor by an agonist thereto (the antagonist may bind to the ECD of the receptor, but this is not necessarily the case) or (b) bind to the agonist and thus prevent activation of the receptor by the agonist. This assay facilitates the detection of both types of antagonist. The antagonist may, for example, comprise a peptide fragment comprising the receptor binding domain of the endogenous agonist ligand for the receptor. The antagonist may also be an antibody which is directed against the ECD of the receptor, or against a known agonist for the receptor. However, other non-protein molecules are also encompassed by this term.

The term "antibody" is used in the broadest sense, and can more specifically cover single anti-GFRα3 monoclonal antibodies (including agonist, antagonist, and neutralizing antibodies) and anti-GFRα3 antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of GFRα3, or an α-subunit receptor as the context will indicate, which retain the biologic and/or immunologic activities of native or naturally-occurring GFRα3, or receptor. A preferred activity is the ability to bind to and affect, e.g., block or otherwise modulate, an activity of an agonist or natural ligand. The activity preferably involves the regulation of neuronal function.

A "GFRα3 ligand" is a molecule which binds to and preferably activates native sequence GFRα3. The ability of a molecule to bind to GFRα3 can be determined, for example, by the ability of the putative ligand to bind to GFRα3 immunoadhesin coated on an assay plate, for example. Specificity of binding can be determined by comparing binding to GFRα1 or 2.

The term "anti-phosphotyrosine antibody" refers to a molecule, usually an antibody, which binds selectively to phosphorylated tyrosine residues in the kinase domain of a rPTK. The antibody can be polyclonal, but is desirably a monoclonal antibody. Anti-phosphotyrosine polyclonal antibodies can be made using the techniques disclosed in White and Backer, *Methods in Enzymology* 201:65-67 (1991) and monoclonal anti-phosphotyrosine antibodies can be obtained commercially from Upstate Biologicals, Inc. (UBI, Lake Placid, N.Y.), for example.

The word "label" when used herein refers to a detectable compound or composition which is conjugated directly or indirectly with a molecule (such as the anti-phosphotyrosine antibody). The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

By "washing" is meant exposing the solid phase to an aqueous solution (usually a buffer or cell culture media) in such a way that unbound material (e.g., non-adhering cells, non-adhering capture agent, unbound ligand, receptor construct, cell lysate, or anti-phosphotyrosine antibody) is removed therefrom. To reduce background noise, it is convenient to include a detergent (e.g. Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) may be required.

By "block buffer" is meant an aqueous, pH buffered solution containing at least one blocking compound which is able to bind to exposed surfaces of the second solid phase which are not coated with capture agent. The blocking compound is normally a protein such as bovine serum albumin (BSA), gelatin, casein or milk powder and does not cross-react with any of the reagents in the assay (e.g., the anti-phosphotyrosine antibodies and detection reagents). The block buffer is generally provided at a pH between about 7 to 7.5 and suitable buffering agents include phosphate and TRIS.

By "lysis buffer" is meant an aqueous, pH buffered solution comprising a solubilizing detergent, one or more protease inhibitors and at least one phosphatase inhibitor (such as sodium orthovanadate). The term "solubilizing detergent" refers to a water miscible, non-ionic detergent which lyses cell membranes of eukaryotic cells but does not denature or activate the receptor construct. Examples of suitable non-ionic detergents include Triton-X 100, Tween 20, CHAPS and Nonidet P-40 (NP40) available from Calbiochem, La Jolla, Calif., for example. Many other non-ionic detergents are available in the art. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin and benzamidine. Preservatives (e.g., thimerosal) and one or more compounds which maintain the isotonicity of the solution (e.g., sodium chloride (NaCl) or sucrose) and a buffer (e.g., Tris or PBS) are usually also present. Generally, the pH of the lysis buffer is in the range about 7 to 7.5.

Usually, following addition of the lysis buffer to the first assay plate, the first assay plate is "gently agitated" and this expression refers to the act of physically shaking the first assay plate (normally using a circular motion) at a substantially low velocity. Gentle agitation does not involve mechanically disrupting the cells (e.g. by homogenizing or centrifuging the cells). Exemplary shaking velocities are in the order of 200 to 500 rpm, preferably 300 to 400 rpm in a Bellco orbital shaker, for example.

II Compositions and Methods of the Invention

A. Full-Length GFRα3

The present invention provides newly identified and isolated nucleotide sequences encoding polypeptides referred to in the present application as GFRα3. In particular, Applicants have identified and isolated cDNA encoding a GFRα3 polypeptide, as disclosed in further detail in the Examples below. Using BLAST, BLAST-2 and FastA sequence alignment computer programs, Applicant has found that a full-length native sequence GFRα3 (SEQ ID NO:15) has 34% amino acid sequence identity with GFRα1 and GFRα2. Accordingly, it is presently believed that GFRα3 disclosed in the present application is a newly identified member of the GFR protein family and may possess neuronal cell activation function typical of the GFR protein family. However, the limited distribution of GFRα3 compared to GFRα1 and GFRα2 make it and its agonists preferred molecules for avoiding unwanted side-effects when administered.

Glial cell line-derived neurotrophic factor ("GDNF") and Neurturin ("NTN") are two structurally related, potent survival factors for sympathetic sensory and central nervous system neurons (Lin et al. *Science* 260:1130-1132 (1993); Henderson et al. *Science* 266:1062-1064 (1994); Buj-Bello et al., *Neuron* 15:821-828 (1995); Kotzbauer et al. *Nature* 384: 467-470 (1996)). GDNF was shown to mediate its actions through a multi-component receptor system composed of a ligand binding glycosyl-phosphatidyl inositol (GPI) linked protein (designated GDNFRα or GFRα1) and the transmembrane tyrosine kinase Ret (Treanor et al. *Nature* 382:80-83 (1996); Jing et al. *Cell* 85:1113-1124 (1996); Trupp et al. *Nature* 381:785-789 (1996); Durbec et al. *Nature* 381:789-793 (1996)). NTN signal is transmitted by GFRα2, which also associates with Ret. Described herein is the isolation, sequence, and tissue distribution of a GPI-linked protein and its gene, designated GFRα3, which is shown to modulate the response to a novel ligand in the NTN and GDNF family. In the case of cellular responses to NTN, cells require the presence of GFRα2. Ligand bound GFRα2 induces phosphorylation of the tyrosine kinase receptor Ret. These findings identify Ret and GFRα2, respectively, as signalling and ligand binding components of a receptor for NTN and related ligands. This defines a novel neurotrophic and differentiation factor receptor family of receptors containing a shared transmembrane protein tyrosine kinase (Ret) and a ligand specific GPI-linked protein component (GFRα).

Glial cell line-derived neurotrophic factor ("GDNF")(Lin et al., *Science,* 260:1130-1132(1993); WO 93/06116, which are incorporated herein in its entirety), is a potent survival factor for midbrain dopaminergic (Lin et al., (1993), supra; Strömberg et al., *Exp. Neurol.,* 124:401-412 (1993); Beck et al., *Nature,* 373:339-341 (1995): Kearns et al., *Brain Res.,* 672:104-111 (1995); Tomac et al., *Nature,* 373:335-339 (1995)), spinal motor (Henderson et al., *Science,* 266:1062-1064 (1994); Oppenheim et al., *Nature,* 373:344-346 (1995)); Yan et al. *Nature,* 373:341-344 (1995)), and noradrenergic neurons (Arenas et al., *Neuron,* 15:1465-1473 (1995)), which degenerate in Parkinson's disease (Hirsch et al., *Nature,* 334: 345-348 (1988): Hornykiewicz, *Mt. Sinai J. Med.,* 55:11-20 (1988)), amyotrophic lateral sclerosis (Hirano, Amyotrophic Lateral Sclerosis and Other Motor Neuron Disease, P. Rowland, ed. (New York: Raven Press, Inc.) pp. 91-101 (1991), and Alzheimer's disease (Marcyniuk et al., *J. Neurol. Sci.,* 76:335-345 (1986); Cash et al., *Neurology,* 37:42-46(1987); Chan-Palay et al., *Comp. Neurol.,* 287:373-392 (1989)), respectively. Based on mice genetically engineered to lack GDNF, additional biological roles for GDNF have been reported: the development and/or survival of enteric, sympathetic, and sensory neurons and the renal system, but not for catecholaminergic neurons in the central nervous system (CNS)(Moore et al., *Nature* 382:76-79 (1996); Pichel et al., *Nature* 382:73-76 (1996); Sanchez et al., *Nature* 382:70-73 (1996)). Despite the physiological and clinical importance of GDNF, little is known about its mechanism of action.

Cytokine receptors frequently assemble into multi-subunit complexes. Sometimes, the α subunit of this complex is involved in binding the cognate growth factor and the β-subunit may contain an ability to transduce a signal to the cell. Without wishing to be bound by theory, these receptors have been assigned to three subfamilies depending on the complexes formed. Subfamily 1 includes the receptors for EPO, granulocyte colony-stimulating factor (G-CSF), interleukin-4 (IL-4), interleukin-7 (IL-7), growth hormone (GH), and prolactin (PRL). Ligand binding to receptors belonging to this subfamily is thought to result in homodimerization of the receptor. Subfamily 2 includes receptors for IL-3, granulocyte-macrophage colony-stimulating factor (GM-CSF), interleukin-5 (IL-5), interleukin-6 (IL-6), leukemia inhibitory factor (LIF), oncostatin M (OSM), and ciliary neurotrophic factor (CNTF). Subfamily 2 receptors are heterodimers having an α-subunit for ligand binding, and β-subunit (either the shared β-subunit of the IL-3, GM-CSF, and IL-5 receptors or the gp130 subunit of the IL-6, LIF, OSM, and CNTF receptors) for signal transduction. Subfamily 3 contains only the interleukin-2 (IL-2) receptor. The β and γ subunits of the IL-2 receptor complex are cytokine-receptor polypeptides which associate with the α-subunit of the unrelated Tac antigen.

The present invention is based on the discovery of the GFRα3, a protein in the GFR family, whose natural ligand is unknown. The experiments described herein demonstrate that this molecule is a receptor which appears to play a role in mediating responses to a novel GDNF family ligand. In particular, this receptor has been found to be present in a variety of tissue and cell populations, including neurons, thus indicating that GFRα3 ligands, such as agonist antibodies, can be used to stimulate proliferation, growth, survival, differentiation, metabolism, or regeneration of GFRα3- and Ret-containing cells.

B. GFRα3 Variants

In addition to the full-length native sequence GFRα3 described herein, it is contemplated that GFRα3 variants can be prepared. GFRα3 variants can be prepared by introducing appropriate nucleotide changes into the GFRα3 DNA, or by synthesis of the desired GFRα3 polypeptides. Those skilled in the art will appreciate that amino acid changes may alter post-translational processes of the GFRα3, such as changing the number or position of glycosylation sites or altering the membrane anchoring characteristics. In fact, a splice GFRα3 splice variant is encoded by DNA48614 and a murine variant by SEQ ID NO:4. Other variants include the IgG-tagged and gD-RSE chimeras made as described in the Examples.

Variations in the native full-length sequence GFRα3 or in various domains of the GFRα3 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the GFRα3 that results in a change in the amino acid sequence of the GFRα3 as compared with the native sequence GFRα3. Optionally the variation is by substitution of at least one amino acid with any other amino acid in one or more of the domains of the GFRα3. Guidance in determining which amino acid residue may be inserted, substituted or deleted without adversely affecting the desired activity may be found by comparing the sequence of the GFRα3 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variants can be those encoded by an isolated nucleic acid molecule having at least about 65% sequence identity to (a) a nucleic acid sequence encoding a GFRα3 polypeptide comprising the sequence of amino acids 27 to 400 of SEQ ID NO: 15, amino acids 27 to 369 of SEQ ID NO: 17 or amino acids 27 to 374 of SEQ ID NO: 5 or (b) the complement of the nucleic acid molecules of (a). Further, the variants can be encoded by nucleic molecule sequences comprising a ligand-binding domain of a GFRα3 polypeptide of amino acids 84 to 360 of SEQ ID NO: 15, amino acids 84 to 329 of SEQ ID NO: 17, or the sequence of amino acids 110 to 386 of SEQ ID NO: 20, or their complementary nucleic acids. These isolated nucleic acid molecules preferably comprise a GFRα3 encoding sequence which preferably hybridizes under stringent conditions to nucleic acid sequences encoding a GFRα3 polypeptide of the invention. The sequence identity preferably is at least about 75%, more preferably at least 85%, even more preferably at least 90%, most preferably at least 95%. Typically, the polypeptide has at least about 75%, preferably at least 80%, more preferably at least 85%, even more preferably at least 90%, and most preferably at least about 95% sequence identity with a polypeptide having amino acid residues 27 to 400 of SEQ ID NO: 15, amino acids 27 to 369 of SEQ ID NO: 17, amino acids 27 to 374 of SEQ ID NO: 5, a ligand-binding domain of a GFRα3 polypeptide of amino acids 84 to 360 of SEQ ID NO: 15, amino acids 84 to 329 of SEQ ID NO: 17, or the sequence of amino acids 110 to 386 of SEQ ID NO: 20. Preferably the identity is to amino acid residues 27 to 400 of SEQ ID NO: 15 and DNA encoding it. The isolated nucleic acid molecule can contain a DNA encoding a GFRα3 polypeptide having amino acid residues 27 to 400 of SEQ ID NO:15, or is complementary to such encoding nucleic acid sequence, and remains stably bound to it under at least moderate, and optionally, under high stringency conditions. The protein can be encoded by the nucleic acid encoding the full length protein of clone DNA48613, DNA48614 or murine GFRα3 (clone 13), or one that hybridizes thereto under stringent conditions. DNA48613 (SEQ ID NO:14) and DNA 48614 (SEQ ID NO:16) were deposited with the ATCC under accession numbers ATCC 209752 (Designation: DNA48613-1268), ATCC 209751 (Designation: DNA48614-1268), respectively, on Apr. 07 1998.

The variations can be made using methods known in the art such as oligonucleotide-mediated (site-directed) mutagenesis, alanine scanning, and PCR mutagenesis. Site-directed mutagenesis (Carter, et al., *Nucl. Acids Res.,* 13:4331 (1986); Zoller, et al., *Nucl. Acids Res.,* 10:6487 (1987)), cassette mutagenesis (Wells, et al., *Gene,* 34:315 (1985)), restriction selection mutagenesis (Wells, et al., *Philos. Trans. R. Soc. London SerA,* 317:415 (1986)) or other known techniques can be performed on the cloned DNA to produce the GFRα3 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, *J. Mol. Biol.,* 150:1 (1976)). If alanine substitution does not yield adequate amounts of variant, an isoteric amino acid can be used.)

C. Modifications of GFRα3

Covalent modifications of GFRα3 are included within the scope of this invention. One type of covalent modification includes reacting targeted amino acid residues of the GFRα3 with an organic derivatizing agent that is capable of reacting with selected side chains or the N- or C-terminal residues of the GFRα3. Derivatization with bifunctional agents is useful, for instance, for crosslinking GFRα3 to a water-insoluble support matrix or surface for use in the method for purifying anti-GFRα3 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a -amino groups of lysine, arginine, and histidine side chains (T. E. *Creighton, Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification of the GFRα3 polypeptide included within the scope of this invention comprises altering the native glycosylation pattern of the polypeptide. "Altering the native glycosylation pattern" is intended for purposes herein to mean deleting one or more carbohydrate moieties found in native sequence GFRα3, and/or adding one or more glycosylation sites that are not present in the native sequence GFRα3, and/or alteration of the ratio and/or composition of the sugar residues attached to the glycosylation site(s).

Addition of glycosylation sites to the GFRα3 polypeptide may be accomplished by altering the amino acid sequence. The alteration may be made, for example, by the addition of, or substitution by, one or more serine or threonine residues to the native sequence GFRα3 (for O-linked glycosylation sites). The GFRα3 amino acid sequence may optionally be altered through changes at the DNA level, particularly by mutating the DNA encoding the GFRα3 polypeptide at preselected bases such that codons are generated that will translate into the desired amino acids.

Another means of increasing the number of carbohydrate moieties on the GFRα3polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259-306 (1981).

Removal of carbohydrate moieties present on the GFRα3 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo- and exo-glycosidases as described by Thotakura, et al., *Meth. Enzymol.*, 138:350 (1987).

Another type of covalent modification of GFRα3 comprises linking the GFRα3 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The GFRα3 of the present invention may also be modified in a way to form a chimeric molecule comprising GFRα3 fused to another, heterologous polypeptide or amino acid sequence. In one embodiment, such a chimeric molecule comprises a fusion of the GFRα3 with a tag polypeptide which provides an epitope to which an anti-tag antibody can selectively bind. The epitope tag is generally placed at the amino- or carboxyl-terminus of the GFRα3. The presence of such epitope-tagged forms of the GFRα3 can be detected using an antibody against the tag polypeptide. Also, provision of the epitope tag enables the GFRα3 to be readily purified by affinity purification using an anti-tag antibody or another type of affinity matrix that binds to the epitope tag. In an alternative embodiment, the chimeric molecule may comprise a fusion of the GFRα3 with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field, et al., *Mol. Cell. Biol.*, 8:2159-2165 (1988)); the c-myc tag and the 8F9, 3C7, 6E10, G4, B7 and 9E10 antibodies thereto (Evan, et al., *Molecular and Cellular Biology*, 5:3610-3616 (1985)); and the Herpes Simplex virus glycoprotein D (gD) tag and its antibody (Paborsky, et al., *Protein Engineering*, 3(6):547-553 (1990)). Other tag polypeptides include the Flag-peptide (Hopp, et al., *BioTechnology*, 6:1204-1210 (1988)); the KT3 epitope peptide (Martin, et al., *Science*, 255:192-194 (1992)); an a-tubulin epitope peptide (Skinner, et al., *J. Biol. Chem.* 266:15163-15166 (1991)); and the T7 gene 10 protein peptide tag (Lutz-Freyermuth et al., *Proc. Natl. Acad. Sci. USA*, 87:6393-6397 (1990)).

D. Preparation of GFRα3

The description below relates primarily to production of GFRα3 by culturing cells transformed or transfected with a vector containing GFRα3 nucleic acid. It is, of course, contemplated that alternative methods, which are well known in the art, may be employed to prepare GFRα3. For instance, the GFRα3 sequence, or portions thereof, may be produced by direct peptide synthesis using solid-phase techniques (see, e.g., Stewart, et al., *Solid-Phase Peptide Synthesis, W.H. Freeman Co., San Francisco, Calif. (*1969); Merrifield, *J. Am. Chem. Soc.*, 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the GFRα3 may be chemically synthesized separately and combined using chemical or enzymatic methods to produce the full-length GFRα3 .

1. Isolation of DNA Encoding GFRα3

DNA encoding GFRα3 may be obtained from a cDNA library prepared from tissue believed to possess the GFRα3 mRNA and to express it at a detectable level. Accordingly, human GFRα3 DNA can be conveniently obtained from a cDNA library prepared from human tissue, such as described in the Examples. The GFRα3-encoding gene may also be obtained from a genomic library or by oligonucleotide synthesis.

Libraries can be screened with probes (such as antibodies to the GFRα3 or oligonucleotides of at least about 20-80 bases) designed to identify the gene of interest or the protein encoded by it. Screening the cDNA or genomic library with the selected probe may be conducted using standard procedures, such as described in Sambrook, et al., *Molecular Cloning: A Laboratory Manual* (New York: Cold Spring Harbor Laboratory Press, 1989). An alternative means to isolate the gene encoding GFRα3 is to use PCR methodology (Sambrook, et al., supra; Dieffenbach, et al., *PCR Primer: A Laboratory Manual* (Cold Spring Harbor Laboratory Press, 1995)).

Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as BLAST, BLAST-2, ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for GFRα3 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transformations have been described in U.S. Pat. No. 4,399,216. Transformations into yeast are typically carried out according to the method of Van Solingen, et al., *J. Bact.,* 130:946 (1977) and Hsiao, et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown, et al., *Methods in Enzymology,* 185:527-537 (1990) and Mansour, et al., *Nature,* 336: 348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 7,325) and K5 772 (ATCC 53,635).

In addition to prokaryotes, eukaryotic microbes such as filamentous fungi or yeast are suitable cloning or expression hosts for GFRα3-encoding vectors. *Saccharomyces cerevisiae* is a commonly used lower eukaryotic microorganism.

Suitable host cells for the expression of glycosylated GFRα3 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham, et al., *J. Gen Virol.,* 36:59 (1977); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding GFRα3 maybe inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The GFRα3 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the GFRα3 DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* a-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. An example of suitable selectable markers for mammalian cells are those that enable the identification of cells competent to take up the GFRα3 nucleic acid, such as DHFR or thymidine kinase. An appropriate host cell when wild-type DHFR is employed is the CHO cell line deficient in DHFR activity, prepared and propagated as described by Urlaub, et al., *Proc. Natl. Acad. Sci. USA,* 77:4216 (1980). A suitable selection gene for use in yeast is the trp1 gene present in the yeast plasmid YRp7 (Stinchcomb, et al., *Nature,* 282:39 (1979); Kingsman et al., *Gene,* 7:141 (1979); Tschernper, et al., *Gene,* 10:157 (1980)). The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the GFRα3 nucleic acid sequence to direct mRNA synthesis. Promoters recognized by a variety of potential host cells are well known. Promoters suitable for use with prokaryotic hosts include the b-lactamase and lactose promoter systems (Chang, et al., *Nature,* 275:615 (1978); Goeddel, et al., *Nature,* 281:544 (1979)), alkaline phosphatase, a tryptophan (trp) promoter system (Goeddel, *Nucleic Acids Res.,* 8:4057 (1980); EP 36,776), and hybrid promoters such as the tac promoter (deBoer, et al., *Proc. Natl. Acad. Sci. USA,* 80:21-25 (1983)). Promoters for use in bacterial systems also will contain a Shine-Dalgarno (S.D.) sequence operably linked to the DNA encoding GFRα3.

Examples of suitable promoting sequences for use with yeast hosts include the promoters for 3-phosphoglycerate kinase (Hitzeman, et al., *J. Biol. Chem.,* 255:2073 (1980)) or other glycolytic enzymes (Hess, et al., *J. Adv. Enzyme Reg.,* 7:149 (1968); Holland, *Biochemistry,* 17:4900(1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

GFRα3 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the GFRα3 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the GFRα3 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding GFRα3.

Still other methods, vectors, and host cells suitable for adaptation to the synthesis of GFRα3 in recombinant vertebrate cell culture are described in Gething, et al., *Nature,* 293:620-625 (1981); Mantei, et al., *Nature* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence GFRα3 polypeptide or against a synthetic peptide based on the DNA sequences provided herein or against exogenous sequence fused to GFRα3 DNA and encoding a specific antibody epitope.

5. Purification of Polypeptide

Forms of GFRα3 may be recovered from culture medium or from host cell lysates. If membrane-bound, it can be released from the membrane using a suitable detergent solution (e.g. Triton-X 100) or by enzymatic cleavage. Cells employed in expression of GFRα3 can be disrupted by various physical or chemical means, such as freeze-thaw cycling, sonication, mechanical disruption, or cell lysing agents.

It may be desired to purify GFRα3 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the GFRα3. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular GFRα3 produced.

E. Uses for GFRα3

Nucleotide sequences (or their complement) encoding GFRα3 have various applications in the art of molecular biology, including uses as hybridization probes, in chromosome and gene mapping and in the generation of anti-sense RNA and DNA. GFRα3 nucleic acid will also be useful for the preparation of GFRα3 polypeptides by the recombinant techniques described herein.

The full-length native sequence GFRα3 (in SEQ ID NO:14) gene, or portions thereof, may be used as hybridization probes for a cDNA library to isolate the full-length gene or to isolate still other genes (for instance, those encoding naturally-occurring variants of GFRα3 or GFRα3 from other species) which have a desired sequence identity to the GFRα3 sequence disclosed in SEQ ID NO: 15. Optionally, the length of the probes will be about 20 to about 50 bases. The hybridization probes may be derived from the nucleotide sequence of SEQ ID NO:14 or from genomic sequences including promoters, enhancer elements and introns of native sequence GFRα3. By way of example, a screening method will comprise isolating the coding region of the GFRα3 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the GFRα3 gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related GFRα3 sequences.

Nucleotide sequences encoding a GFRα3 can also be used to construct hybridization probes for mapping the gene which encodes that GFRα3 and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for GFRα3 encode a protein which binds to another protein (example, where the GFRα3 is a receptor), the GFRα3 can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor GFRα3 can be used to isolate correlative ligand(s). Screening assays can be designed to find lead compounds that mimic the biological activity of a native GFRα3 or a receptor for GFRα3. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode GFRα3 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding GFRα3 can be used to clone genomic DNA encoding GFRα3 in accordance with established techniques and the genomic sequences used to generate transgenic animals that contain cells which express DNA encoding GFRα3. Methods for generating transgenic animals, particularly animals such as mice or rats, have become conventional in the art and are described, for example, in U.S. Pat. Nos. 4,736,866 and 4,870,009. Typically, particular cells would be targeted for GFRα3 transgene incorporation with tissue-specific enhancers. Transgenic animals that include a copy of a transgene encoding GFRα3 introduced into the germ line of the animal at an embryonic stage can be used to examine the effect of increased expression of DNA encoding GFRα3. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Non-human homologues of GFRα3 can be used to construct a GFRα3 "knock out" animal which has a defective or altered gene encoding GFRα3 as a result of homologous recombination between the endogenous gene encoding GFRα3 and altered genomic DNA encoding GFRα3 introduced into an embryonic cell of the animal. For example, cDNA encoding GFRα3 can be used to clone genomic DNA encoding GFRα3 in accordance with established techniques. A portion of the genomic DNA encoding GFRα3 can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, *Cell,* 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., *Cell,* 69:915 (1992)). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the GFRα3 polypeptide.

Agents which bind to the GFRα3 molecule could be useful in the treatment of diseases or conditions involving the peripheral nervous system. For example, such ligands can be used to treat peripheral neuropathies associated with diabetes, HIV, chemotherapeutic agent treatments. Ligands binding to GFRα3 are expected to be useful in the treatment of neuropathic pain, antagonists of GFRα3 are expected to be useful to treat chronic pain of non-neuropathic nature such as, but not limited to, that which is associated with various inflammatory states. The above therapies are consistent with the data of Example 5 in which a strong expression of GFRα3 within developing and adult sensory ganglia was observed. GFRα3 or its agonist or antagonists can be used to treat conditions involving dysfunction of the autonomic nervous system including, but not limited to, disturbances in blood pressure or cardiac rhythm, gastrointestinal function, impotence, and urinary continence. Other indications for ligands binding to GFRα3 include: post-herpetic neuralgia, shingles, asthma, irritable bowel, inflammatory bowel, cystitis, headache (migraine), arthritis, spinal cord injury, constipation, hypertension, mucositis, dry mouth or eyes, fibromyalgia, chronic back pain, or wound healing. These uses are consistent with the observed expression in sympathetic ganglia.

The surprising, relative lack of expression of GFRα3 in many organs, including notably brain, gut, and kidney indicates that the ligand (and other agonists or antagonists) which binds this receptor lacks some side effects which may be associated with ligands which bind to GFRα1 and GFRα2 (GDNF and neurturin). Thus, ligands which act via GFRα3 will be particularly useful to treat disorders of the peripheral nervous system while inducing fewer effects on weight loss, motor function, or on kidney function than would ligands acting via GFRα1 or GFRα2.

F. Anti-GFRα3 Antibodies

The present invention further provides anti-GFRα3 antibodies. Exemplary antibodies include polyclonal, monoclonal, humanized, bispecific, and heteroconjugate antibodies.

1. Polyclonal Antibodies

The anti-GFRα3 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the GFRα3 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-GFRα3 antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the GFRα3 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against GFRα3. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones maybe isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies maybe monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized Antibodies

The anti-GFRα3 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones, et al., *Nature,* 321:522-525 (1986); Riechmann, et al., *Nature,* 332:323-329 (1988); and Presta, *Curr. Op. Struct. Biol.,* 2:593-596 (1992)).

Methods for humanizing non-human antibodies are well known in the art. Generally, a humanized antibody has one or more amino acid residues introduced into it from a source which is non-human. These non-human amino acid residues are often referred to as “import” residues, which are typically taken from an “import” variable domain. Humanization can be essentially performed following the method of Winter and co-workers (Jones, et al., *Nature,* 321:522-525 (1986); Riechmann, et al., *Nature,* 332:323-327 (1988); Verhoeyen, et al., *Science,* 239:1534-1536 (1988)), by substituting rodent CDRs or CDR sequences for the corresponding sequences of a human antibody. Accordingly, such “humanized” antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.,* 227:381 (1991); Marks, et al., *J. Mol. Biol.,* 222:581 (1991)). The techniques of Cole et al. and Boerner et al. are also available for the preparation of human monoclonal antibodies (Cole, et al., *Monoclonal Antibodies and Cancer Therapy*, Alan R. Liss, p. 77 (1985) and Boerner, et al., *J. Immunol.,* 147(1):86-95 (1991)).

4. Bispecific Antibodies

Bispecific antibodies are monoclonal, preferably human or humanized, antibodies that have binding specificities for at least two different antigens. In the present case, one of the binding specificities is for the GFRα3, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature,* 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker, et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymolopy,* 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies maybe prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-GFRα3 Antibodies

The anti-GFRα3 antibodies of the invention have various utilities. For example, anti-GFRα3 antibodies may be used in diagnostic assays for GFRα3, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147-158). The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter, et al., *Nature,* 144:945 (1962); David, et al., *Biochemistry,* 13:1014 (1974); Pain, et al., *J. Immunol. Meth.,* 40:219 (1981); and Nygren, *J. Histochem. and Cytochem.,* 30:407 (1982).

Anti-GFRα3 antibodies also are useful for the affinity purification of GFRα3 from recombinant cell culture or natural sources. In this process, the antibodies against GFRα3 are immobilized on a suitable support, such a Sephadex resin or filter paper, using methods well known in the art. The immobilized antibody then is contacted with a sample containing the GFRα3 to be purified, and thereafter the support is washed with a suitable solvent that will remove substantially all the material in the sample except the GFRα3, which is bound to the immobilized antibody. Finally, the support is washed with another suitable solvent that will release the GFRα3 from the antibody.

H. Assays For Ligand-Induced A-Subunit Activity

The compounds and methods of the invention can be used in assays to detect molecules that activate or inhibit GFRα3 signal transduction, and indeed can be applied to other α-subunit receptor molecules (e.g., GFRα1, GFRα2, GFRα4) that homo-dimerize or homo-oligomerize upon acitvation by a ligand or other agonist. The assays are based on the surprising fact that the α-subunit receptors can homo-dimerize or homo-oligomerize upon ligand binding. And further that this dimerization of an α-subunit, when fused to a receptor protein kinase intracellular domain capable of kinase activity, preferably tyrosine kinase activity, results in kinase activity, e.g. readily detectable autophosphorylation. While the methods and contructs herein are discussed in terms of one or another GFRα subunit receptor disclosed herein, the methods will apply readily to any α-receptor in the α-subunit receptor family—a family in which the α-subunit receptor is the ligand-binding partner of a multi-subunit signal transduction complex containing a beta subunit that typically contains a tyrosine kinase activity that is activated upon ligand-activated α-subunit binding to the beta subunit.

Various assays have been developed which measure kinase activity, and in particular tyrosine kinase activity. Some of these assays measure the ability of a tyrosine kinase enzyme to phosphorylate a synthetic substrate polypeptide. For example, an assay has been developed which measures growth factor-stimulated tyrosine kinase activity by measuring the ability of the kinase to catalyze the transfer of the γ-phosphate of ATP to a suitable acceptor substrate. See Pike, L., *Methods of Enzymology* 146:353-362 (1987) and Hunter, *Journal of Biological Chemistry* 257(9):4843-4848 (1982), for example. In this assay, the use of (γ-$^{32}$P)ATP permits the radioactive labeling of the posphorylated substrate, which is a synthetic tyrosine-containing peptide. Others have described protein kinase assays wherein incorporation of $^{32}$P into a tyrosine kinase receptor, such as the EGF receptor (see Donato, et al., *Cell Growth Differ.* 3:259-268 (1992)), insulin receptor (see Kasuga, et al., *Journal of Biological Chemistry* 257(17):9891-9884 (1982) and Kasuga, et al., *Methods in Enzymology* 109:609-621 (1985)), and liver growth hormone receptor (see Wang, et al., *Journal of Biological Chemistry* 267(24):17390-17396 (1992)), is measured.

Construction of α-receptor constructs, including fusions to Rse or other tyrosine kinase domains, vectors for expressing such contructs, transfected or transformed host cells expressing these constructs, and means to enhance their expression at the cell surface are achieved as would be known in the art using, for example, the techniques as described herein for GFRα3 expression. Some particularly preferred means are provided below.

1. Kinase Receptor Activation—KIRA

The first stage of an assay of the invention involves phosphorylation of the kinase domain of a receptor construct, wherein the receptor construct is present in the cell membrane of a eukaryotic cell. The receptor construct can be derived from a nucleic acid encoding the receptor construct (as described herein) that can be transformed into the cell. In one embodiment of the invention, nucleic acid encoding a receptor construct is transformed into the cell. Preferred and exemplary techniques for transforming the cell with either the receptor or the receptor construct nucleic acid follow.

a. Transformation of the Cells

The instant invention provides a substantial improvement over in vitro soluble kinase receptor assays insofar as it is considered to more accurately reflect the activity of the α-subunit receptor in situ. It has been discovered that it is possible to transform eukaryotic cells with a receptor construct (comprising the α-subunit receptor and a kinase domain fusion and optionally, either an amino- or carboxyl-terminal flag polypeptide) so that the receptor construct assembles itself appropriately in the cell membrane and still retains kinase activity which can be detected in the ELISA stage of the assay. This provides a generic assay for measuring ligand binding activity, via the kinase activity of the fusion, of any α-subunit receptor of interest that homo-dimerizes or homo-oligomerizes upon ligand-binding.

If a suitable capture agent as described herein is available for a selected receptor construct, cells can be transformed with the nucleic acid encoding the receptor construct alone, without the flag polypeptide.

In order to provide nucleic acid encoding a receptor construct, nucleic acid encoding the α-subunit receptor is fused at its 3' end to nucleic acid encoding the intracellular catalytic kinase domain of a receptor kinase, preferably a rPTK, including a transmembrane domain, and optionally to the N-terminus of the flag polypeptide. Alternatively, the nucleic acid encoding the α-subunit receptor-kinase domain fusion will be fused at its 5' end to nucleic acid encoding the carboxyl terminus of the flag polypeptide. Thus, the flag polypeptide is provided at either the carboxyl- or amino-terminus of the receptor construct. Examples of suitable flag polypeptides are provided above. Selection of other suitable flag polypeptides is possible using the techniques described herein.

In order to generate fusions between the Rse.flag reagent and a α-subunit receptor of interest, the nucleic acid encoding the ECD (or GPI-anchor minus variant) of the α-subunit receptor of interest is fused at its 3' end to the nucleic acid encoding the amino terminus of the Rse.flag reagent.

Incorporation of a signal sequence into the expression vector is required since the receptor construct must be transported to the cell membrane where it is positioned such that the ECD faces the external milieu of the cell. Therefore, a signal sequence suitable for positioning the receptor construct in such a manner is used. The signal sequence is generally a component of the vector, or it may be a part of the receptor construct DNA that is inserted into the vector. If a heterologous signal sequence is used, it is from those that are recognized and processed (i.e., cleaved by a signal peptidase) by the host cell.

b. Selecting Cells for Use in the Assay

As mentioned above, the cells to be subjected to the assay are preferably cells transformed with a receptor construct. The suitability of the cells for use in the assay is investigated.

If the cell line is transformed with the receptor construct (without the flag polypeptide) it can be readily discovered whether the cell line is suitable for use in the assay. As a first step, successful transformation and expression of the nucleic acid encoding the receptor construct is determined. The strategy found in U.S. Pat. No. 5,766,863, or its corresponding WO publication, entitled "Kinase receptor activation assay" can be followed. In order to identify whether the ECD of the receptor construct is present on the surface of the cells, flow cytometric analysis can be performed using an antibody to the ECD of the α-subunit receptor. The antibody can be made using the techniques for generating antibodies discussed herein. Flow cytometric analysis can be carried out using the techniques described in *Current Protocols in Immunology*, Ed. Coligen, et al., Wiley publishers, Vols. 1 and 2, for example. Briefly, flow cytometric analysis involves incubating intact cells (having the receptor) with antibodies to the ECD thereof, followed by washing. The antibody-bound cells are then incubated with species specific anti-antibody antibodies conjugated to a fluorochrome. Following washing, the labeled cells are analyzed by fluorescence-activated flow cytometry to detect whether the ECD is present on the surface of the cells.

In the following step, the ability of the cell-bound receptor to be activated is tested. In order to determine this, the transformed cells are exposed to a known agonist to the receptor (e.g. the endogenous ligand or an agonist antibody for the receptor). In the case of GFRα3 the natural ligand is artemin. Following exposure, the cells are lysed in a suitable buffer (e.g. sodium dodecylbenzenesulfonate in phosphate buffered saline; SDS in PBS) and subjected to Western blotting with anti-phosphotyrosine antibodies as described in Wang, *Molecular and Cellular Biology* 5(12):3640-3643 (1985); Glenney, et al., *Journal of Immunological Methods* 109:277-285 (1988); Kamps, *Methods in Enzymology* 201:101-110 (1991); Kozma, et al., *Methods in Enzymology* 201:28-43 (1991); Holmes, et al., *Science* 256:1205-10 (1992); or Corfas, et al., *PNAS, USA* 90:1624-1628 (1993), for example.

Assuming the Western blotting step indicates that the receptor construct can be activated, a KIRA ELISA test run can be performed to further establish whether or not the transformed cell line can be used in the assay.

In the preferred embodiment of the invention, the KIRA ELISA is a "generic" assay insofar as any α-subunit receptor of interest can be studied regardless of the availability of receptor-specific reagents (i.e., capture agent). This embodiment employs a receptor construct having a flag polypeptide at either the amino or carboxyl terminus of the receptor.

If the flag polypeptide is provided at the $NH_2$-terminus (see, e.g., the gD.trk A, B and C receptor constructs), the procedure for selecting a transformed cell line for use in the assay is similar to that described above. In this embodiment, the cells are transformed with the flag polypeptide-receptor construct as described earlier herein. Successful transformation of the receptor and flag polypeptide (i.e. the receptor construct in this example) is confirmed. In order to study this, two-dimensional flow cytometric analysis can be performed using antibodies to both the flag polypeptide and the ECD of the receptor. Techniques for two-dimensional flow cytometric analysis are disclosed in *Current Protocols in Immunology*, supra.

Cells which have been successfully transformed with the receptor construct having a C-terminal flag polypeptide are also suitable for use in the assay. Following cell transformation, successful transformation of the receptor is determined by flow cytometric analysis using an antibody directed against the ECD of the receptor of interest, for example. Flow cytometric analysis can be performed substantially as described above. Successful transformation of the entire receptor construct (including the COOH-terminal flag polypeptide) is then analyzed. This can be achieved by lysing the cells (using techniques for lysing cells disclosed herein) and immunoprecipitating the membrane extract with an antibody against the α-subunit receptor of interest. This immunoprecipitated membrane extract is then subjected to Western blot analysis with antibodies specific for the flag polypeptide. Alternatively, α-subunit specific ELISA analysis of anti-flag polypeptide captured membrane lysate can be carried out. Briefly, this involves coating ELISA wells with appropriate flag specific capture agent. The wells are blocked, washed, and then lysate is then incubated in the wells. Unbound receptor construct is removed by washing. The wells are then reacted with receptor-specific antibody or antibodies, either directly or indirectly conjugated to HRPO. The wells are washed and the HRPO is then exposed to the chromogenic substrate (e.g., TMB). Detecting receptor activation and KIRA ELISA test run, are essentially the same as those steps described above.

Once useful cells are identified, they are subjected to the KIRA stage of the instantly claimed assay.

c. Coating the First Solid Phase with the Cells

The first solid phase (e.g. a well of a first assay plate) is coated with cells which have been transformed pursuant to the preceding sections.

Preferably, an adherent cell line is chosen, so that the cells naturally adhere to the first solid phase. However, use of an adherent cell line is not essential. For example, non-adherent cells (e.g. red blood cells) can be added to round bottomed wells of an assay plate such as that sold by Becton Dickinson Labware, Lincoln Park, N.J., for example. The assay plate is then placed in a plate carrier and centrifuged so as to create a pellet of cells adhering to the base of the wells. The cell culture supernatants are removed using a pipette. Thus, use of an adherent cell is clearly advantageous over non-adherent cells since it reduces variability in the assay (i.e, the cells in the pellet of the round bottom wells may be taken up with the supernatant when the alternative method is used).

The cells to be added to the wells of the first assay plate may be maintained in tissue culture flasks and utilized when cells densities of about 70-90% confluency are achieved. Then, generally between about $1\times10^4$ to $3\times10^5$ (and preferably $5\times10^4$ to $1\times10^5$) cells are seeded per flat-bottom well, using a pipette, for ex has been found that, contrary to expectations, addition of cell concentrations mentioned above is sufficient to enable activation of the receptor construct to be measured in the ELISA stage of the assay, without the need to concentrate or clarify the cells or cell lysate prior thereto. Often, the cells are diluted in culture medium prior to seeding them in the wells of the microtiter plate to achieve the desired cell densities.

Usually, the cells are cultured in the microtiter plates for a sufficient period of time to optimize adherence to the wells thereof, but not too long such that the cells begin to deteriorate. Thus, incubation for about 8 to 16 hours at a temperature which is the physiological optimum for the cells (usually about 37° C.) is preferred. Suitable media for culturing the cells are described in Section 1A above. Culturing in 5% $CO_2$ is recommended.

Following incubation overnight, the well supernatants are decanted and excess supernatant may be further removed by lightly tamping the microtiter plates with an absorbent substrate, e.g., a paper towel, but a sponge works equally well. Thus, a substantially homogeneous layer of adhering cells remains on the internal surfaces of the individual wells of the microtiter plate. These adhering cells are then exposed to the analyte.

d. Preparation and Addition of the Analyte

As mentioned above, the analyte may comprise an agonist ligand (or suspected agonist) or an antagonist (or suspected antagonist) for the α-subunit receptor of interest. The ligand may be an endogenous polypeptide, or a synthetic molecule, such as an inorganic or organic molecule. Usually, the ligand is a polypeptide. This assay is useful for screening molecules which activate (or antagonize activation) of the α-subunit receptor of interest. Thus, the assay can be used for developing therapeutically effective molecules.

Where the ligand is an agonist, the molecule can comprise the native growth factor e.g., artemin, neurturin, GDNF, and persephin. Many of these growth factors are available commercially. Alternatively, the growth factor can be made by peptide synthesis or recombinant techniques which are described herein. Synthetic small molecule agonists can similarly be generated by those skilled in the art using conventional chemical synthesis techniques. Preferably, one is assaying for agonist or antagonist antibodies.

Where the ligand is present in a biological fluid, the analyte can be prepared using techniques which are well known in the art. Body fluid such as blood or amniotic fluid may be used directly, however concentration may be required. If the analyte to be tested comprises a particular tissue, the cells thereof can be grown in cell culture and the supernatant can be tested for secreted ligand.

Often, the ligand is diluted in an aqueous diluent (such as cell culture media) so that a standard curve can be generated. However, the ligand may be present in a cell or a cell component (e.g., the cell membrane). In particular, it has been found that the assay can be used to detect the presence of a ligand in the cell membrane of a selected cell line. This is clearly useful for discovering a novel endogenous ligand for a known α-subunit receptor.

The ligand composition is added to each well which contains the adhering cells using a pipette, for example. At least one control well (e.g. to which the aqueous diluent for the ligand is added) is included in the assay.

The adhering cells are usually stimulated for a sufficient period of time to optimize the signal, but not too long such that the signal decreases as a consequence of dephosphorylation of the receptor by endogenous phosphatases. A suitable stimulation period is between about 10 to 60 minutes, preferably about 30 minutes at a physiologically optimal temperature for the cells (usually about 37° C.).

Following activation, well supernatants are decanted and the plates can then be lightly tamped with an absorbent substrate to remove excess supernatant.

The assay can be used to detect antagonist ligands for the receptor of interest. Antagonists generally fall into two categories (a) ones which bind to the receptor and thereby block binding and/or activation of the receptor by an agonist thereto (the antagonist may bind to the ECD, but this is not necessarily the case) and (b) those which bind to the agonist and thus prevent activation of the receptor by the agonist.

In order to detect antagonist molecules from category (a) above, the cells are exposed to the suspected antagonist ligand substantially as mentioned above. Following exposure to the antagonist, the well supernatants are decanted and the plates are lightly tamped. Then, a known agonist (e.g., the endogenous growth factor) is added to the washed cells essentially as discussed in the preceding paragraphs, following which, the well supernatants are decanted and plates are lightly tamped. Alternatively, a composition comprising both the antagonist and agonist can be added to the adhering cells substantially as discussed above. Ability of the suspected antagonist to block binding and/or activation of the receptor can subsequently be measured by ELISA as discussed below.

To detect antagonist molecules from category (b) above, a known agonist is pre-incubated with the suspected antagonist prior to the KIRA stage of the assay. This incubation is carried out for a sufficient period of time to enable a complex of the antagonist-agonist to form; from 30 min. to 12 hours, for example. This complex is then subjected to the assay with the non-complexed agonist and antagonist used as controls.

Following exposure to the agonist (and optionally the antagonist) ligand, the cells are lysed, as discussed below.

e. Solubilizing the Cells

In this step of the assay, the cells are lysed so as to solubilize the receptor construct such that it remains activated (i.e., the tyrosine residues remain phosphorylated) for the ELISA stage of the assay. Thus, the cells are lysed using a lysis buffer as described above which serves to solubilize the receptor construct, yet does not dephosphorylate or denature the receptor construct.

Where microtiter plates are used as mentioned above, about 75 to 200 μl of lysis buffer is added to each well. The plates can then be agitated gently using a plate shaker (e.g., such as that sold by Bellco Instruments, Vineland, N.J.) for about 1 to 2 hours. Shaking can be carried out at room temperature.

2. Enzyme-Linked Immunosorbent Assay—ELISA

The second stage of the assay involves a sandwich ELISA performed in the second assay plate. In order to carry out the ELISA, a capture agent is prepared.

a. Preparation of the Capture Agent

As mentioned above, the capture agent often comprises a polyclonal antibody (usually an affinity purified polyclonal antibody) or monoclonal antibody. Other capture agents are envisaged and are discussed in the definitions section above. The capture agent either binds specifically to the receptor, or to the flag polypeptide (i.e. the antigen).

Polyclonal antibodies to the antigen (either the receptor or the flag polypeptide) generally are raised in animals by multiple subcutaneous (sc) or intraperitoneal (ip) injections of the antigen or an antigenic fragment thereof (often the ECD of the α-subunit receptor) and an adjuvant. It may be useful to conjugate the antigen or a fragment containing the target amino acid sequence to a protein that is immunogenic in the species to be immunized (e.g., keyhole limpet hemocyanin), using a bifunctional or derivatizing agent.

The route and schedule for administration of immunogen to the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant (or other suitable adjuvant) by subcutaneous injection at multiple sites. 7 to 14 days later animals are bled and the serum is assayed for anti-antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies can be prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones producing the desired antibody. The hybridoma technique described originally by Kohler and Milstein, *Eur. J. Immunol.* 6:511 (1976), and also described by Hammerling, et al., In: *Monoclonal Antibodies and T-Cell Hybridomas*, Elsevier, N.Y., pp. 563-681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-amninopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are then sterile filtered. Where the antibody is a polyclonal antibody, it is generally affinity purified using an affinity column generated from the antigen of interest so as to provide a substantially specific capture antibody. Affinity chromatography is usually preceded by other purification techniques, such as liquid chromatography.

In a further embodiment, antibodies or antibody fragments can be isolated from antibody phage libraries generated via the techniques described in McCafferty, et al., *Nature,* 348: 552-554 (1990), using the flag polypeptide, α-subunit receptor, or a fragment thereof, to select for a suitable antibody or antibody fragment. Clackson, et al., *Nature,* 352:624-628 (1991) and Marks, et al., *J. Mol. Biol.,* 222:581-597 (1991) describe the isolation of murine and human antibodies, respectively, using phage libraries. Subsequent publications describe the production of high affinity (nM range) human antibodies by chain shuffling (Mark, et al., *Bio/Technol.* 10:779-783 (1992)), as well as combinatorial infection and in vivo recombination as a strategy for constructing very large phage libraries (Waterhouse, et al., *Nuc. Acids Res.,* 21:2265-2266 (1993)). Thus, these techniques are viable alternatives to traditional monoclonal antibody hybridoma techniques for isolation of "monoclonal" antibodies which are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-receptor or anti-flag polypeptide monoclonal antibody herein. Thus, the antibody may be made by recombinant DNA methods (Cabilly et al., U.S. Pat. No. 4,816,567).

Binding of the capture agent is not affected by the presence or absence of a ligand bound to the receptor and the capture agent does not sterically block access to the phosphorylated tyrosine(s) by the anti-phosphotyrosine antibody. Furthermore, the capture agent does not, of course, activate the receptor of interest.

First, once the capture agent (e.g. an antibody or streptavidin) has been chosen, binding to either the receptor or the flag polypeptide (where a receptor construct is to be used in the assay) is confirmed. This can be determined by flow cytometric analysis, immuno-precipitation or antigen-coat ELISA, for example. Flow cytometric analysis has been described above. Immunoprecipitation usually involves lysing the cells (having the receptor construct) in non-ionic detergent (e.g. 0.5% Triton X-100) in a suitable buffer (e.g. PBS) and the cell lysates thus obtained are then incubated with the potential anti-receptor or anti-flag polypeptide capture agent. The immune complexes are precipitated with either (a) anti-capture agent antibodies in the presence of polyethylene glycol (PEG) which enhances precipitation of the immune complex or with (b) insoluble (e.g. agarose bound) protein A or protein G. The immunoprecipitated material is then analyzed by polyacrylamide gel electrophoresis (PAGE). For antigen-coat ELISA, ELISA wells are coated overnight with either the purified receptor, purified flag polypeptide or purified receptor construct. The coated wells are then exposed to the potential capture agent and screened with HRPO-conjugated species specific anti-capture agent antibody.

The ability of the capture agent to bind to the receptor or flag polypeptide in the presence of a ligand to the receptor is also confirmed. This can be analyzed by incubating the receptor construct with a known ligand for the receptor (e.g. the endogenous growth factor or an agonist antibody thereto). Flow cytometric analysis, immunoprecipitation or antigen-coat ELISA can then be performed substantially as described above to investigate binding of the capture agent.

Assuming the capture agent is suitable as determined by the preceding two steps, it is then shown that the capture agent does not induce receptor activation (i.e. autophosphorylation) either before or after cell lysis. Thus, the cell-bound receptor construct is exposed to either the potential capture agent or a negative control (e.g. a control antibody which does not activate the receptor). Following cell lysis, the receptor construct can be subjected to Western blot analysis using labeled anti-phosphotyrosine antibodies. See, e.g., Glenney, et al., *Journal of Immunological Methods* 109:277-285 (1988); Kamps, *Methods in Enzymology* 201:101-110 (1991); Kozma, et al.,

*Methods in Enzymology* 201:28-43 (1991); or Holmes, et al., *Science* 256:1205-10 (1992). To establish whether capture agent induces receptor activation following cell lysis, a trial run of the KIRA ELISA (with both the capture agent and a negative control as discussed above) can be performed.

Finally, the ability of an anti-phosphotyrosine antibody (e.g. biotinylated anti-phosphotyrosine antibody) to bind the activated receptor in the presence of the potential capture agent is confirmed by a trial run in the KIRA ELISA disclosed herein.

Assuming the capture agent meets all the criteria specified above, it has good potential for use in the KIRA ELISA.

Once a suitable capture agent has been prepared, the second solid phase is coated therewith. Between about 0.1 to 10 μg/ml of capture agent can be added to each well of the second assay plate using a pipette, for example. The capture agent is often provided in a buffer at a high pH (e.g., between about 7.5 to 9.6) so that it has an increased overall charge and therefore displays enhanced binding to the second assay plate. Usually, the capture agent will be incubated in the wells for between about 8 to 72 hours to enable a sufficient coating of the capture agent to form on the inside walls of the wells. This incubation is generally carried out at low temperatures (e.g., between about 3-8° C.) to avoid or reduce degradation of the capture agent.

Following incubation, the wells of the plate are decanted and tamped lightly with an absorbent substrate. Non-specific binding is then blocked. In order to achieve this, a block buffer, is added to the wells. For example, a block buffer containing bovine serum albumin (BSA) such as that sold by Intergen Company, Purchase, N.Y., is suitable. It has been found that addition of between about 100 to 200 μl of block buffer to each well followed by gentle agitation at room temperature for between about 1-2 hours is sufficient to block non-specific binding. It is also possible to add the block buffer directly to the cell lysate obtained in the previous step rather than to the second assay plate.

Following this, the capture agent-coated plates are washed several times (usually between about 3-8 times) with a wash buffer. The wash buffer can comprise phosphate buffered saline (PBS) at pH 7.0 to 7.5, for example. However, other wash buffers are available which can also be used. Conveniently, an automated plate washer, such as the ScanWasher 300 (Skatron Instruments, Inc., Sterling, Va.) can be used for this, and other, washing steps of the assay.

b. Measuring Tyrosine Phosphorylation

The activated, solubilized receptor construct is then added to the wells having the capture agent adhering thereto. As a general proposition, about 80% of cell lysate obtained as mentioned under Section above can be added to each well (i.e., about 60 to 160 μl depending on the original volume of the wells). The lysate is incubated with the capture agent for an adequate period of time to enable the receptor construct to be captured in the wells, e.g., from 1 to 3 hours. Incubation can be carried out at room temperature.

Unbound cell lysate is then removed by washing with wash buffer. Following this washing step, an amount of the anti-phosphotyrosine antibody which is equal to, or less than, the amount of block buffer added previously, is added to each well. For example, about 50 to 200 μl of an anti-phosphotyrosine antibody preparation having between about 0.3 to 0.5 μg/ml of antibody in a suitable buffer (e.g., PBS with a detergent such as those included in the lysis buffer) is added to the well. This is followed by a washing step to remove unbound anti-phosphotyrosine antibody.

Tyrosine phosphorylation is then quantified by the amount of anti-phosphotyrosine antibody binding to the second solid phase. Many systems for detecting the presence of an antibody are available to those skilled in the art. Some examples follow.

Generally, the anti-phosphotyrosine antibody will be labelled either directly or indirectly with a detectable label. Numerous labels are available which can be generally grouped into the following categories:

(a) Radioisotopes, such as $^{35}S$, $^{14}C$, $^{121}I$, $^{3}H$, and $^{125}I$. The antibody can be labeled with the radioisotope using the techniques described in *Current Protocols in Immunology*, supra, for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym*. (ed J. Langone & H. Van Vunakis), Academic press, New York, 73: 147-166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB)).

(ii) alkaline phosphatase (AP) with para-Nitrophenyl phosphate as chromogenic substrate.

(iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. See, *Current Protocols in Immunology*, supra, for a review of techniques involving biotin-avidin conjugation. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-phosphotyrosine antibody need not be labeled, and the presence thereof can be detected using a labeled anti-antiphosphotyrosine antibody (e.g. anti-mouse anti-phosphotyrosine antibody conjugated with HRPO).

In the preferred embodiment, the anti-phosphotyrosine antibody is labeled with an enzymatic label which catalyzes a color change of a substrate (such as tetramethyl benzimidine (TMB), or orthaphenylene diamine (OPD)). Thus, the use of radioactive materials is avoided. A color change of the reagent can be determined spectrophotometrically at a suitable wavelength (e.g. 450 nm for TMB and 490 nm for OPD, with a reference wavelength of 650 nm).

3. Intracellular Kinase Activity

The assay described herein is also used by measuring phosphorylation and/or activation of a intracellular kinase domain (e.g. form a cytoplasmic tyrosine kinases and/or cytoplasmic serine-threonine kinases) fused to the α-subunit receptor. Phosphorylation of these molecules can occur as a consequence of trans-phosphorylation of the intracellular kinase domain by a kinase receptor or "receptor complex" (which comprises one or more kinase receptors residing in a cell membrane). Examples of intracellular tyrosine kinases include insulin receptor substrate I (IRS-1), Shc, Ras and GRB2, for example. Antibodies to human Shc, human Ras and GRB2 can be obtained commercially from UBI, NY, which can be used as capture agents for these tyrosine kinases. Examples of intracellular serine-threonine kinases include MEK and MAPK.

In order to measure phosphorylation of receptor constructs containing catalytic domains from these kinases, the procedure is essentially as described above, the chimera referred to as a "kinase construct." Generally, a eukaryotic cell will be transformed with nucleic acid encoding a kinase construct. Upon expression of the nucleic acid, the kinase construct will reside intracellularly (i.e. in the cytoplasm). The cells comprising the kinase construct are subjected to the KIRA as discussed above. Exposure to the agonist may result in transphosphorylation of the intracellular kinase construct which can be quantified in the ELISA as elaborated above. The capture agent in the ELISA binds to either the intracellular kinase construct or to the flag polypeptide.

4. Serine-Threonine Kinase Activity

This assay is further used by measuring for phosphorylation and/or activation of serine-threonine kinase ICD domain fused to the α-subunit receptor. The term "serine-threonine kinase" refers to a kinase which phosphorylates a substrate which has at least one phosphate accepting alcohol group. The serine-threonine kinase is usually a "receptor" insofar as it has a ligand-binding ECD, TM domain and ICD. The ICD usually comprises a catalytic kinase domain and generally has one or more phosphate accepting serine and/or threonine residues. Examples of intracellular serine-threonine kinases include MEK and MAPK. Measuring phosphorylation of intracellular serine-threonine kinases can be done as described herein. Examples of serine-threonine kinase receptors that can provide suitable ICD domains for fusion to create a receptor construct include daf-1, activin type II receptor (ActR-II), activin type IIB receptor (ActR-IIB), TGF-β type II receptor (TβR-II), activin receptor-like kinase (ALK) -1, -2, -3, -4 and TGF-β type I receptor (TβR-1)/ALK-5. See ten Dijke et al., supra. The serine-threonine kinase assay is essentially the same as described above for tyrosine kinases, except that phosphorylation is quantified using anti-phosphoserine and/or anti-phosphothreonine antibodies. Anti-phosphoserine and anti-phosphothreonine monoclonal antibodies can be purchased from Sigma Immuno Chemicals, St Louis, Mo., for example.

5. Phosphatase Activity

Phosphatase activity can similarly be measured using the assay described herein. Phosphatase enzymes are able to dephosphorylate phosphorylated tyrosine, serine and/or threonine residues (i.e. liberate inorganic phosphate from phosphoric esters of such amino acid residues). Generally the phosphatase enzyme is specific for either tyrosine residues or serine-threonine residues but sometimes can dephosphorylate tyrosine, serine and threonine residues. Sometimes "endogenous" phosphatase activity is measured and this refers to the activity of phosphatase enzyme(s) which exist in nature in a selected cell. In order to quantify endogenous phosphatase activity, cells possessing at least one phosphatase are stimulated in the presence and absence of one or more phosphatase inhibitors. Examples of protein tyrosine phosphatase (PTPase) inhibitors include sodium orthovanadate and sodium molybdate (Sigma Chemical Co., St. Louis, Mo.). ICN Biochemicals supply okadaic acid which is a serine-threonine phosphatase inhibitor. As a general proposition, between about 1-10 μM phosphatase inhibitor can be added to each well of the assay plate. In all other respects, the assay is performed essentially as discussed above. Thus, the ability of endogenous phosphatases to dephosphorylate a kinase in the selected cell can be quantified.

In the preferred embodiment, a phosphatase enzyme of interest can be studied. Examples of protein tyrosine phosphatases (PTPases) include PTP1B, PTPMEG, PTP1c, Yop51, VH1, cdc25, CD45, HLAR, PTP18, HPTPα and DPTP10D. See Zhang and Dixon, *Adv. Enzym.*68: 1-36 (1994). Examples of protein serine-threonine phosphatases include PP1, PP2A, PP2B and PP2C. See *Meth. Enzym.*, ed Hunter & Sefton, Academic press, New York, 201:389-398 (1991). These proteins can be purchased commercially or made using the recombinant techniques described herein. To measure phosphatase activity, the KIRA ELISA can be performed essentially as described above with the following modifications. Following capture of the kinase or kinase construct (e.g. receptor construct) to the second solid phase and the washing step (to remove unbound cell lysate), the phosphatase of interest is added to the wells of the second assay plate and incubated with the adhering kinase or kinase construct. For example, between about 50-200 μl of the phosphatase in a suitable dilution buffer (see *Meth. Enzym.*, ed Hunter & Sefton, Academic press, New York, 201:416-440 (1991)) can be added to each well. This is generally followed by gentle agitation at room temperature (or 37° C.) for between about 30 min to 2 hours to allow the phosphatase to dephosphorylate the kinase. Following washing to remove the phosphatase, the decreased degree of phosphorylation of the kinase relative to the control (i.e. no phosphatase added) is quantified by ELISA as described earlier herein.

6. Kits

As a matter of convenience, the reagents can be provided in a kit, i.e., a packaged combination of reagents, for combination with the analyte in assaying the ability of the analyte to activate or prevent activation of a α-subunit receptor of interest. The components of the kit will be provided in predetermined ratios. Thus, a kit will comprise the specific second solid phase for the assay as well as the anti-flag polypeptide capture agent either packaged separately or captured to the second solid phase (e.g. a microtiter plate). Usually, other reagents, such as the anti-phosphotyrosine antibody labelled directly or indirectly with an enzymatic label will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. a block buffer and a lysis buffer) and the like. Conveniently, the kit can also supply the homogeneous population of cells which have been transformed with the receptor construct. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the KIRA ELISA.

7. Uses for the Assay

This application provides two assays which are useful for reliable, sensitive and quantitative detection of kinase activation, which reflects ligand-binding by an α-subunit receptor, caused by its homo-dimerization or homo-oligomerization. The first assay can be used where a receptor-specific capture antibody having the desired characteristics herein described is available or has been prepared. The second assay is a generic assay which enables activation of any receptor construct to be measured via the use of a flag polypeptide and a capture agent which binds specificity thereto.

These assays are useful for identifying novel agonists/antagonists for a selected receptor. Also, the assay provides a means for studying ligand-receptor interactions (i.e., mechanism studies). Also the presence of an endogenous receptor in a selected cell line can be quantified using the assay. The assays are further useful for identifying the presence of a ligand for a selected receptor in a biological sample and, e.g., establishing whether a growth factor has been isolated following a purification procedure. It is desirable to have an assay for measuring the ability of these growth factors to activate their respective receptors.

he assay also has clinical applications for detecting the presence of a ligand for a selected receptor (e.g. the GFRα3 receptor) in a biological sample taken from a human and thus patients having elevated or depressed levels of the ligand can be identified. This is particularly desirable where elevated or depressed levels of the ligand cause a pathological condition. Accordingly, candidates for administration of the selected ligand (e.g. insulin) can be identified through this diagnostic method. It is possible, using the assay disclosed herein, to assay the pK of agonists or antagonists administered to a patient. This assay also facilitates the detection of shed receptor in a biological sample.

The assay is also useful to quantify phosphatase activity of endogenous phosphatases or, in the preferred embodiment, a phosphatase of interest. This can be used for screening phosphatase inhibitors, for example.

The following examples are offered for illustrative purposes only, and are not intended to limit the scope of the present invention in any way. All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Cloning of Mouse GFRα3

Using sequences from the neurturin receptor, now known as GFRα2 ("glial-cell-line-derived neurotrophic factor family receptor alpha"), a novel, potential member of the GFRα family was identified as a mouse EST in a public gene database (Accession Numbers W99197 (SEQ ID NO: 1), AA041935 (SEQ ID NO: 2) and AA050083 (SEQ ID NO: 3)). A DNA fragment corresponding to this potentially new receptor was obtained by Marathon PCR using mouse E15 cDNA (Clontech, Inc. USA) as template and PCR primers derived from the mouse EST. The PCR product was then used to screen a lambda gt10 mouse E15 library (Clontech, Inc. USA) to obtain a full length clone. The nucleotide sequence of the full length mouse cDNA is provided as SEQ ID NO: 4 (FIG. 1A-1B). The protein sequence (SEQ ID NO: 5; see FIG. 1A-1B) encoded by the isolated DNA was designated GFRα3, since it was determined to be a novel protein with sequence identity to GFRα1 (formerly the GDNF Receptor alpha) and GFRα2 (formerly the Neurturin Receptor alpha; NTNRα). A comparison of the 397 amino acid mouse GFRα3 protein sequence (SEQ ID NO: 5) to rat GFRα1 (SEQ ID NO: 8) and rat GFRα2 (SEQ ID NO: 9) is provided in FIG. 2. The mGFRα3 sequence is believed to identify a novel series of homologs belonging to the GFR receptor family. Potential N-linked glycosylation sites are shown shaded in FIG. 2. The hydrophobic sequence involved in GPI-anchoring is overlined in FIG. 2, with possible GPI attachment site indicated by the asterisks. A variant of the mouse GFRα3 DNA contains a deletion of the "T" base at position 290 in FIG. 1A, resulting in a frameshift and truncation protein variant. The variant DNA is nonetheless useful for hybridization, diagnostics, and other uses of the DNA (excluding full-length protein production) discussed throughout this specification. DNA (positions 89-289) comprising the GFRα3 coding region immediately upstream of this base find use in the invention. DNA comprising the sequence immediately downstream (291-1279) provide another useful embodiment of the invention.

In situ hybridization studies using DNA encoding mouse GFRα3 revealed a pattern of expression in peripheral sensory neurons and sympathetic neurons (data not shown).

Example 2

Isolation of cDNA Clones Encoding Human GFRα3

To identify rapidly whether a human homolog of this new receptor might exist, an expressed sequence tag (EST) DNA database (a proprietary EST database, LIFESEQ™, Incyte Pharmaceuticals, Palo Alto, Calif.) was searched and an EST (INC3574209) was identified having the sequence:

```
                                         (SEQ ID NO: 10)
GCGCTGNNTGNCNGNANGNGGGGGCGGGAGGTGCCGGTCGAGGGAGCCCC

GCTCTCAGAGCTCCAGGGGAGGAGCGANGGGAGCGCGGAGCCCGGCCGCC

TACAGCTCGCCATGGTGCGCCCCCTGAACCCGCGACCGCTGCCGCCCGTA

GNNNNNNNNNNNNNNNNNNNNNNNNNNNNNNNNNNNNNNNGCCTCTCGCAGC

CGGAGACCCCCTTCCCACAGAAAGCCGACTCATGAACAGCTGTCTCCAGG

CCAGGAGGAAGTGCCAGGCTGATCCCACCTGC.
```

This sequence had 61% identity to the murine GFRα3.

To clone the corresponding full length cDNA, a panel of cDNA libraries were screened with primers:

```
newa3.F
5' GCC TCT CGC AGC CGG AGA CC 3'    (SEQ ID NO: 11)

newa3.R
5' CAG GTG GGA TCA GCC TGG CAC 3'   (SEQ ID NO: 12)
```

DNA from the libraries was screened by PCR amplification, as per Ausube,l et al., *Current Protocols in Molecular Biology* (1995), with the PCR primer pair. A strong PCR product was identified in all libraries analyzed (fetal lung, fetal kidney, and placenta).

To isolate a cDNA clone encoding this protein, a human fetal lung-pRK5 vector library was selected and enriched for positive cDNA clones by extension of single stranded DNA from plasmid libraries grown in dug-/bung-host using the newa3.R primer. RNA for construction of the cDNA libraries was isolated from human fetal lung tissue. The cDNA library used to isolated the cDNA clones was constructed by standard methods using commercially available reagents (e.g., Invitrogen, San Diego, Calif.; Clontech, etc.). The cDNA was primed with oligo dT containing a NotI site, linked with blunt to SalI hemikinased adaptors, cleaved with NotI, sized appropriately by gel electrophoresis, and cloned in a defined orientation into a suitable cloning vector (pRKB or pRKD; pRK5B is a precursor of pRK5D that does not contain the SfiI site; see, Holmes, et al., *Science,* 253:1278-1280 (1991)) in the unique XhoI and NotI sites. To enrich for positive cDNA clones the primer extension reaction contained 10 μl of 10× PCR Buffer (Perkin Elmer, USA), 1 μl dNTP (20 mM), 1 μl library DNA (200 ng), 1 μl primer, 86.5 μl H2O and 1 μl of Amplitaq (Perkin Elmer, USA) added after a hot start. The reaction was denatured for 1 minute at 95° C., annealed for 1 minute at 60° C., and then extended for 15 minutes at 72° C. The DNA was extracted with phenol/chloroform, precipitated with ethanol, and then transformed by electroporation into a DH10B host bacteria. The entire transformation mixture was plated onto 10 plates and colonies were allowed to form. Colonies were lifted onto nylon membranes and screened with an oligonucleotide probe (newa3.probe: 5' TCT CGC AGC CGG AGA CCC CCT TCC CAC AGA AAG CCG ACT CA 3' (SEQ ID NO: 13)) derived from the Incyte EST. Filters were hybridized with the probe overnight at 42° C. in 50% formamide, 5×SSC, 10× Denhardt's, 0.05M sodium phosphate (pH 6.5), 0.1% sodium pyrophosphate, and 50 μg/ml ofsonicated salmon sperm DNA. Filters were then rinsed in 2×SSC, washed in 0.1×SSC, 0.1% SDS, and then exposed overnight to Kodak X Ray films. Five positive clones were identified. Pure positive clones were obtained after colony purification and secondary screening.

Two of the isolated clones were sequenced. These cDNA sequences were designated DNA48613 (SEQ ID NO: 14) and DNA48614 (SEQ ID NO: 16). Amino acid sequence analysis of DNA48613 revealed a 400 amino acid long open reading frame sequence (SEQ ID NO: 15) with a predicted 26 amino acid long N-terminal signal peptide. The predicted mature protein is 374 amino acids long, with a calculated molecular weight of approximately 41 kDa. Potential N-linked glycosylation sites are similar to hose in the mouse sequence. The mouse and human GFRα3 protein sequences are compared in FIG. 3.

The deduced amino acid sequence (SEQ ID NO: 17) of DNA48614 and comparison to SEQ ID NO: 15, revealed it to be an alternatively spliced form of DNA48613, with a 30 amino acid deletion (amino acid positions 127-157, counting from the initiation methionine), as shown in FIG. 4. Interestingly, none of the cysteines are deleted in this clone. Clones DNA48613 and DNA48614 have been deposited with ATCC and are assigned ATCC deposit nos. 209752 (Designation: DNA48613-1268) and 209751 (Designation: DNA48614-1268), respectively. A comparison of the nucleic acid sequences encoding DNA48613 with those encoding human GFR.alpha.1 and GFR.alpha.2 is provided in FIGS. 5A-B. The 5' untranslated GFR.alpha.3 sequence immediately upstream of the initiation ATG in the cloned DNA48613 is

```
                                  (SEQ ID NO 21)
GCGAGGGGAGCGCGGAGCCCGGCGCCTACAGCTCGCC.
```

As discussed below, a sequence comparison of the protein encoded by DNA48613 to GFRα1 and GFRα2 (FIG. 6) indicated that the two human proteins are new members of the GFRα receptor family, and are human homologs of murine GFRα3. Accordingly, DNA48613 encodes a protein designated human GFRα3, and DNA48614 encodes its splice variant.

Amino acid sequence comparisons between GFRα family members are provided in Table 1, based on a BLAST-2 and FastA sequence alignment analysis of the full-length sequence.

TABLE 1

Sequence Identity Between Members of the GFRα Family

| Proteins Compared | Percent Identity |
|---|---|
| rGFRα1 versus hGFRα1 | 92% |
| rGFRα2 versus hGFRα2 | 94% |
| mGFRα3 versus hGFRα3 | 77% |
| hGFRα3 versus hGFRα1 | 34% |
| hGFRα3 versus hGFRα2 | 34% |
| hGFRα1 versus hGFRα2 | 48% |

From the sequence comparisons it can be seen that human GFRα3 is less related to its rodent homologue than is either GFRα1 or GFRα2. In addition, GFRα3 appears to be more distantly related to GFRα1 and GFRα2 then GFRα1 and GFRα2 are to each other.

Example 3

Use of GFRα3 as a Hybridization Probe

The following method describes use of a nucleotide sequence encoding GFRα3 as a hybridization probe.

DNA comprising the coding sequence of GFRα3 (shown in SEQ ID NO: 4, SEQ ID NO: 14 or SEQ ID NO: 16), or a fragment thereof, is employed as a probe to screen for homologous DNAs (such as those encoding naturally-occurring GFRα3 or variants of GFRα3 ) in human tissue cDNA libraries, human tissue genomic libraries, RNA isolated from tissues, tissue preparations in situ, or chromosome preparations (such as for chromosome mapping).

Hybridization and washing of filters containing either library DNAs is performed under the following high stringency conditions. Hybridization of radiolabeled GFRα3-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence GFRα3 can then be identified using standard techniques known in the art.

Example 4

Northern Blot Analysis

Expression of GFRα3 mRNA in human tissues was examined by Northern blot analysis. Multiple human tissue RNA blots were hybridized to a $^{32}P$-labelled DNA probe encompassing the entire coding region of human GFRα3 cDNA labelled by random priming. Human fetal RNA blot MTN (Clontech, Inc. USA) and human adult RNA blots MTN-1 and MTN-II (Clontech) were incubated with the DNA probe. Blots were incubated with 1x10e6 cpm/ml probe in hybridization buffer (5×SSC; 10× Denhardt's solution; 0.05M sodium phosphate pH 6.5, 50 μg/mL sonicated salmon sperm DNA; 50% formamide; 0.1% sodium pyrophosphate) for 42° C. overnight. The blots were washed in 2×SSC at room temperature for 10 minutes followed by 0.2×SSC in 0.1% SDS at 42° C. for 30 minutes. The blots were exposed to x-ray film and developed after overnight exposure by phosphorimager analysis (Fuji).

Figure 7:
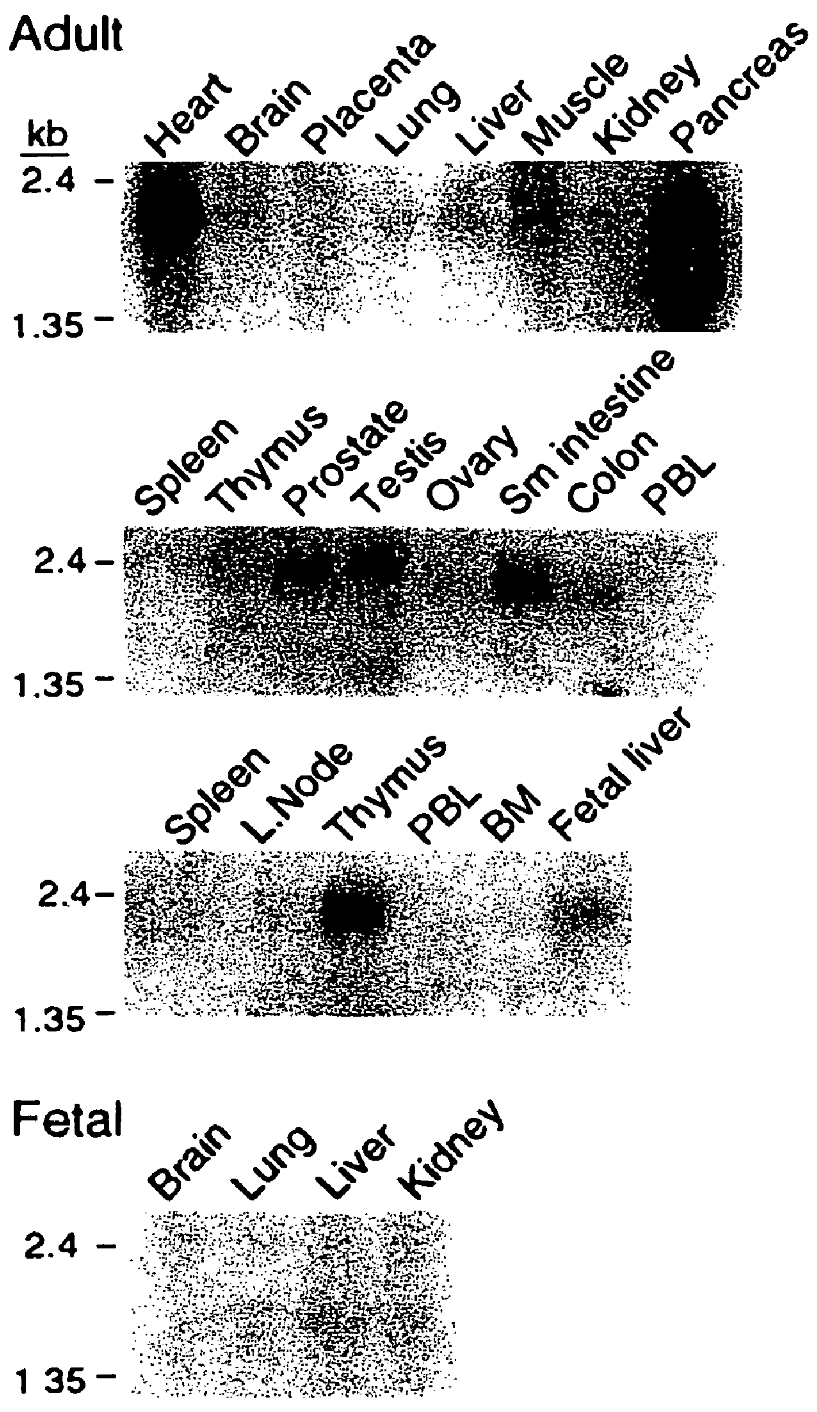
FIG. 7 presents multiple tissue Northern blots using GFRα3 as a probe.

As shown in FIG. 7 GFRα3 mRNA transcripts were detected. Expression was observed at high levels in the heart, gut (pancreas, small intestine, colon), thymus, testis and prostate.

Example 5

Localization of GFRα3 by In Situ Hybridization

The following tissues were surveyed for expression of GFRα3 mRNA by in situ hybridization: day 13 mouse embryo, day 15 and day 17 embryonic mouse brain, postnatal day 1 mouse brain, adult mouse brain (with optic nerve), adult mouse spinal cord, adult mouse trigeminal ganglion and roots, adult mouse retina, and embryonic utricle of several stages.

For in-situ hybridization, E13.5 mouse embryos were immersion-fixed overnight at 4° C. in 4% paraformaldehyde, cryoprotected overnight in 15% sucrose, embedded in O.T.C., and frozen on liquid nitrogen. Adult mouse spinal cord, trigeminal ganglia, retina, and P1 mouse brains were embedded in O.T.C. and fresh frozen on liquid nitrogen. Adult mouse brains were fresh frozen with powdered dry ice. Sections were cut at 16 um, and processed for in-situ hybridization for GFRα3 by a method described previously (Phillips, et al., *Science* 250:290 (1990)). Using 33P-UTP, labeled RNA probes were generated as described (Melton, et al., *Nucleic Acids Res.* 12:7035 (1984) using T7 polymerase with a 326 bp fragment encoding mouse GFRα3.

In the E13 mouse, GFRα3 mRNA was very strongly expressed in dorsal root ganglia, in sympathetic ganglia, and in peripheral nerves. The vestibular ganglion also displayed strong signal. Moderate expression was seen in whisker pads, in the region of the axilla, and surrounding the urinary bladder. Moderate expression was also seen in the intermediolateral region of the gray matter of the thoracic spinal cord, the ventromedial hypothalamus, and cell clusters in the dorsal hindbrain. Most other regions of the brain were devoid of demonstrable signal. Many other organs expressed either weak or undetectable signal, including lung, heart, liver, gut, and kidney.

At later developmental stages (E15, E17, P1, adult), GFRα3 expression within the CNS was very limited. Most regions of brain and spinal cord demonstrated no hybridization signal above the background level seen in control sections hybridized with sense strand control probe. Exceptions to this were cell clusters found in the hindbrain. In the adult, a subpopulation of trigeminal ganglion neurons was very strongly labeled, while no labeling was seen in either satellite cells or in the nerve roots. The optic nerve also failed to demonstrate detectable signal.

In sections of adult mouse heart, therer was diffuse signal over atrial and ventricular myocytes with focal areas of increased signal associated with the cardiac conduction system.

Figure 8:
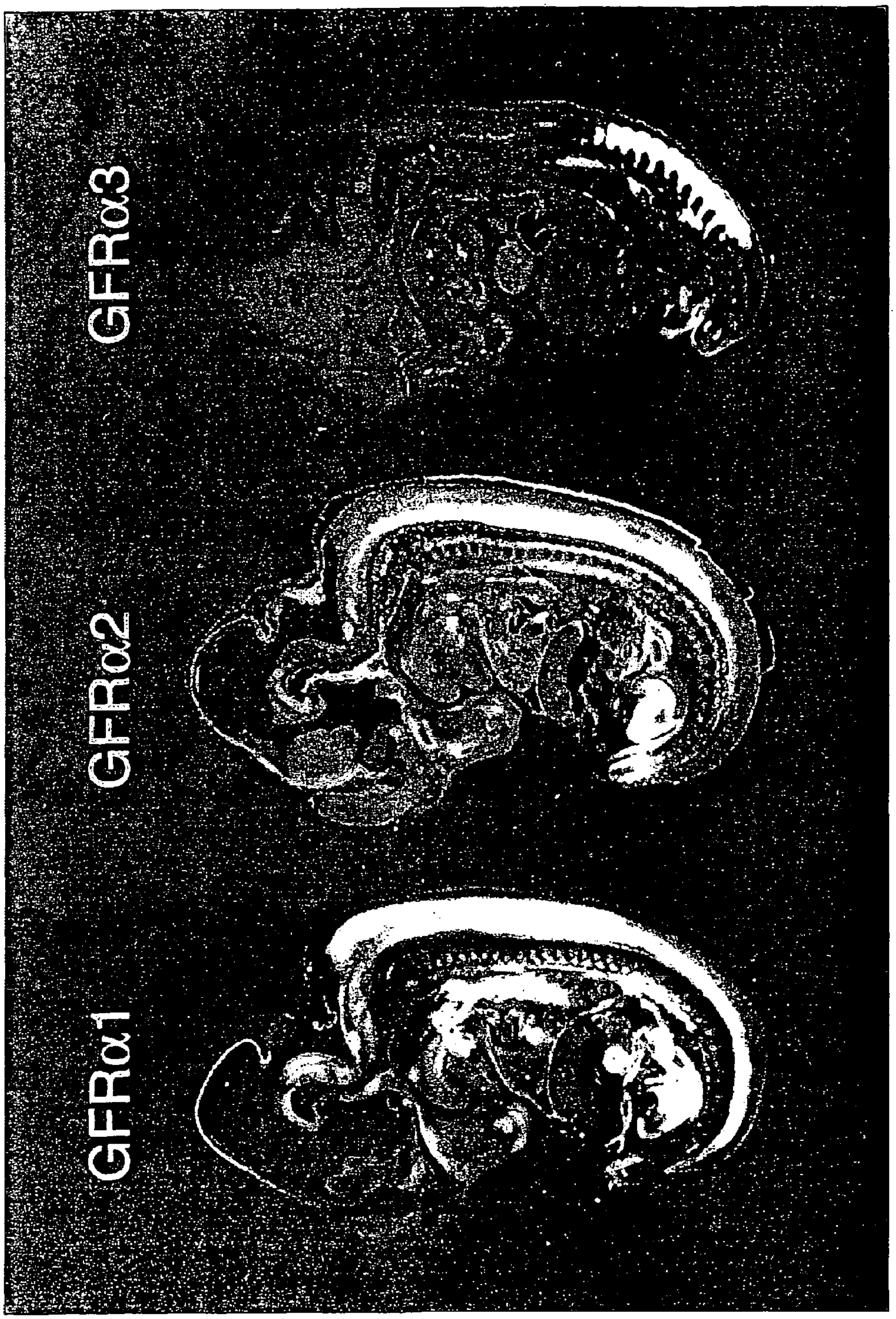
FIG. 8 compares RNA expression localization determined by in situ hybridization using DNA probes specific for GFRα1, GFRα2 and GFRα3.

A comparison of labeling with GFRα1, GFRα2 and GFRα3 is shown in FIG. 8. The expression of GFRα3 is very limited and localized in comparison to the other receptors.

Primers containing sense sequence GCCCGCGACCTCCACTGCTG (designated gfrp1; SEQ ID NO: 22) and antisense sequence CTGTGGGGAGCGGCGGCG (designated gfrp2.r.c; SEQ ID NO: 23) were used to generate a 671 bp hybridization probe from the mouse GFRα3. Primers containing sense sequence CCTGAACCTATGGTAACTGG (SEQ ID NO: 24) and antisense sequence ACCCAGTCCTCCCTACC (SEQ ID NO: 25) were used to generate a 378 bp hybridization probe from the mouse GFRα3.

Human fetal tissues at E12-E16 weeks that were examined included placenta, umbilical cord, liver, kidney, adrenals, thyroid, lungs, heart, great vessels, esophagus, stomach, small intestine, spleen, thymus, pancreas, brain, spinal cord, body wall, pelvis and lower limb. Adult tissues examined included kidney (normal and endstage), adrenal, myocardium, aorta, lung, skin, eye (including retina), bladder, liver (normal, cirrhotic, and acute failure), renal carcinoma, and soft tissue sarcoma. Non-human primate tissues examined included chimpanzee salivary gland, stomach, thyroid, parathyroid, skin and thymus. Hybridization to the 378 base pair antisense strand probe was detected in fetal and adult human DRG's, peripheral nerves (as seen in the body wall and lower limb of the fetus) and mesenteric nerves in the fetus. No expression was observed in the fetal spinal cord or brain. No expression was observed in the neuroblastomas examined.

Using the 671 base pair antisense probe, GFRα3 mRNA hybridization was detected in the early and late and adult rat in E14 ganglion, trigeminal, peripheral nerves of skin and skeletal muscle: E17 skin, dorsal root ganglion, peripheral nerves, cartilage, skeletal muscle, and brain; E19 dorsal root ganglion, peripheral nerves, brain, stratum corneum of skin, tooth, skeletal muscle, cartilage, liver and gut. No specific signal was detected in fetal or adult rat pancreas. In all the examples in this section, the corresponding sense probes failed to hybridize as might be expected.

Example 6

Expression of GFRα3 in *E. coli*

The DNA sequence encoding GFRα3, e.g. human GFRα3, is initially amplified using selected PCR primers. The primers should contain restriction enzyme sites that correspond to the restriction enzyme sites on the selected expression vector. A variety of expression vectors may be employed. An example of a suitable vector is pBR322 (derived from *E. coli*; see Bolivar, et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences that encode for an antibiotic resistance gene, a trp promoter, a polyhis leader (including the first six STII codons, polyhis sequence, and enterokinase cleavage site), the mammalian GFRα3 coding region, lambda transcriptional terminator, and an argU gene.

The ligation mixture is then used to transform a selected *E. coli* strain using the methods described in Sambrook, et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized mammalian GFRα3 protein can then be purified using a metal chelating column under conditions that allow tight binding of the protein.

Example 7

Expression of GFRα3 in Mammalian Cells

This example illustrates preparation of a glycosylated form of mammalian GFRα3 by recombinant expression in mammalian cells.

The vector, pRK5 (see EP 307,247, published Mar. 15, 1989), is employed as the expression vector. Optionally, the GFRα3 DNA is ligated into pRK5 with selected restriction enzymes to allow insertion of the GFRα3 DNA using ligation methods such as described in Sambrook et al., supra. The resulting vector is called pRK5-GFRα3.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-GFRα3 DNA is mixed with about 1 μg DNA encoding the VA RNA gene (Thimmappaya, et al., *Cell,* 31:543 (1982)) and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of mammalian GFRα3 polypeptide. The cultures containing transfected cells may undergo further incubation (in serum free medium) and the medium is tested in selected bioassays.

In an alternative technique, mammalian GFRα3 may be introduced into 293 cells transiently using the dextran sulfate method described by Somparyrac Sompayrac et al., *Proc. Natl. Acad. Sci.,* 12 78:7575 (1981). 293 cells are grown to maximal density in a spinner flask and 700 μg pRK5-GFRα3 DNA is added. The cells are first concentrated from the spinner flask by centrifugation and washed with PBS. The DNA-dextran precipitate is incubated on the cell pellet for four hours. The cells are treated with 20% glycerol for 90 second, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed mammalian GFRα3 can then be concentrated and purified by any selected method, such as dialysis and/or column chromatography.

In another embodiment, mammalian GFRα3 can be expressed in CHO cells. The pSUi-GFRα3 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of mammalian GFRα3 polypeptide, the culture medium may be replaced with serum free medium. Preferably, the cultures are incubated for about 6 days, and then the conditioned medium is harvested. The medium containing the expressed mammalian GFRα3 can then be concentrated and purified by any selected method.

Epitope-tagged mammalian GFRα3 may also be expressed in host CHO cells. The mammalian GFRα3 may be subcloned out of the pRK5 vector. The subclone insert can undergo PCR to fuse in frame with a selected epitope tag such as a poly-his tag into an expression vector. The poly-his tagged mammalian GFRα3 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged mammalian GFRα3 can then be concentrated and purified by any selected method, such as by $Ni^{2+}$-chelate affinity chromatography.

Example 8

Expression of GFRα3 in Baculovirus-Infected Insect Cells

The following method describes recombinant expression of GFRα3 in Baculovirus-infected insect cells.

The GFRα3 was fused upstream of an epitope tag contained within a Baculovirus expression vector. Such epitope tags include poly-his tags and immunoglobulin tags (like Fc regions of IgG). The amino acid sequence of the GFRα3-IgG fusion is provided in SEQ ID NO: 18. A variety of plasmids may be employed, including plasmids derived from commercially available plasmids such as pVL1393 (Novagen). Briefly, GFRα3 sequence encoding the extracellular domain) was amplified by PCR with primers complementary to the 5' and 3' regions. The 5' primer incorporate flanking (selected) restriction enzyme sites. The product was then digested with those selected restriction enzymes and subcloned into the expression vector. The vector for expression of GFRα3-IgG in insect cells was pb.PH (where expression in Baculovirus was under control of the polyhedrin promoter).

Recombinant Baculovirus was generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses were harvested and used for further amplifications. Viral infection and protein expression was performed as described by O'Reiley et al., "Baculovirus expression vectors: A laboratory Manual," Oxford: Oxford University Press (1994). Purification of the IgG tagged (or Fc tagged) GFRα3 was performed using known chromatography techniques, including Protein A or protein G column chromatography Alternatively, expressed poly-his tagged GFRα3 can be purified by $Ni^{2+}$-chelate affinity chromatography as follows. Extracts are prepared from recombinant virus-infected Sf9 cells as described by Rupert Ruppert et al. *Nature* 362:175-179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 Fm filter. A $Ni^{2+}$-NTA agararose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to a baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged GFRα3 are pooled and dialyzed against loading buffer.

Example 9

Binding to GFRα3

Figure 9A:
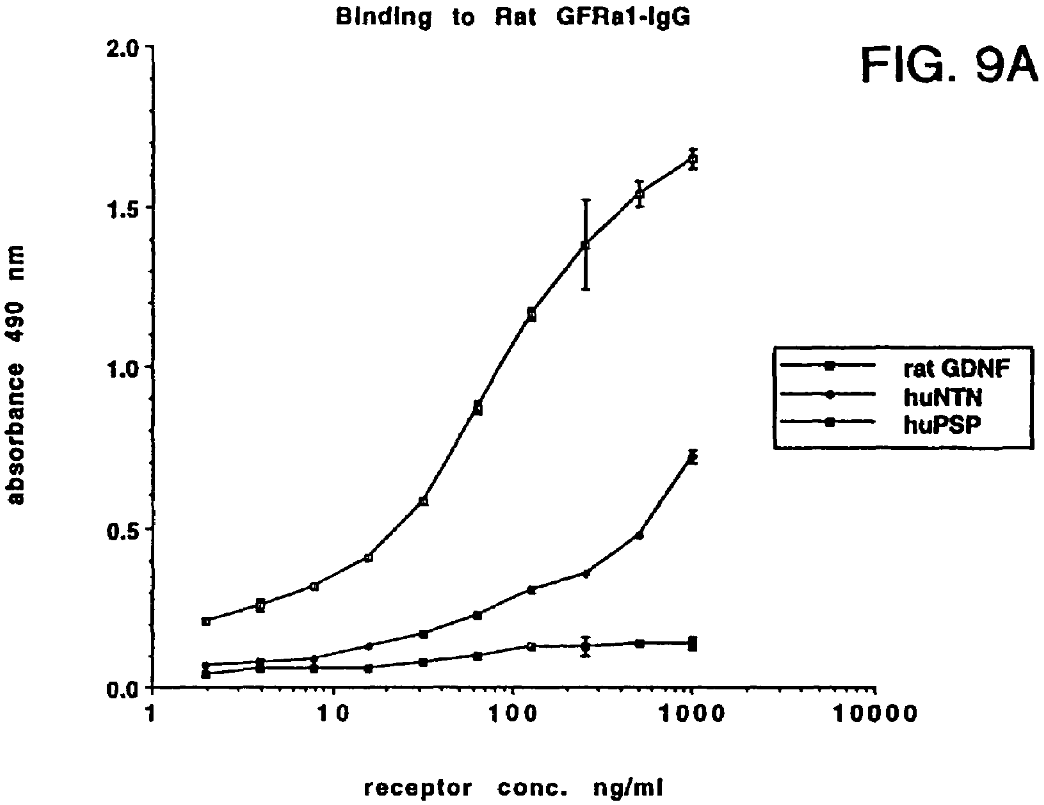
FIGS. 9A-C present the results of ligand binding (rat GDNF, human neurturin (NTN) or Human persephin (PSN)) to IgG-tagged receptors GFRα1 (FIG. 9A), GFRα2 (FIG. 9B) or GFRα3 (FIG. 9C).
Figure 9B:
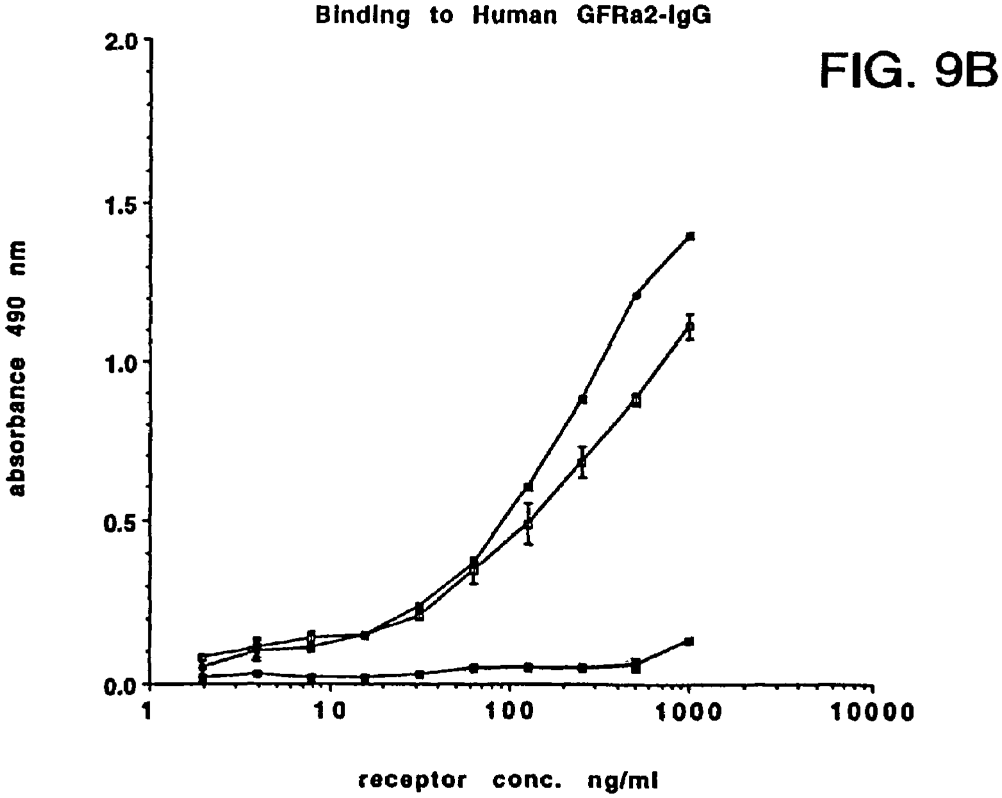

In order to determine if any of the known GDNF family members (ligands GDNF, Neurturin (NTN) or Persephin (PSN)) could bind to GFRα3, each ligand was coated onto microtiter plates and incubated with either GFRα1-IgG, GFRα2-IgG, or GFRα3-IgG (SEQ ID NO: 18) prepared as in Example 8. Binding of GFRα-IgG was then detected with a secondary antibody to its IgG portion. GDNF, NTN, and PSN were coated onto microtiter plates at 1 μg/ml in 50 mM carbonate buffer, pH 9.6, overnight at 4° C. The plates were then washed with PBS/0.05% Tween 20, then blocked with PBS/0.05% BSA/0.05% Tween 20 for 1-2 hours at room temperature. Various concentrations of IgG-tagged chimeric receptors (GFRα1-IgG, GFRα2-IgG, GFRα3-IgG; 1 μg/ml to 1.95 ng/ml) were added to each well and the plates were incubated for 1 hour at room temperature. The plates were then washed as described above and incubated in the presence of goat anti-human IgG(Fc)-HRP (1:1000) for 1 hour at room temperature. After washing, bound HRP was revealed with OPD substrate for 5 to 10 minutes, followed by reading the plates at 490 nm. The results are shown in FIGS. 9A-C.

Figure 9C:
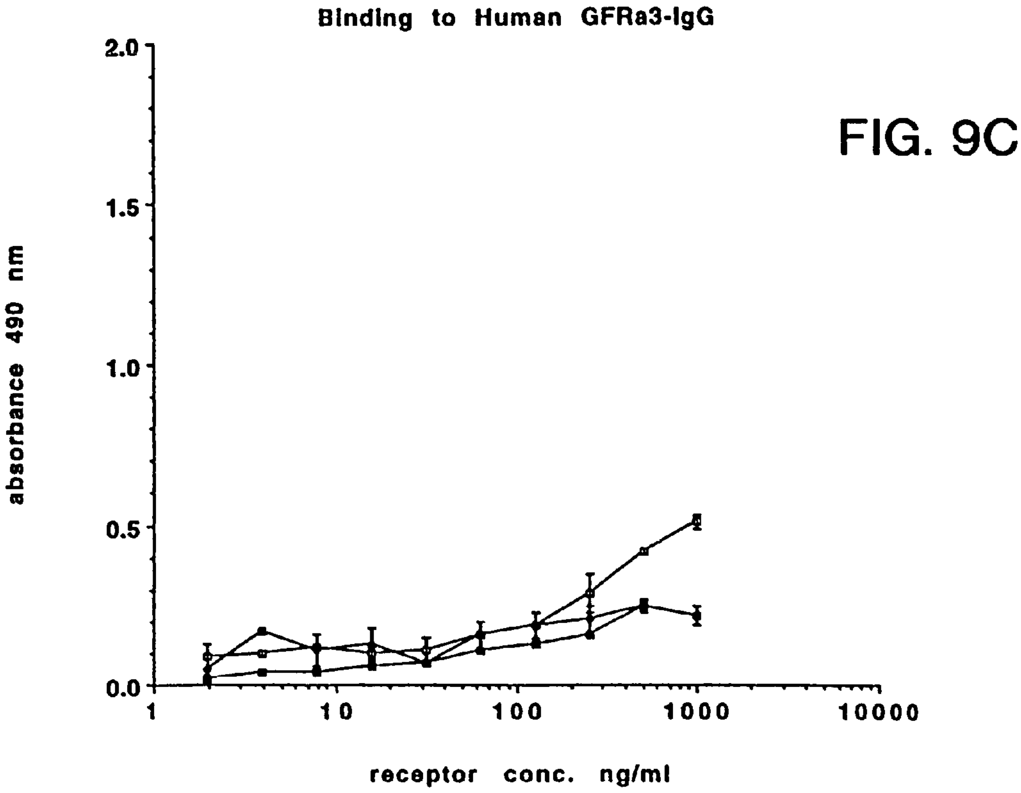

GFRα1 binds to GDNF (FIG. 9A), GFRα2 binds to GDNF and NTN (FIG. 9B), but GFRα3 does not bind any of these molecules (FIG. 9C). GFRα3 is thus an orphan receptor.

Example 10

Assays for GFRα3 Agonists

The GDNF family of ligands uses a unique receptor system: a GPI-linked ligand binding protein (α-component) and a signaling component, the tyrosine kinase receptor Ret. The mechanism of activation of this multicomponent receptor complex is still unknown, but tyrosine kinase receptors are known to be activated upon ligand-induced dimerization. Accordingly, a possible mechanism of GFR activation is by ligand binding to the α-component which induces α-component dimerization. The two α-chains in turn will bring two Ret molecules into the complex, which will lead to activation of the kinase domains and phosphorylation of target tyrosine residues on the receptor and/or on other signaling molecules.

To demonstrate that ligands do induce dimerization of the a-component, chimeric receptors made of the extracellular domain of the rat GFRα2 and the transmembrane and intracellular domain of the TPO receptor (c-mpl) or of the Rse tyrosine kinase receptor were constructed. These two receptors belong to different family of receptors but are both known to be activated by ligand induced dimerization or by agonist-antibody-induced dimerization.

Figure 10:
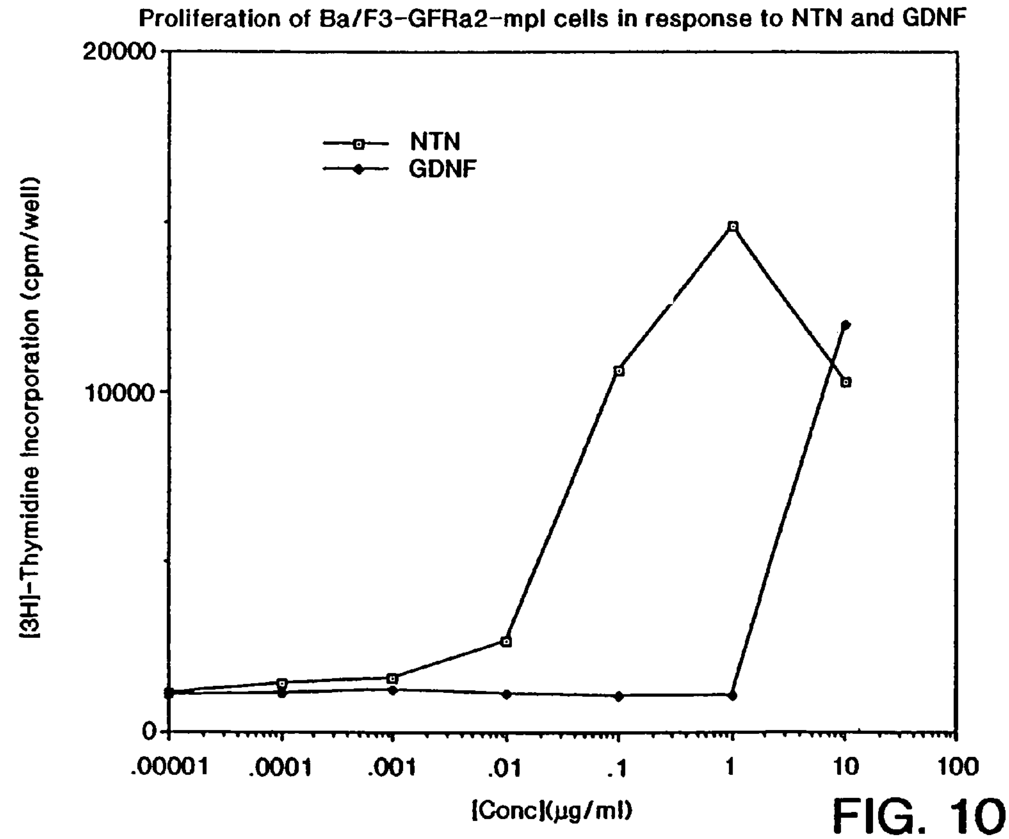
FIG. 10 presents the proliferation of cells expressing recombinant chimeric GFRα2-mpl in response to NTN or GDNF.

GFRα2-c-mpl. A chimeric receptor made of the gD epitope tag followed by the rGFRα2 extracellular domain (less the GPI signal) followed by the transmembrane and intracellular domain of the TPO receptor was assembled by recombinant PCR into the pRKtkneo vector under the control of the CMV promoter. Ba/F3 cells were electroporated with NotI linearized pRKtkneo-GFRα2-mpl, and clones were obtained by limiting dilutions. Individual clones were analyzed for expression of the receptor by FACS analysis using an anti-gD antibody. Positive clones were selected and further characterized for their capacity to proliferate in response to NTN stimulation, a ligand for GFRα2. As shown in FIG. 10, Ba/F3 cells expressing GFRα2-mpl are capable of proliferating in response to NTN stimulation, as assessed by 3H-thymidine incorporation.

Figure 11:
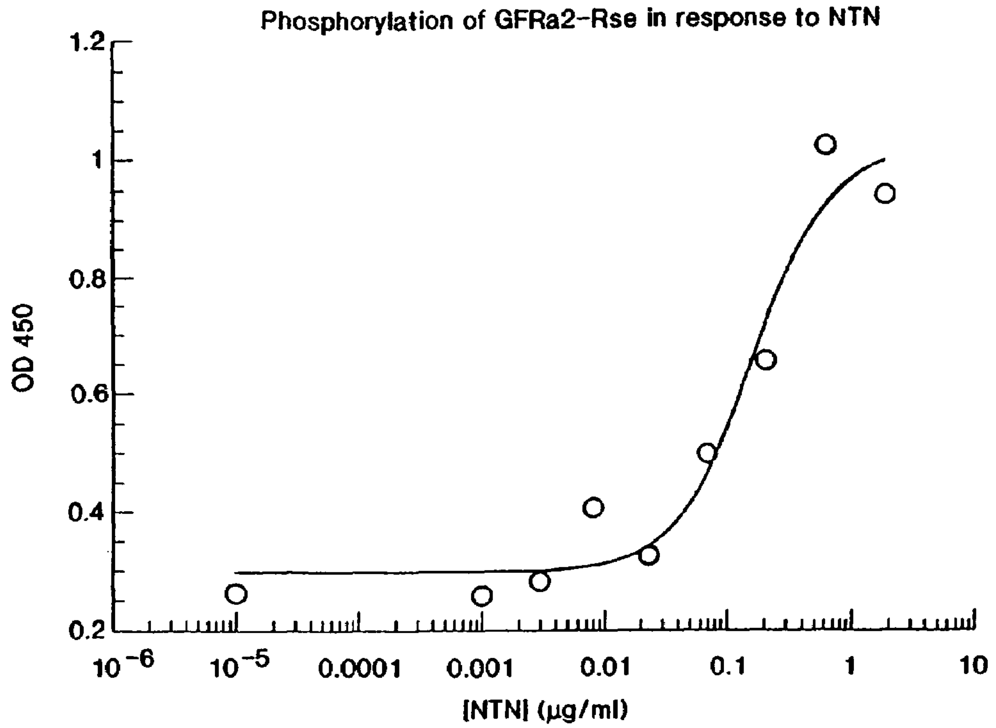
FIG. 11 presents the auto-phosphorylation of recombinantly expressed receptor GFRα2-Rse in response to NTN.

GFRα2-Rse. A chimeric receptor was constructed with the gD epitope tag followed by the rat GFRα2 extracellular domain (less the GPI signal) followed by the transmembrane and intracellular domain of the Rse tyrosine kinase receptor and another gD epitope tag and was assembled by recombinant PCR into a pSVi vector under the control of the SV40 promoter. The gD-GFRα2-Rse-gD sequence is presented in SEQ ID NO: 19. CHO cells were transfected by the lipofectamine method (GIBCO-BRL). Single transfected CHO clones were picked and analyzed for expression of the receptor by FACS analysis using an anti-gD antibody. Receptor-positive clones were then analyzed using a KIRA assay (e.g., U.S. Pat. No. 5,709,858) for receptor induced phosphorylation upon NTN stimulation. As shown in FIG. 11, NTN stimulation caused autophosphorylation of the receptor.

Figure 12:
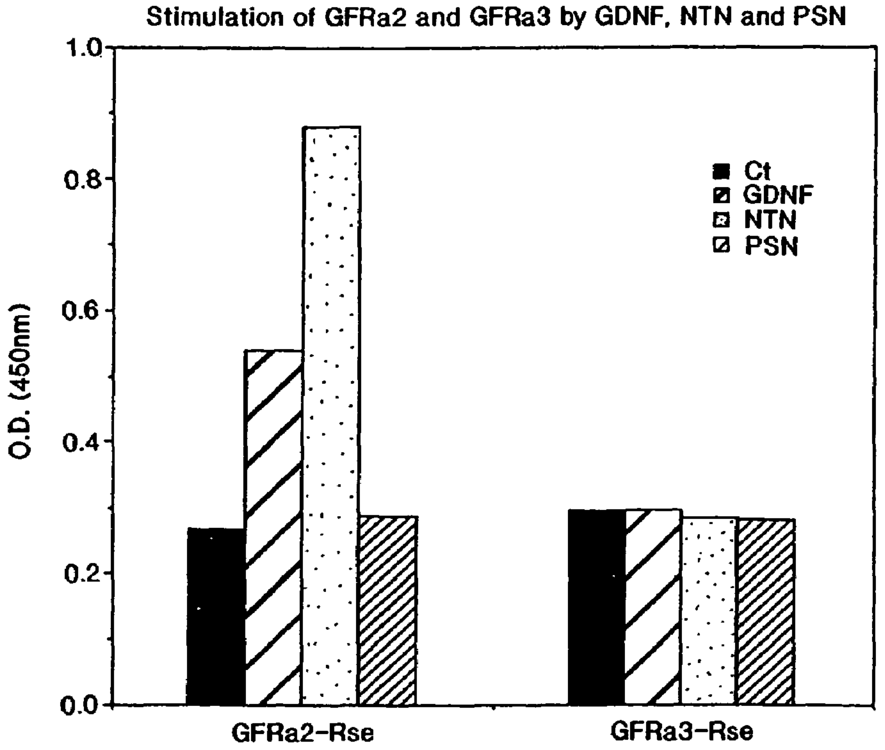
FIG. 12 presents the assay for stimulation of receptors GFRα2 or GFRα3 by GDNF, NTN or PSN.

GFRα3-Rse. Together, the above data indicate that activation of the GFRs is mediated by ligand-induced dimerization and that, in addition to their ligands, the various receptors will be susceptible to antibody-mediated activation. Accordingly, in one embodiment, an assay to identify agonist antibodies and a natural ligand (or other agonists) for mammalian GFRα3 follows the method described above for GFRα2-Rse. A chimeric GFRα3 receptor was constructed with the gD epitope tag followed by the murine GFRα3 extracellular domain (less the GPI signal; preferably the human GFRα3 is used) followed by the transmembrane and intracellular domain of the Rse tyrosine kinase receptor and a second gD tag using recombinant PCR into the pSVi vector under the control of the SV40 promoter. CHO cells were transfected by the lipofectamine method (GIBCO-BRL). Single transfected clones were picked and analyzed for expression of the GFRα3 chimeric receptor by FACS analysis using an anti-gD antibody. Positive clones were then analyzed for receptor induced phosphorylation upon treatment with either GDNF, NTN or PSN. The results are shown in FIG. 12. The results confirmed that GFRα3 is a receptor for a novel ligand of the GDNF family. The sequence of gD-GFRα3-Rse-gD is presented in SEQ ID NO: 20. As is evident from this construct sequence and its homology to the other GFR family members, a sufficient ligand binding region is from amino acid 110 to amino acid 386 of SEQ ID NO: 20, which corresponds to amino acid residues 84 to 360 in SEQ ID NO: 15. The natural ligand for GFRα3 has been identified as artemin (Baloh, et al., Neuron 21:1291-1302 (1998), which has been found to bind the GFRα3 of the present invention and its gD-GFRα3-Rse-gD fusion. Antibodies generated against GFRα3 (or other candidate agonists) can be screened for agonist activity using the GFRα3 construct expressed in CHO cells. Alternatively, antagonists are screened by their ability to inhibit agonist function in this assay.

Example 11

Preparation of Antibodies that Bind GFRα3

This example illustrates preparation of monoclonal antibodies which can specifically bind GFRα3. Techniques for producing the monoclonal antibodies are known in the art and are described, for instance, in Goding, supra. Immunogens that may be employed include purified GFRα3, fusion proteins containing GFRα3, and cells expressing recombinant GFRα3 on the cell surface. Selection of the immunogen can be made by the skilled artisan without undue experimentation. Mice, such as Balb/c, are immunized with the GFRα3 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect GFRα3 antibodies.

After a suitable antibody titer has been detected, the animals "positive" for antibodies can be injected with a final intravenous injection of GFRα3. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against GFRα3. Determination of "positive" hybridoma cells secreting the desired monoclonal antibodies against GFRα3 is within the skill in the art. The positive hybridoma cells can be injected intraperitoneally into syngeneic Balb/c mice to produce ascites containing the anti-GFRα3 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 12

Dimerization Screening Assays

Candidate agonists, for example antibodies generated against the α-subunit receptor of the GFR family, e.g. GFRα3, GFRα2, or GFRα1, can be screened for agonist activity using the appropriate α-receptor-Rse-like construct expressed in CHO cells or other suitable cells in a KIRA assay. An exemplary KIRA protocol using monoclonal antibodies to the gD portion of the gD-GFRα2-Rse construct is presented.

CHO cell culture expressing the gD-GFRα2-Rse fusion protein were prepared and cultured as follows. On Day 1 the transfected CHO cells from culture flask are preferably 70-90% confluent with very few floating (detached) cells. Culture plates were Falcon (1270) flat bottom, 96-well sterile tissue culture plates with cover. The Detachment Buffer was PBS with 1:50 diluted 5 mMEDTA (250 mM stock). The Cell Culture Media was Ham's F-12 without GHT, low Glucose DMEM without Glycine: with NaHCO3 (50:50)+10% Diafiltered FBS, 25 mM HEPES, 2 mM L-Glutamine. On Day 2 the Stimulation Media was Excell-401 insect cell media (JRH Biosciences cat#14401-78p) plus 0.5% BSA. The Lysis Buffer was 150 mM NaCl with 50 mM HEPES and 0.5% Triton-X 100. Protease inhibitors added to lysis buffer before use were 100× AEBSF (100 mM) stockusing 1:100 dilution, 1000× Aprotinin (liquid) stock using 1:1000 dilution, and 1000× Leupeptin (50 mM) stock using 1:1000 dilution. Phosphatase inhibitor added to lysis buffer before use was 50× Sodium Orthovanidate (100 mM) stock using 1:50 dilution.

The ELISA format used the following materials. Solid support was Nunc Maxisorp immunoplate 4-39454. Coating buffer was PBS pH 7.4. Washing Buffer was PBS with 0.05% tween 20 pH 7.4. Blocking Buffer was PBS with 0.5% BSA. Assay Buffer was PBS with 0.5% BSA, 0.05% Tween 20 and 5 mM EDTA, pH 7.4. Substrate was a TMB substrate kit (2 bottles: A: TMB substrate; B: TMB peroxide solution) from Kirkegard and Perry. Stopping Solution was 1.0 M H3PO4. Antigen was solublized transfected "Receptor.gD" from cell culture wells (cell lysate). Antibodies were (1°) 3C8 (anti-gD peptide) concentration 1.0 µg/ml, 1:1300 dil 1.3 mg/ml stock, lot 24564-7 #1766, (2°) Biotinylated 4G10 (UBI) concentration 1:1000 from 4° C. stock (50 µg/ml) #100796. Conjugate was Streptavidin/HRP Zymed concentration 1:50000 lot #26246-91 (1:100 frozen stock ).

Cells were harvested by aspirating cell culture supernantent from tissue culture flask, rinsed once with sterile PBS, and 10 ml of the cell detachment buffer was added. The cells were incubated at 37° C. for ~10 min until cells detached. Detached cells were transferred to a centrifuge tube and an equal volume of cell culture medium was added. Count cells were done with a hemocytometer. Cells were centrifuged, supernantent was removed by aspiration, and cells were suspended to 1×106 cells/ml. Added to each well was 100 µl cell suspension (final of about 1×105 cells/well). Plates were incubated at 37° C. overnight.

Receptor activation was porformed as follows. Typically, a stock of ligand, in this example a 2 mg/ml preparation of hNTNFP was used to make a final concentartion of NTN in each well as 0.1, 0.05, 0.025, 0.0125, 0.00625, 0.00312, 0.001, and 0.0 ug/ml. Solutions in microtiter plates were gently mixed by external shaking. A 100 µl of sample, control or NSB was added to each well and incubated for 25 minutes at 37° C. Gentle mixing of the plates was done. To each well was added 130 µl Lysis Buffer with protease and phosphotase inhibitors. Cell lysis was allowed to proceed for 30 minutes in the tissue culture plates. For storage the cell lysates were placed at −70° C.

An ELISA was run as follows. To coat the ELISA plates, 100 ul of 1° mAb (primary; 3C8 1 µg/ml) solution was added to each well, and allowed to coat the wells at 4° C. overnight. To perform the assay in Capture (ELISA) plates, the coat solution was discarded and 150 ul of blocking buffer was added to each well. Blocking was allowed to continue for 1 hour. Cell lysates were thawed with gentle agitation. The ELISA plates were rinsed with wash buffer three times (using a Skatron ScanWasher 300). To each capture ELISA plate well, 100 µl cell lysate was transferred using a fresh pipette tips for each transfer. Plates were incubated at room temperature for 2 hours with gentle agitation. Dilute biotinylated 4G10(2° Ab; secondary antibody; 4° C.) 1:1000 in assay buffer was prepared. Each well was rinsed 10 times with wash buffer. To each well was added 100 ul of 2° Ab, followed by incubation at room temperature for 2 hours with gentle agitation. Plates were washed with wash buffer six times. Dilute Streptavidin/HRP 1:50000 in assay buffer was prepared. To each well was added 100 µl diluted StrAv/HRP, followed by incubation at room temperature for 1 hour with gentle agitation. Plates were washed with wash buffer six times. To each well was added 100 ul of substrate solution: 1 volume of K&P TMB substrate plus 1 volume of K&P TMB peroxide solution.

Figure 13:
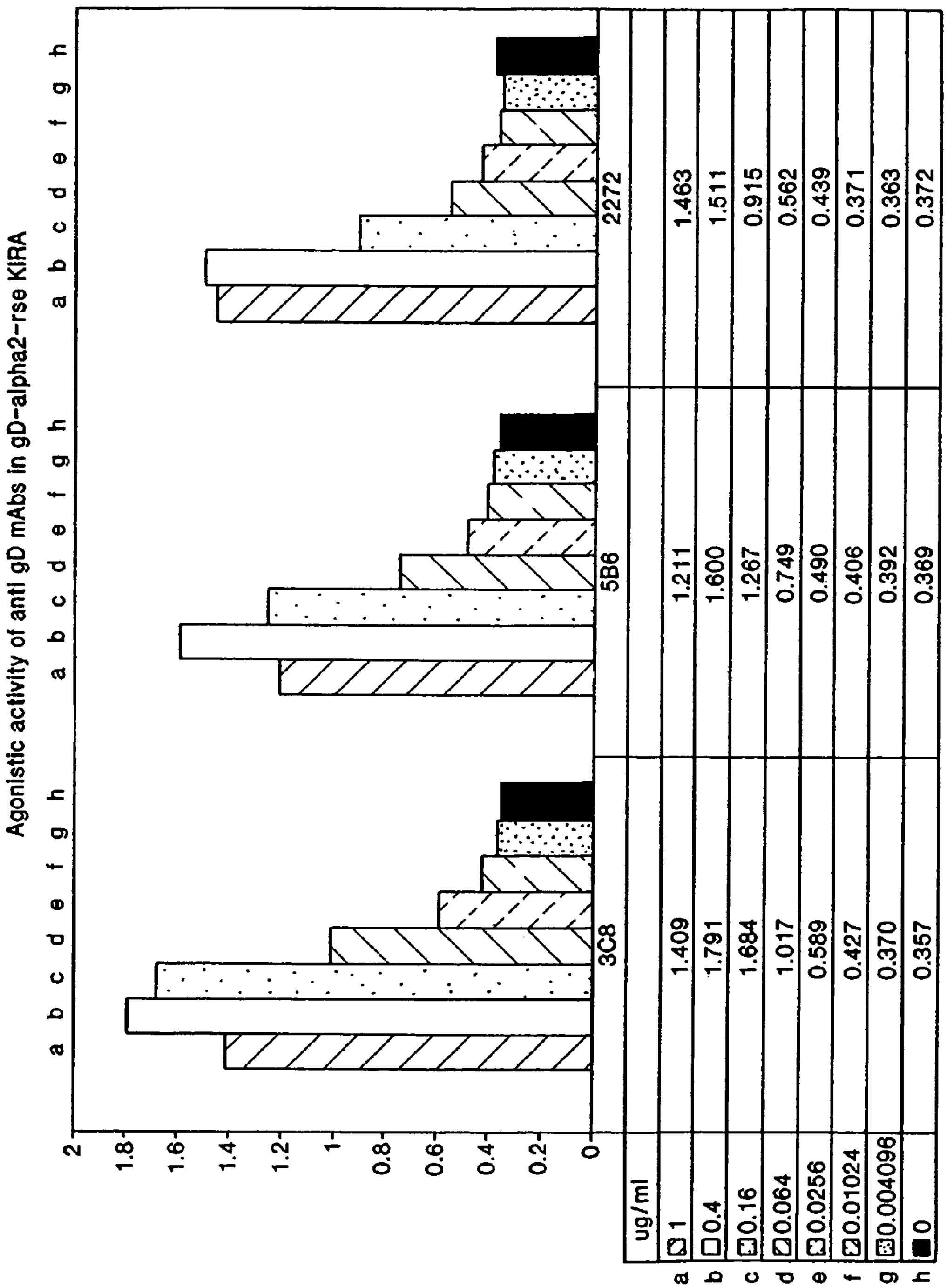
FIG. 13 depicts the agonist activity of various anti-gD antibodies in a gD-GFRα-2-Rse KIRA assay.

The reaction color was allowed to develop for 15 minutes, followed by an addition of 50 ul of 1.0 M H3PO4 to quench the color development. The O.D. (450 nm) mof each well was read. FIG. 13 shows the activation results using three different agonist antibodies—in this case the antibodies were raised against the gD flrag epitope, but were able to induce α-subunit oligomerization and subsequent tyrosine kinase domain (Rse region) activation.

Deposit of Material

The following materials have been deposited with the American Type Culture Collection, 12301 Parklawn Drive, Rockville, Md., USA (ATCC):

| Material | ATCC Dep. No. | Deposit Date |
|---|---|---|
| DNA48613 | 209752 | Apr. 7, 1998 |
| DNA48614 | 209751 | Apr. 7, 1998 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated polypeptide comprising the amino acid sequence SEQ ID NO: 17.

2. The polypeptide of claim 1, comprising a polypeptide of SEQ ID NO: 17 fused with the transmembrane domain and intracellular domain of the Rse tyrosine kinase receptor that is effective to activate phosphorylation by said Rse tyrosine kinase receptor upon ligand-induced dimerization.

3. An isolated polypeptide comprising amino acids 84 to 329 of SEQ ID NO: 17.

4. The polypeptide of claim 3, comprising a polypeptide comprising amino acids 84 to 329 of SEQ ID NO: 17 fused with the transmembrane domain and intracellular domain of the Rse tyrosine kinase receptor that is effective to activate phosphorylation by said Rse tyrosine kinase receptor upon ligand-induced dimerization.

5. An isolated polypeptide comprising amino acids 27 to 369 of SEQ ID NO: 17.

6. The polypeptide of claim 5, comprising a polypeptide comprising amino acids 84 to 329 of SEQ ID NO: 17 fused with the transmembrane domain and intracellular domain of the Rse tyrosine kinase receptor that is effective to activate phosphorylation by said Rse tyrosine kinase receptor upon ligand-induced dimerization.

7. An isolated polypeptide comprising an α-subunit receptor ligand-binding domain comprising amino acids 84 to 329 of SEQ ID NO: 17, a flag polypeptide, and an intracellular catalytic domain of a tyrosine kinase receptor.

8. The polypeptide of claim 7, wherein the flag polypeptide comprises the gD flag epitope.

9. The polypeptide of claim 7, wherein the tyrosine kinase receptor is a Rse receptor.

10. The polypeptide of claim 9 further comprising the transmembrane domain of the Rse receptor.

11. The polypeptide of claim 10, wherein the α-subunit receptor is a GFRα receptor comprising amino acids 27 to 369 of SEQ ID NO: 17.

* * * * *

SEQUENCE LISTING

<160> NUMBER OF SEQ ID NOS: 25

<210> SEQ ID NO 1
<211> LENGTH: 387
<212> TYPE: DNA
<213> ORGANISM: Mus musculus

<400> SEQUENCE: 1
ctgatttgca gcctgtggtg ggagagaact cgccagcctg tggaagaaga cgcagcgcgc 60
tacacagcaa cccggaacca accaggcatt ccgcagcaca tcccgtctgc tccagaagag 120
gtcttagaag tgagggctgt gacccttccg atcctgagcg gctagttttc aaacctccct 180
tgcccctgct tccttctggc tcaggctgct cctccttagg actttgtggg tccagttttg 240
ccttctgttc tgatggtgat tagcggctca cctccagcgc ttcttcctgt ttcccaggac 300
cacccagagg ctaaggaatc agtcattccc tgttgccttc tccaggaagg caggctaagg 360
gttctgaggt gactgagaaa aatgttt 387

<210> SEQ ID NO 2
<211> LENGTH: 353
<212> TYPE: DNA
<213> ORGANISM: Mus musculus

<400> SEQUENCE: 2
cgcggcgccc agcgaggcag agcgctgtcg catcccgggc gtccacccgc catggggctc 60
tcctggagcc cgcgacctcc actgctgatg atcctgctac tggtgctgtc gttgtggctg 120
ccacttggag caggaaactc ccttgccaca gagaacaggt ttgtgaacag ctgtacccag 180
gccagaaaga aatgcgaggc taatcccgct tgcaaggctg cctaccagca cctgggctcc 240
tgcacctcca gttaagcagg ccgctgccct tagaggagtc tgccatgtct gcagactgcc 300
tagaggcagc agaacaactc aggaacagct ctctgataga ctgcaggtgc cat 353

<210> SEQ ID NO 3
<211> LENGTH: 498
<212> TYPE: DNA
<213> ORGANISM: Mus musculus

<400> SEQUENCE: 3
aattcggaac gagggtgaag gagcttcgca agtcccaagg ccctttggaa gtcgctgaag 60
ctgccgtcag ccaatccagt ggactcgcag ccaaatttgt catccactgt cacatccccc 120
agtgggactc cgacaaatgt gaagaacagc tggaagagac catcaaaaac tgcctgtctg 180
cagcagagga caagaagctt aaatccgtcg ccttcccacc gttccccagt ggcagaaact 240
gcttccccaa acagacggcc gcccaggtga ccctcaaggc catctcggct cacttcgacg 300
actcgagctc gtcctcgctg aagaatgtgt acttcctgct cttcgacagc gagacatcgg 360
catctacgtg caggagatgg ccaaactgga caccaagtag ctctctccag tggcggcgaa 420
ggaggaggat cggcgtgacg tcacaagagc gggggtttta ttttttacaa ggattgcaga 480
agggtgacgg ggcatggg 498

<210> SEQ ID NO 4
<211> LENGTH: 1935
<212> TYPE: DNA
<213> ORGANISM: Mus musculus

<400> SEQUENCE: 4

-continued

```
gaatttggcc ctcgaggcca agaattcggc acgaggcgcg gcgcccagcg caggcagagc     60
gctgtcgcat cccgggcgtc cacccgccat ggggctctcc tggagcccgc gacctccact    120
gctgatgatc ctgctactgg tgctgtcgtt gtggctgcca cttggagcag gaaactccct    180
tgccacagag aacaggtttg tgaacagctg tacccaggcc agaaagaaat gcgaggctaa    240
tcccgcttgc aaggctgcct accagcacct gggctcctgc acctccagtt taagcaggcc    300
gctgcccctta gaggagtctg ccatgtctgc agactgccta gaggcagcag aacaactcag    360
gaacagctct ctgatagact gcaggtgcca tcggcgcatg aagcaccaag ctacctgtct    420
ggacatttat tggaccgttc accctgcccg aagccttggt gactacgagt tggatgtctc    480
accctatgaa gacacagtga ccagcaaacc ctggaaaatg aatcttagca agttgaacat    540
gctcaaacca gactcggacc tctgcctcaa atttgctatg ctgtgtactc ttcacgacaa    600
gtgtgaccgc ctgcgcaagg cctacgggga ggcatgctca gggatccgct gccagcgcca    660
cctctgccta gcccagctgc gctccttctt tgagaaggca gcagagtccc acgctcaggg    720
tctgctgctg tgtccctgtg caccagaaga tgcgggctgt ggggagcggc ggcgtaacac    780
catcgccccc agttgcgccc tgccttctgt aacccccaat tgcctggatc tgcggagctt    840
ctgccgtgcg gaccctttgt gcagatcacg cctgatggac ttccagaccc actgtcatcc    900
tatggacatc cttgggactt gtgcaactga gcagtccaga tgtctgcggg catacctggg    960
gctgattggg actgccatga ccccaaactt catcagcaag gtcaacacta ctgttgcctt   1020
aagctgcacc tgccgaggca gcggcaacct acaggacgag tgtgaacagc tggaaaggtc   1080
cttctcccag aacccctgcc tcgtggaggc cattgcagct aagatgcgtt tccacagaca   1140
gctcttctcc caggactggg cagactctac tttttcagtg gtgcagcagc agaacagcaa   1200
ccctgctctg agactgcagc ccaggctacc cattctttct ttctccatcc ttcccttgat   1260
tctgctgcag accctctggt agctgggctt cctcagggtc ctttgtcctc tccaccacac   1320
ccagactgat ttgcagcctg tggtgggaga gaactcgcca gcctgtggaa gaagacgcag   1380
cgtgctacac agcaacccgg aaccaaccag gcattccgca gcacatcccg tctgctccag   1440
aagaggtctt agaagtgagg gctgtgaccc ttccgatcct gagcggctag ttttcaaacc   1500
tcccttgccc ctgcttcctt ctggctcagg ctgctcctcc ttaggacttt gtgggtccag   1560
ttttgccttc tgttctgatg gtgattagcg gctcacctcc agcgcttctt cctgtttccc   1620
aggaccaccc agaggctaag gaatcagtca ttccctgttg ccttctccag gaaggcaggc   1680
taagggttct gaggtgactg agaaaaatgt ttcctttgtg tggaaggctg gtgctccagc   1740
ctccacgtcc ctctgaatgg aagataaaaa cctgctggtg tcttgactgc tctgccaggc   1800
aatcctgaac atttgggcat gaagagctaa agtctttggg tcttgtttaa ctcctattac   1860
tgtccccaaa ttcccctagt cccttgggtc atgattaaac attttgactt aaaaaaaaaa   1920
aaaaaaaaaa aaaaa                                                    1935
```

<210> SEQ ID NO 5
<211> LENGTH: 397
<212> TYPE: PRT
<213> ORGANISM: Mus musculus

<400> SEQUENCE: 5

```
Met Gly Leu Ser Trp Ser Pro Arg Pro Pro Leu Leu Met Ile Leu Leu
 1               5                  10                  15

Leu Val Leu Ser Leu Trp Leu Pro Leu Gly Ala Gly Asn Ser Leu Ala
```

-continued

```
            20                  25                  30

Thr Glu Asn Arg Phe Val Asn Ser Cys Thr Gln Ala Arg Lys Lys Cys
        35                  40                  45

Glu Ala Asn Pro Ala Cys Lys Ala Ala Tyr Gln His Leu Gly Ser Cys
    50                  55                  60

Thr Ser Ser Leu Ser Arg Pro Leu Pro Leu Glu Glu Ser Ala Met Ser
65                  70                  75                  80

Ala Asp Cys Leu Glu Ala Ala Glu Gln Leu Arg Asn Ser Ser Leu Ile
                85                  90                  95

Asp Cys Arg Cys His Arg Arg Met Lys His Gln Ala Thr Cys Leu Asp
            100                 105                 110

Ile Tyr Trp Thr Val His Pro Ala Arg Ser Leu Gly Asp Tyr Glu Leu
        115                 120                 125

Asp Val Ser Pro Tyr Glu Asp Thr Val Thr Ser Lys Pro Trp Lys Met
    130                 135                 140

Asn Leu Ser Lys Leu Asn Met Leu Lys Pro Asp Ser Asp Leu Cys Leu
145                 150                 155                 160

Lys Phe Ala Met Leu Cys Thr Leu His Asp Lys Cys Asp Arg Leu Arg
                165                 170                 175

Lys Ala Tyr Gly Glu Ala Cys Ser Gly Ile Arg Cys Gln Arg His Leu
            180                 185                 190

Cys Leu Ala Gln Leu Arg Ser Phe Phe Glu Lys Ala Ala Glu Ser His
        195                 200                 205

Ala Gln Gly Leu Leu Leu Cys Pro Cys Ala Pro Glu Asp Ala Gly Cys
    210                 215                 220

Gly Glu Arg Arg Arg Asn Thr Ile Ala Pro Ser Cys Ala Leu Pro Ser
225                 230                 235                 240

Val Thr Pro Asn Cys Leu Asp Leu Arg Ser Phe Cys Arg Ala Asp Pro
                245                 250                 255

Leu Cys Arg Ser Arg Leu Met Asp Phe Gln Thr His Cys His Pro Met
            260                 265                 270

Asp Ile Leu Gly Thr Cys Ala Thr Glu Gln Ser Arg Cys Leu Arg Ala
        275                 280                 285

Tyr Leu Gly Leu Ile Gly Thr Ala Met Thr Pro Asn Phe Ile Ser Lys
    290                 295                 300

Val Asn Thr Thr Val Ala Leu Ser Cys Thr Cys Arg Gly Ser Gly Asn
305                 310                 315                 320

Leu Gln Asp Glu Cys Glu Gln Leu Glu Arg Ser Phe Ser Gln Asn Pro
                325                 330                 335

Cys Leu Val Glu Ala Ile Ala Ala Lys Met Arg Phe His Arg Gln Leu
            340                 345                 350

Phe Ser Gln Asp Trp Ala Asp Ser Thr Phe Ser Val Val Gln Gln Gln
        355                 360                 365

Asn Ser Asn Pro Ala Leu Arg Leu Gln Pro Arg Leu Pro Ile Leu Ser
    370                 375                 380

Phe Ser Ile Leu Pro Leu Ile Leu Leu Gln Thr Leu Trp
385                 390                 395
```

<210> SEQ ID NO 6
<211> LENGTH: 460
<212> TYPE: PRT
<213> ORGANISM: Homo sapiens

<400> SEQUENCE: 6

-continued

```
Met Phe Leu Ala Thr Leu Tyr Phe Ala Leu Pro Leu Leu Asp Leu Leu
 1               5                  10                  15

Leu Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Ala Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Val Val Pro Phe Ile Ser Val Glu His Ile Pro
    130                 135                 140

Lys Gly Asn Asn Cys Leu Asp Ala Ala Lys Ala Cys Asn Leu Asp Asp
145                 150                 155                 160

Ile Cys Lys Lys Tyr Arg Ser Ala Tyr Ile Thr Pro Cys Thr Thr Ser
                165                 170                 175

Val Ser Asn Asp Val Cys Asn Arg Arg Lys Cys His Lys Ala Leu Arg
            180                 185                 190

Gln Phe Phe Asp Lys Val Pro Ala Lys His Ser Tyr Gly Met Leu Phe
        195                 200                 205

Cys Ser Cys Arg Asp Ile Ala Cys Thr Glu Arg Arg Arg Gln Thr Ile
    210                 215                 220

Val Pro Val Cys Ser Tyr Glu Glu Arg Glu Lys Pro Asn Cys Leu Asn
225                 230                 235                 240

Leu Gln Asp Ser Cys Lys Thr Asn Tyr Ile Cys Arg Ser Arg Leu Ala
                245                 250                 255

Asp Phe Phe Thr Asn Cys Gln Pro Glu Ser Arg Ser Val Ser Ser Cys
            260                 265                 270

Leu Lys Glu Asn Tyr Ala Asp Cys Leu Leu Ala Tyr Ser Gly Leu Ile
        275                 280                 285

Gly Thr Val Met Thr Pro Asn Tyr Ile Asp Ser Ser Ser Leu Ser Val
    290                 295                 300

Ala Pro Trp Cys Asp Cys Ser Asn Ser Gly Asn Asp Leu Glu Glu Cys
305                 310                 315                 320

Leu Lys Phe Leu Asn Phe Phe Lys Asp Asn Thr Cys Leu Lys Asn Ala
                325                 330                 335

Ile Gln Ala Phe Gly Asn Gly Ser Asp Val Thr Val Trp Gln Pro Ala
            340                 345                 350

Phe Pro Val Gln Thr Thr Thr Ala Thr Thr Thr Thr Ala Leu Arg Val
        355                 360                 365

Lys Asn Lys Pro Leu Gly Pro Ala Gly Ser Glu Asn Glu Ile Pro Thr
    370                 375                 380

His Val Leu Pro Pro Cys Ala Asn Leu Gln Ala Gln Lys Leu Lys Ser
385                 390                 395                 400

Asn Val Ser Gly Asn Thr His Leu Cys Ile Ser Asn Gly Asn Tyr Glu
                405                 410                 415

Lys Glu Gly Leu Gly Ala Ser Ser His Ile Thr Thr Lys Ser Met Ala
```

-continued

```
            420                 425                 430

Ala Pro Pro Ser Cys Gly Leu Ser Pro Leu Leu Val Leu Val Val Thr
        435                 440                 445

Ala Leu Ser Thr Leu Leu Ser Leu Thr Glu Thr Ser
    450                 455                 460


<210> SEQ ID NO 7
<211> LENGTH: 464
<212> TYPE: PRT
<213> ORGANISM: Homo sapiens

<400> SEQUENCE: 7

Met Ile Leu Ala Asn Val Phe Phe Leu Phe Phe Phe Leu Asp Glu Thr
 1               5                  10                  15

Leu Arg Ser Leu Ala Ser Pro Ser Ser Leu Gln Asp Pro Glu Leu His
            20                  25                  30

Gly Trp Arg Pro Pro Val Asp Cys Val Arg Ala Asn Glu Leu Cys Ala
        35                  40                  45

Ala Glu Ser Asn Cys Ser Ser Arg Tyr Arg Thr Leu Arg Gln Cys Leu
    50                  55                  60

Ala Gly Arg Asp Arg Asn Thr Met Leu Ala Asn Lys Glu Cys Gln Ala
65                  70                  75                  80

Ala Leu Glu Val Leu Gln Glu Ser Pro Leu Tyr Asp Cys Arg Cys Lys
                85                  90                  95

Arg Gly Met Lys Lys Glu Leu Gln Cys Leu Gln Ile Tyr Trp Ser Ile
            100                 105                 110

His Leu Gly Leu Thr Glu Gly Glu Glu Phe Tyr Glu Ala Ser Pro Tyr
        115                 120                 125

Glu Pro Val Thr Ser Arg Leu Ser Asp Ile Phe Arg Leu Ala Ser Ile
    130                 135                 140

Phe Ser Gly Thr Gly Ala Asp Pro Val Val Ser Ala Lys Ser Asn His
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Arg Gln Thr Ile Leu Pro Ser
225                 230                 235                 240

Cys Ser Tyr Glu Asp Lys Glu Lys Pro Asn Cys Leu Asp Leu Arg Gly
                245                 250                 255

Val Cys Arg Thr Asp His Leu Cys Arg Ser Arg Leu Ala Asp Phe His
            260                 265                 270

Ala Asn Cys Arg Ala Ser Tyr Gln Thr Val Thr Ser Cys Pro Ala Asp
        275                 280                 285

Asn Tyr Gln Ala Cys Leu Gly Ser Tyr Ala Gly Met Ile Gly Phe Asp
    290                 295                 300

Met Thr Pro Asn Tyr Val Asp Ser Ser Pro Thr Gly Ile Val Val Ser
305                 310                 315                 320

Pro Trp Cys Ser Cys Arg Gly Ser Gly Asn Met Glu Glu Glu Cys Glu
                325                 330                 335
```

-continued

```
Lys Phe Leu Arg Asp Phe Thr Glu Asn Pro Cys Leu Arg Asn Ala Ile
            340                 345                 350

Gln Ala Phe Gly Asn Gly Thr Asp Val Asn Val Ser Pro Lys Gly Pro
        355                 360                 365

Ser Phe Gln Ala Thr Gln Ala Pro Arg Val Glu Lys Thr Pro Ser Leu
    370                 375                 380

Pro Asp Asp Leu Ser Asp Ser Thr Ser Leu Gly Thr Ser Val Ile Thr
385                 390                 395                 400

Thr Cys Thr Ser Val Gln Glu Gln Gly Leu Lys Ala Asn Asn Ser Lys
                405                 410                 415

Glu Leu Ser Met Cys Phe Thr Glu Leu Thr Thr Asn Ile Ile Pro Gly
            420                 425                 430

Ser Asn Lys Val Ile Lys Pro Asn Ser Gly Pro Ser Arg Ala Arg Pro
        435                 440                 445

Ser Ala Ala Leu Thr Val Leu Ser Val Leu Met Leu Lys Leu Ala Leu
    450                 455                 460


<210> SEQ ID NO 8
<211> LENGTH: 468
<212> TYPE: PRT
<213> ORGANISM: Rattus norvegicus

<400> SEQUENCE: 8

Met Phe Leu Ala Thr Leu Tyr Phe Ala Leu Pro Leu Leu Asp Leu Leu
 1               5                  10                  15

Met Ser Ala Glu Val Ser Gly Gly Asp Arg Leu Asp Cys Val Lys Ala
            20                  25                  30

Ser Asp Gln Cys Leu Lys Glu Gln Ser Cys Ser Thr Lys Tyr Arg Thr
        35                  40                  45

Leu Arg Gln Cys Val Ala Gly Lys Glu Thr Asn Phe Ser Leu Thr Ser
    50                  55                  60

Gly Leu Glu Ala Lys Asp Glu Cys Arg Ser Ala Met Glu Ala Leu Lys
65                  70                  75                  80

Gln Lys Ser Leu Tyr Asn Cys Arg Cys Lys Arg Gly Met Lys Lys Glu
                85                  90                  95

Lys Asn Cys Leu Arg Ile Tyr Trp Ser Met Tyr Gln Ser Leu Gln Gly
            100                 105                 110

Asn Asp Leu Leu Glu Asp Ser Pro Tyr Glu Pro Val Asn Ser Arg Leu
        115                 120                 125

Ser Asp Ile Phe Arg Ala Val Pro Phe Ile Ser Asp Val Phe Gln Gln
    130                 135                 140

Val Glu His Ile Ser Lys Gly Asn Asn Cys Leu Asp Ala Ala Lys Ala
145                 150                 155                 160

Cys Asn Leu Asp Asp Thr Cys Lys Lys Tyr Arg Ser Ala Tyr Ile Thr
                165                 170                 175

Pro Cys Thr Thr Ser Met Ser Asn Glu Val Cys Asn Arg Arg Lys Cys
            180                 185                 190

His Lys Ala Leu Arg Gln Phe Phe Asp Lys Val Pro Ala Lys His Ser
        195                 200                 205

Tyr Gly Met Leu Phe Cys Ser Cys Arg Asp Ile Ala Cys Thr Glu Arg
    210                 215                 220

Arg Arg Gln Thr Ile Val Pro Val Cys Ser Tyr Glu Glu Arg Glu Arg
225                 230                 235                 240

Pro Asn Cys Leu Ser Leu Gln Asp Ser Cys Lys Thr Asn Tyr Ile Cys
                245                 250                 255
```

-continued

Arg Ser Arg Leu Ala Asp Phe Phe Thr Asn Cys Gln Pro Glu Ser Arg
260 265 270

Ser Val Ser Asn Cys Leu Lys Glu Asn Tyr Ala Asp Cys Leu Leu Ala
275 280 285

Tyr Ser Gly Leu Ile Gly Thr Val Met Thr Pro Asn Tyr Val Asp Ser
290 295 300

Ser Ser Leu Ser Val Ala Pro Trp Cys Asp Cys Ser Asn Ser Gly Asn
305 310 315 320

Asp Leu Glu Asp Cys Leu Lys Phe Leu Asn Phe Phe Lys Asp Asn Thr
325 330 335

Cys Leu Lys Asn Ala Ile Gln Ala Phe Gly Asn Gly Ser Asp Val Thr
340 345 350

Met Trp Gln Pro Ala Pro Pro Val Gln Thr Thr Thr Ala Thr Thr Thr
355 360 365

Thr Ala Phe Arg Val Lys Asn Lys Pro Leu Gly Pro Ala Gly Ser Glu
370 375 380

Asn Glu Ile Pro Thr His Val Leu Pro Pro Cys Ala Asn Leu Gln Ala
385 390 395 400

Gln Lys Leu Lys Ser Asn Val Ser Gly Ser Thr His Leu Cys Leu Ser
405 410 415

Asp Ser Asp Phe Gly Lys Asp Gly Leu Ala Gly Ala Ser Ser His Ile
420 425 430

Thr Thr Lys Ser Met Ala Ala Pro Pro Ser Cys Ser Leu Ser Ser Leu
435 440 445

Pro Val Leu Met Leu Thr Ala Leu Ala Ala Leu Leu Ser Val Ser Leu
450 455 460

Ala Glu Thr Ser
465

<210> SEQ ID NO 9
<211> LENGTH: 464
<212> TYPE: PRT
<213> ORGANISM: Rattus Norvegicus

<400> SEQUENCE: 9

Met Ile Leu Ala Asn Ala Phe Cys Leu Phe Phe Phe Leu Asp Glu Thr
1 5 10 15

Leu Arg Ser Leu Ala Ser Pro Ser Ser Leu Gln Gly Ser Glu Leu His
20 25 30

Gly Trp Arg Pro Gln Val Asp Cys Val Arg Ala Asn Glu Leu Cys Ala
35 40 45

Ala Glu Ser Asn Cys Ser Ser Arg Tyr Arg Thr Leu Arg Gln Cys Leu
50 55 60

Ala Gly Arg Asp Arg Asn Thr Met Leu Ala Asn Lys Glu Cys Gln Ala
65 70 75 80

Ala Leu Glu Val Leu Gln Glu Ser Pro Leu Tyr Asp Cys Arg Cys Lys
85 90 95

Arg Gly Met Lys Lys Glu Leu Gln Cys Leu Gln Ile Tyr Trp Ser Ile
100 105 110

His Leu Gly Leu Thr Glu Gly Glu Glu Phe Tyr Glu Ala Ser Pro Tyr
115 120 125

Glu Pro Val Thr Ser Arg Leu Ser Asp Ile Phe Arg Leu Ala Ser Ile
130 135 140

Phe Ser Gly Thr Gly Thr Asp Pro Ala Val Ser Thr Lys Ser Asn His

-continued

```
145                 150                 155                 160

Cys Leu Asp Ala Ala Lys Ala Cys Asn Leu Asn Asp Asn Cys Lys Lys
                165                 170                 175

Leu Arg Ser Ser Tyr Ile Ser Ile Cys Asn Arg Glu Ile Ser Pro Thr
            180                 185                 190

Glu Arg Cys Asn Arg Arg Lys Cys His Lys Ala Leu Arg Gln Phe Phe
        195                 200                 205

Asp Arg Val Pro Ser Glu Tyr Thr Tyr Arg Met Leu Phe Cys Ser Cys
    210                 215                 220

Gln Asp Gln Ala Cys Ala Glu Arg Arg Arg Gln Thr Ile Leu Pro Ser
225                 230                 235                 240

Cys Ser Tyr Glu Asp Lys Glu Lys Pro Asn Cys Leu Asp Leu Arg Ser
                245                 250                 255

Leu Cys Arg Thr Asp His Leu Cys Arg Ser Arg Leu Ala Asp Phe His
            260                 265                 270

Ala Asn Cys Arg Ala Ser Tyr Arg Thr Ile Thr Ser Cys Pro Ala Asp
        275                 280                 285

Asn Tyr Gln Ala Cys Leu Gly Ser Tyr Ala Gly Met Ile Gly Phe Asp
    290                 295                 300

Met Thr Pro Asn Tyr Val Asp Ser Asn Pro Thr Gly Ile Val Val Ser
305                 310                 315                 320

Pro Trp Cys Asn Cys Arg Gly Ser Gly Asn Met Glu Glu Glu Cys Glu
                325                 330                 335

Lys Phe Leu Arg Asp Phe Thr Glu Asn Pro Cys Leu Arg Asn Ala Ile
            340                 345                 350

Gln Ala Phe Gly Asn Gly Thr Asp Val Asn Met Ser Pro Lys Gly Pro
        355                 360                 365

Ser Leu Pro Ala Thr Gln Ala Pro Arg Val Glu Lys Thr Pro Ser Leu
    370                 375                 380

Pro Asp Asp Leu Ser Asp Ser Thr Ser Leu Gly Thr Ser Val Ile Thr
385                 390                 395                 400

Thr Cys Thr Ser Ile Gln Glu Gln Gly Leu Lys Ala Asn Asn Ser Lys
                405                 410                 415

Glu Leu Ser Met Cys Phe Thr Glu Leu Thr Thr Asn Ile Ser Pro Gly
            420                 425                 430

Ser Lys Lys Val Ile Lys Leu Asn Ser Gly Ser Ser Arg Ala Arg Leu
        435                 440                 445

Ser Ala Ala Leu Thr Ala Leu Pro Leu Leu Met Leu Thr Leu Ala Leu
    450                 455                 460
```

<210> SEQ ID NO 10
<211> LENGTH: 282
<212> TYPE: DNA
<213> ORGANISM: Homo sapiens
<220> FEATURE:
<221> NAME/KEY: unsure
<222> LOCATION: (0)...(0)
<223> OTHER INFORMATION: n = A, T, C or G

<400> SEQUENCE: 10

```
gcgctgnntg ncngnangng ggggcgggag gtgccggtcg agggagcccc gctctcagag      60

ctccagggga ggagcgangg gagcgcggag cccggccgcc tacagctcgc catggtgcgc     120

cccctgaacc cgcgaccgct gccgcccgta gnnnnnnnnn nnnnnnnnnn nnnnnnnnnn     180

nnnnnnnngc ctctcgcagc cggagacccc cttcccacag aaagccgact catgaacagc     240
```

-continued tgtctccagg ccaggaggaa gtgccaggct gatcccacct gc 282

<210> SEQ ID NO 11
<211> LENGTH: 20
<212> TYPE: DNA
<213> ORGANISM: Homo sapiens

<400> SEQUENCE: 11
gcctctcgca gccggagacc 20

<210> SEQ ID NO 12
<211> LENGTH: 21
<212> TYPE: DNA
<213> ORGANISM: Homo sapiens

<400> SEQUENCE: 12
caggtgggat cagcctggca c 21

<210> SEQ ID NO 13
<211> LENGTH: 41
<212> TYPE: DNA
<213> ORGANISM: Homo sapiens

<400> SEQUENCE: 13
tctcgcagcc ggagaccccc ttcccacaga aagccgactc a 41

<210> SEQ ID NO 14
<211> LENGTH: 1792
<212> TYPE: DNA
<213> ORGANISM: Homo sapiens

<400> SEQUENCE: 14
atggtgcgcc ccctgaaccc gcgaccgctg ccgcccgtag tcctgatgtt gctgctgctg 60
ctgccgccgt cgccgctgcc tctcgcagcc ggagaccccc ttcccacaga aagccgactc 120
atgaacagct gtctccaggc caggaggaag tgccaggctg atcccacctg cagtgctgcc 180
taccaccacc tggattcctg cacctctagc ataagcaccc cactgccctc agaggagcct 240
tcggtccctg ctgactgcct ggaggcagca cagcaactca ggaacagctc tctgataggc 300
tgcatgtgcc accggcgcat gaagaaccag gttgcctgct tggacatcta ttggaccgtt 360
caccgtgccc gcagccttgg taactatgag ctggatgtct ccccctatga agacacagtg 420
accagcaaac cctggaaaat gaatctcagc aaactgaaca tgctcaaacc agactcagac 480
ctctgcctca agtttgccat gctgtgtact ctcaatgaca agtgtgaccg gctgcgcaag 540
gcctacgggg aggcgtgctc cgggccccac tgccagcgcc acgtctgcct caggcagctg 600
ctcactttct tcgagaaggc cgccgagccc cacgcgcagg gcctgctact gtgcccatgt 660
gcccccaacg accggggctg cggggagcgc cggcgcaaca ccatcgcccc caactgcgcg 720
ctgccgcctg tggcccccaa ctgcctggag ctgcggcgcc tctgcttctc cgacccgctt 780
tgcagatcac gcctggtgga tttccagacc cactgccatc ccatggacat cctaggaact 840
tgtgcaacag agcagtccag atgtctacga gcatacctgg ggctgattgg gactgccatg 900
acccccaact ttgtcagcaa tgtcaacacc agtgttgcct taagctgcac ctgccgaggc 960
agtggcaacc tgcaggagga gtgtgaaatg ctggaagggt tcttctccca caacccctgc 1020
ctcacggagg ccattgcagc taagatgcgt tttcacagcc aactcttctc ccaggactgg 1080
ccacacccta cctttgctgt gatggcacac cagaatgaaa accctgctgt gaggccacag 1140
ccctgggtgc cctctctttt ctcctgcacg cttcccttga ttctgctcct gagcctatgg 1200

-continued

```
tagctggact tccccagggc cctcttcccc tccaccacac ccaggtggac ttgcagccca   1260

caaggggtga ggaaaggaca gcagcaggaa ggaggtgcag tgcgcagatg agggcacagg   1320

agaagctaag ggttatgacc tccagatcct tactggtcca gtcctcattc cctccacccc   1380

atctccactt ctgattcatg ctgcccctcc ttggtggcca caatttagcc atgtcatctg   1440

gtggtgacca gctccaccaa gcccctttct gagcccttcc tcttgactac caggatcacc   1500

agaatctaat aagttagcct ttctctattg cattccagat tagggttagg gtagggagga   1560

ctgggtgttc tgaggcagcc tagaaagtca ttctcctttg tgaagaaggc tcctgccccc   1620

tcgtctcctc ctctgagtgg aggatggaaa actactgcct gcactgccct gtccccggat   1680

cctgccgaac atctgggcat caggagctgg agcctgtggg ccttgcttta ttcctattat   1740

tgtcctaaag tctctctggg ctcttggatc atgattaaac ctttgactta ag            1792


<210> SEQ ID NO 15
<211> LENGTH: 400
<212> TYPE: PRT
<213> ORGANISM: Homo Sapiens

<400> SEQUENCE: 15

Met Val Arg Pro Leu Asn Pro Arg Pro Leu Pro Pro Val Val Leu Met
 1               5                  10                  15

Leu Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190

Arg His Val Cys Leu Arg Gln Leu Leu Thr Phe Phe Glu Lys Ala Ala
        195                 200                 205

Glu Pro His Ala Gln Gly Leu Leu Leu Cys Pro Cys Ala Pro Asn Asp
    210                 215                 220

Arg Gly Cys Gly Glu Arg Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270
```

-continued

His Pro Met Asp Ile Leu Gly Thr Cys Ala Thr Glu Gln Ser Arg Cys
275 280 285

Leu Arg Ala Tyr Leu Gly Leu Ile Gly Thr Ala Met Thr Pro Asn Phe
290 295 300

Val Ser Asn Val Asn Thr Ser Val Ala Leu Ser Cys Thr Cys Arg Gly
305 310 315 320

Ser Gly Asn Leu Gln Glu Glu Cys Glu Met Leu Glu Gly Phe Phe Ser
325 330 335

His Asn Pro Cys Leu Thr Glu Ala Ile Ala Ala Lys Met Arg Phe His
340 345 350

Ser Gln Leu Phe Ser Gln Asp Trp Pro His Pro Thr Phe Ala Val Met
355 360 365

Ala His Gln Asn Glu Asn Pro Ala Val Arg Pro Gln Pro Trp Val Pro
370 375 380

Ser Leu Phe Ser Cys Thr Leu Pro Leu Ile Leu Leu Leu Ser Leu Trp
385 390 395 400

<210> SEQ ID NO 16
<211> LENGTH: 1837
<212> TYPE: DNA
<213> ORGANISM: Homo sapeins

<400> SEQUENCE: 16
cccaggaccc tggtgggaga gtgtgtgcgt cgcgctggag ggcgggaggc gggggcggga 60
ggtgccggtc gagggagccc cgctctcaga gctccagggg aggagcgagg ggagcgcgga 120
gcccggcgcc tacagctcgc catggtgcgc cccctgaacc cgcgaccgct gccgcccgta 180
gtcctgatgt tgctgctgct gctgccgccg tcgccgctgc ctctcgcagc cggagacccc 240
cttcccacag aaagccgact catgaacagc tgtctccagg ccaggaggaa gtgccaggct 300
gatcccacct gcagtgctgc ctaccaccac ctggattcct gcacctctag cataagcacc 360
ccactgccct cagaggagcc ttcggtccct gctgactgcc tggaggcagc acagcaactc 420
aggaacagct ctctgatagg ctgcatgtgc caccggcgca tgaagaacca ggttgcctgc 480
ttggacatct attggaccgt tcaccgtgcc cgcagccttg actcagacct ctgcctcaag 540
tttgccatgc tgtgtactct caatgacaag tgtgaccggc tgcgcaaggc ctacggggag 600
gcgtgctccg ggccccactg ccagcgccac gtctgcctca ggcagctgct cactttcttc 660
gagaaggccg ccgagcccca cgcgcagggc ctgctactgt gcccatgtgc ccccaacgac 720
cggggctgcg gggagcgccg gcgcaacacc atcgccccca actgcgcgct gccgcctgtg 780
gcccccaact gcctggagct gcggcgcctc tgcttctccg acccgctttg cagatcacgc 840
ctggtggatt tccagaccca ctgccatccc atggacatcc taggaacttg tgcaacagag 900
cagtccagat gtctacgagc atacctgggg ctgattggga ctgccatgac cccaacttt 960 gtcagcaatg tcaacaccag tgttgcctta agctgcacct gccgaggcag tggcaacctg 1020
caggaggagt gtgaaatgct ggaagggttc ttctcccaca accccctgcct cacggaggcc 1080 attgcagcta agatgcgttt tcacagccaa ctcttctccc aggactggcc acaccctacc 1140
tttgctgtga tggcacacca gaatgaaaac cctgctgtga ggccacagcc ctgggtgccc 1200
tctcttttct cctgcacgct tcccttgatt ctgctcctga gcctatggta gctggacttc 1260
cccagggccc tcttcccctc caccacaccc aggtggactt gcagcccaca aggggtgagg 1320
aaaggacagc agcaggaagg aggtgcagtg cgcagatgag ggcacaggag aagctaaggg 1380

-continued

```
ttatgacctc cagatcctta ctggtccagt cctcattccc tccaccccat ctccacttct   1440

gattcatgct gcccctcctt ggtggccaca atttagccat gtcatctggt ggtgaccagc   1500

tccaccaagc ccctttctga gcccttcctc ttgactacca ggatcaccag aatctaataa   1560

gttagccttt ctctattgca ttccagatta gggttagggt agggaggact gggtgttctg   1620

aggcagccta gaaagtcatt ctcctttgtg aagaaggctc ctgccccctc gtctcctcct   1680

ctgagtggag gatggaaaac tactgcctgc actgccctgt ccccggatcc tgccgaacat   1740

ctgggcatca ggagctggag cctgtgggcc ttgctttatt cctattattg tcctaaagtc   1800

tctctgggct cttggatcat gattaaacct ttgactt                            1837


<210> SEQ ID NO 17
<211> LENGTH: 369
<212> TYPE: PRT
<213> ORGANISM: Homo sapiens

<400> SEQUENCE: 17

Met Val Arg Pro Leu Asn Pro Arg Pro Leu Pro Pro Val Val Leu Met
 1               5                  10                  15

Leu Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Asp Ser
        115                 120                 125

Asp Leu Cys Leu Lys Phe Ala Met Leu Cys Thr Leu Asn Asp Lys Cys
    130                 135                 140

Asp Arg Leu Arg Lys Ala Tyr Gly Glu Ala Cys Ser Gly Pro His Cys
145                 150                 155                 160

Gln Arg His Val Cys Leu Arg Gln Leu Leu Thr Phe Phe Glu Lys Ala
                165                 170                 175

Ala Glu Pro His Ala Gln Gly Leu Leu Leu Cys Pro Cys Ala Pro Asn
            180                 185                 190

Asp Arg Gly Cys Gly Glu Arg Arg Arg Asn Thr Ile Ala Pro Asn Cys
        195                 200                 205

Ala Leu Pro Pro Val Ala Pro Asn Cys Leu Glu Leu Arg Arg Leu Cys
    210                 215                 220

Phe Ser Asp Pro Leu Cys Arg Ser Arg Leu Val Asp Phe Gln Thr His
225                 230                 235                 240

Cys His Pro Met Asp Ile Leu Gly Thr Cys Ala Thr Glu Gln Ser Arg
                245                 250                 255

Cys Leu Arg Ala Tyr Leu Gly Leu Ile Gly Thr Ala Met Thr Pro Asn
            260                 265                 270

Phe Val Ser Asn Val Asn Thr Ser Val Ala Leu Ser Cys Thr Cys Arg
        275                 280                 285

Gly Ser Gly Asn Leu Gln Glu Glu Cys Glu Met Leu Glu Gly Phe Phe
```

-continued

```
    290                 295                 300

Ser His Asn Pro Cys Leu Thr Glu Ala Ile Ala Ala Lys Met Arg Phe
305                 310                 315                 320

His Ser Gln Leu Phe Ser Gln Asp Trp Pro His Pro Thr Phe Ala Val
                325                 330                 335

Met Ala His Gln Asn Glu Asn Pro Ala Val Arg Pro Gln Pro Trp Val
            340                 345                 350

Pro Ser Leu Phe Ser Cys Thr Leu Pro Leu Ile Leu Leu Leu Ser Leu
        355                 360                 365

Trp


<210> SEQ ID NO 18
<211> LENGTH: 628
<212> TYPE: PRT
<213> ORGANISM: Artificial Sequence
<220> FEATURE:
<223> OTHER INFORMATION: Chimeric receptor comprising human sequence.

<400> SEQUENCE: 18

Met Val Arg Pro Leu Asn Pro Arg Pro Leu Pro Pro Val Val Leu Met
 1               5                  10                  15

Leu Leu Leu Leu Leu Pro Pro Ser Pro Leu Pro Leu Ala Ala Gly Asp
            20                  25                  30

Pro Leu Pro Thr Glu Ser Arg Leu Met Asn Ser Cys Leu Gln Ala Arg
        35                  40                  45

Arg Lys Cys Gln Ala Asp Pro Thr Cys Ser Ala Ala Tyr His His Leu
    50                  55                  60

Asp Ser Cys Thr Ser Ser Ile Ser Thr Pro Leu Pro Ser Glu Glu Pro
65                  70                  75                  80

Ser Val Pro Ala Asp Cys Leu Glu Ala Ala Gln Gln Leu Arg Asn Ser
                85                  90                  95

Ser Leu Ile Gly Cys Met Cys His Arg Arg Met Lys Asn Gln Val Ala
            100                 105                 110

Cys Leu Asp Ile Tyr Trp Thr Val His Arg Ala Arg Ser Leu Gly Asn
        115                 120                 125

Tyr Glu Leu Asp Val Ser Pro Tyr Glu Asp Thr Val Thr Ser Lys Pro
    130                 135                 140

Trp Lys Met Asn Leu Ser Lys Leu Asn Met Leu Lys Pro Asp Ser Asp
145                 150                 155                 160

Leu Cys Leu Lys Phe Ala Met Leu Cys Thr Leu Asn Asp Lys Cys Asp
                165                 170                 175

Arg Leu Arg Lys Ala Tyr Gly Glu Ala Cys Ser Gly Pro His Cys Gln
            180                 185                 190

Arg His Val Cys Leu Arg Gln Leu Leu Thr Phe Phe Glu Lys Ala Ala
        195                 200                 205

Glu Pro His Ala Gln Gly Leu Leu Leu Cys Pro Cys Ala Pro Asn Asp
    210                 215                 220

Arg Gly Cys Gly Glu Arg Arg Arg Asn Thr Ile Ala Pro Asn Cys Ala
225                 230                 235                 240

Leu Pro Pro Val Ala Pro Asn Cys Leu Glu Leu Arg Arg Leu Cys Phe
                245                 250                 255

Ser Asp Pro Leu Cys Arg Ser Arg Leu Val Asp Phe Gln Thr His Cys
            260                 265                 270

His Pro Met Asp Ile Leu Gly Thr Cys Ala Thr Glu Gln Ser Arg Cys
        275                 280                 285
```

-continued

```
Leu Arg Ala Tyr Leu Gly Leu Ile Gly Thr Ala Met Thr Pro Asn Phe
    290                 295                 300

Val Ser Asn Val Asn Thr Ser Val Ala Leu Ser Cys Thr Cys Arg Gly
305                 310                 315                 320

Ser Gly Asn Leu Gln Glu Glu Cys Glu Met Leu Glu Gly Phe Phe Ser
                325                 330                 335

His Asn Pro Cys Leu Thr Glu Ala Ile Ala Ala Lys Met Arg Phe His
            340                 345                 350

Ser Gln Leu Phe Ser Gln Asp Trp Pro His Pro Thr Phe Ala Val Met
        355                 360                 365

Ala His Gln Asn Glu Asn Pro Ala Val Arg Pro Gln Pro Trp Val Pro
    370                 375                 380

Ser Leu Phe Ser Cys Thr Leu Pro Leu Ile Leu Leu Leu Ser Leu Trp
385                 390                 395                 400

Pro Asp Lys Thr His Thr Cys Pro Pro Cys Pro Ala Pro Glu Leu Leu
                405                 410                 415

Gly Gly Pro Ser Val Phe Leu Phe Pro Pro Lys Pro Lys Asp Thr Leu
            420                 425                 430

Met Ile Ser Arg Thr Pro Glu Val Thr Cys Val Val Val Asp Val Ser
        435                 440                 445

His Glu Asp Pro Glu Val Lys Phe Asn Trp Tyr Val Asp Gly Val Glu
    450                 455                 460

Val His Asn Ala Lys Thr Lys Pro Arg Glu Glu Gln Tyr Asn Ser Thr
465                 470                 475                 480

Tyr Arg Val Val Ser Val Leu Thr Val Leu His Gln Asp Trp Leu Asn
                485                 490                 495

Gly Lys Glu Tyr Lys Cys Lys Val Ser Asn Lys Ala Leu Pro Ala Pro
            500                 505                 510

Ile Glu Lys Thr Ile Ser Lys Ala Lys Gly Gln Pro Arg Glu Pro Gln
        515                 520                 525

Val Tyr Thr Leu Pro Pro Ser Arg Glu Glu Met Thr Lys Asn Gln Val
    530                 535                 540

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
                565                 570                 575

Pro Val Leu Asp Ser Asp Gly Ser Phe Phe Leu Tyr Ser Lys Leu Thr
            580                 585                 590

Val Asp Lys Ser Arg Trp Gln Gln Gly Asn Val Phe Ser Cys Ser Val
        595                 600                 605

Met His Glu Ala Leu His Asn His Tyr Thr Gln Lys Ser Leu Ser Leu
    610                 615                 620

Ser Pro Gly Lys
625
```

<210> SEQ ID NO 19
<211> LENGTH: 951
<212> TYPE: PRT
<213> ORGANISM: Artificial Sequence
<220> FEATURE:
<223> OTHER INFORMATION: Chimeric receptor comprising rat sequence.

<400> SEQUENCE: 19

```
Met Gly Gly Thr Ala Ala Arg Leu Gly Ala Val Ile Leu Phe Val Val
 1               5                  10                  15
```

-continued

```
Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Pro Ser Ser Leu Gln Gly Ser Glu Leu
    50                  55                  60

His Gly Trp Arg Pro Gln Val Asp Cys Val Arg Ala Asn Glu Leu Cys
65                  70                  75                  80

Ala Ala Glu Ser Asn Cys Ser Ser Arg Tyr Arg Thr Leu Arg Gln Cys
                85                  90                  95

Leu Ala Gly Arg Asp Arg Asn Thr Met Leu Ala Asn Lys Glu Cys Gln
            100                 105                 110

Ala Ala Leu Glu Val Leu Gln Glu Ser Pro Leu Tyr Asp Cys Arg Cys
        115                 120                 125

Lys Arg Gly Met Lys Lys Glu Leu Gln Cys Leu Gln Ile Tyr Trp Ser
    130                 135                 140

Ile His Leu Gly Leu Thr Glu Gly Glu Glu Phe Tyr Glu Ala Ser Pro
145                 150                 155                 160

Tyr Glu Pro Val Thr Ser Arg Leu Ser Asp Ile Phe Arg Leu Ala Ser
                165                 170                 175

Ile Phe Ser Gly Thr Gly Thr Asp Pro Ala Val Ser Thr Lys Ser Asn
            180                 185                 190

His Cys Leu Asp Ala Ala Lys Ala Cys Asn Leu Asn Asp Asn Cys Lys
        195                 200                 205

Lys Leu Arg Ser Ser Tyr Ile Ser Ile Cys Asn Arg Glu Ile Ser Pro
    210                 215                 220

Thr Glu Arg Cys Asn Arg Arg Lys Cys His Lys Ala Leu Arg Gln Phe
225                 230                 235                 240

Phe Asp Arg Val Pro Ser Glu Tyr Thr Tyr Arg Met Leu Phe Cys Ser
                245                 250                 255

Cys Gln Asp Gln Ala Cys Ala Glu Arg Arg Arg Gln Thr Ile Leu Pro
            260                 265                 270

Ser Cys Ser Tyr Glu Asp Lys Glu Lys Pro Asn Cys Leu Asp Leu Arg
        275                 280                 285

Ser Leu Cys Arg Thr Asp His Leu Cys Arg Ser Arg Leu Ala Asp Phe
    290                 295                 300

His Ala Asn Cys Arg Ala Ser Tyr Arg Thr Ile Thr Ser Cys Pro Ala
305                 310                 315                 320

Asp Asn Tyr Gln Ala Cys Leu Gly Ser Tyr Ala Gly Met Ile Gly Phe
                325                 330                 335

Asp Met Thr Pro Asn Tyr Val Asp Ser Asn Pro Thr Gly Ile Val Val
            340                 345                 350

Ser Pro Trp Cys Asn Cys Arg Gly Ser Gly Asn Met Glu Glu Glu Cys
        355                 360                 365

Glu Lys Phe Leu Arg Asp Phe Thr Glu Asn Pro Cys Leu Arg Asn Ala
    370                 375                 380

Ile Gln Ala Phe Gly Asn Gly Thr Asp Val Asn Met Ser Pro Lys Gly
385                 390                 395                 400

Pro Ser Leu Pro Ala Thr Gln Ala Pro Arg Val Glu Lys Thr Pro Ser
                405                 410                 415

Leu Pro Asp Asp Leu Ser Asp Ser Thr Ser Leu Gly Thr Ser Val Ile
            420                 425                 430
```

-continued

```
Thr Thr Cys Thr Ser Ile Gln Glu Gln Gly Leu Lys Ala Asn Asn Ser
        435                 440                 445

Lys Glu Leu Ser Met Cys Phe Thr Glu Leu Thr Thr Asn Ile Ile Pro
    450                 455                 460

Gly Trp Arg Ala Trp Val Pro Val Val Leu Gly Val Leu Thr Ala Leu
465                 470                 475                 480

Val Thr Ala Ala Ala Leu Ala Leu Ile Leu Leu Arg Lys Arg Arg Lys
                485                 490                 495

Glu Thr Arg Phe Gly Gln Ala Phe Asp Ser Val Met Ala Arg Gly Glu
            500                 505                 510

Pro Ala Val His Phe Arg Ala Ala Arg Ser Phe Asn Arg Glu Arg Pro
        515                 520                 525

Glu Arg Ile Glu Ala Thr Leu Asp Ser Leu Gly Ile Ser Asp Glu Leu
    530                 535                 540

Lys Glu Lys Leu Glu Asp Val Leu Ile Pro Glu Gln Gln Phe Thr Leu
545                 550                 555                 560

Gly Arg Met Leu Gly Lys Gly Glu Phe Gly Ser Val Arg Glu Ala Gln
                565                 570                 575

Leu Lys Gln Glu Asp Gly Ser Phe Val Lys Val Ala Val Lys Met Leu
            580                 585                 590

Lys Ala Asp Ile Ile Ala Ser Ser Asp Ile Glu Glu Phe Leu Arg Glu
        595                 600                 605

Ala Ala Cys Met Lys Glu Phe Asp His Pro His Val Ala Lys Leu Val
    610                 615                 620

Gly Val Ser Leu Arg Ser Arg Ala Lys Gly Arg Leu Pro Ile Pro Met
625                 630                 635                 640

Val Ile Leu Pro Phe Met Lys His Gly Asp Leu His Ala Phe Leu Leu
                645                 650                 655

Ala Ser Arg Ile Gly Glu Asn Pro Phe Asn Leu Pro Leu Gln Thr Leu
            660                 665                 670

Ile Arg Phe Met Val Asp Ile Ala Cys Gly Met Glu Tyr Leu Ser Ser
        675                 680                 685

Arg Asn Phe Ile His Arg Asp Leu Ala Ala Arg Asn Cys Met Leu Ala
    690                 695                 700

Glu Asp Met Thr Val Cys Val Ala Asp Phe Gly Leu Ser Arg Lys Ile
705                 710                 715                 720

Tyr Ser Gly Asp Tyr Tyr Arg Gln Gly Cys Ala Ser Lys Leu Pro Val
                725                 730                 735

Lys Trp Leu Ala Leu Glu Ser Leu Ala Asp Asn Leu Tyr Thr Val Gln
            740                 745                 750

Ser Asp Val Trp Ala Phe Gly Val Thr Met Trp Glu Ile Met Thr Arg
        755                 760                 765

Gly Gln Thr Pro Tyr Ala Gly Ile Glu Asn Ala Glu Ile Tyr Asn Tyr
    770                 775                 780

Leu Ile Gly Gly Asn Arg Leu Lys Gln Pro Pro Glu Cys Met Glu Asp
785                 790                 795                 800

Val Tyr Asp Leu Met Tyr Gln Cys Trp Ser Ala Asp Pro Lys Gln Arg
                805                 810                 815

Pro Ser Phe Thr Cys Leu Arg Met Glu Leu Glu Asn Ile Leu Gly Gln
            820                 825                 830

Leu Ser Val Leu Ser Ala Ser Gln Asp Pro Leu Tyr Ile Asn Ile Glu
        835                 840                 845

Arg Ala Glu Glu Pro Thr Ala Gly Gly Ser Leu Glu Leu Pro Gly Arg
```

-continued

```
    850                 855                 860

Asp Gln Pro Tyr Ser Gly Ala Gly Asp Gly Ser Gly Met Gly Ala Val
865                 870                 875                 880

Gly Gly Thr Pro Ser Asp Cys Arg Tyr Ile Leu Thr Pro Gly Gly Leu
                885                 890                 895

Ala Glu Gln Pro Gly Gln Ala Glu His Gln Pro Glu Ser Pro Leu Asn
            900                 905                 910

Glu Thr Gln Arg Leu Leu Leu Leu Gln Gln Gly Leu Leu Pro His Ser
        915                 920                 925

Ser Cys Ala Asp Ala Ser Leu Lys Met Ala Asp Pro Asn Arg Phe Arg
    930                 935                 940

Gly Lys Asp Leu Pro Val Leu
945                 950


<210> SEQ ID NO 20
<211> LENGTH: 888
<212> TYPE: PRT
<213> ORGANISM: Artificial Sequence
<220> FEATURE:
<223> OTHER INFORMATION: Chimeric receptor comprising murine sequence.

<400> SEQUENCE: 20

Met Gly Gly Thr Ala Ala Arg Leu Gly Ala Val Ile Leu Phe Val Val
 1               5                  10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Leu Glu Ala Gly Asn Ser Leu Ala Thr Glu Asn
    50                  55                  60

Arg Phe Val Asn Ser Cys Thr Gln Ala Arg Lys Lys Cys Glu Ala Asn
65                  70                  75                  80

Pro Ala Cys Lys Ala Ala Tyr Gln His Leu Gly Ser Cys Thr Ser Ser
                85                  90                  95

Leu Ser Arg Pro Leu Pro Leu Glu Glu Ser Ala Met Ser Ala Asp Cys
            100                 105                 110

Leu Glu Ala Ala Glu Gln Leu Arg Asn Ser Ser Leu Ile Asp Cys Arg
        115                 120                 125

Cys His Arg Arg Met Lys His Gln Ala Thr Cys Leu Asp Ile Tyr Trp
    130                 135                 140

Thr Val His Pro Ala Arg Ser Leu Gly Asp Tyr Glu Leu Asp Val Ser
145                 150                 155                 160

Pro Tyr Glu Asp Thr Val Thr Ser Lys Pro Trp Lys Met Asn Leu Ser
                165                 170                 175

Lys Leu Asn Met Leu Lys Pro Asp Ser Asp Leu Cys Leu Lys Phe Ala
            180                 185                 190

Met Leu Cys Thr Leu His Asp Lys Cys Asp Arg Leu Arg Lys Ala Tyr
        195                 200                 205

Gly Glu Ala Cys Ser Gly Ile Arg Cys Gln Arg His Leu Cys Leu Ala
    210                 215                 220

Gln Leu Arg Ser Phe Phe Glu Lys Ala Ala Glu Ser His Ala Gln Gly
225                 230                 235                 240

Leu Leu Leu Cys Pro Cys Pro Pro Glu Asp Ala Gly Cys Gly Glu Arg
                245                 250                 255

Arg Arg Asn Thr Ile Ala Pro Ser Cys Ala Leu Pro Ser Val Thr Pro
```

-continued

```
            260                 265                 270

Asn Cys Leu Asp Leu Arg Ser Phe Cys Arg Ala Asp Pro Leu Cys Arg
        275                 280                 285

Ser Arg Leu Met Asp Phe Gln Thr His Cys His Pro Met Asp Ile Leu
    290                 295                 300

Gly Thr Cys Ala Thr Glu Gln Ser Arg Cys Leu Arg Ala Tyr Leu Gly
305                 310                 315                 320

Leu Ile Gly Thr Ala Met Thr Pro Asn Phe Ile Ser Lys Val Asn Thr
                325                 330                 335

Thr Val Ala Leu Ser Cys Thr Cys Arg Gly Ser Gly Asn Leu Gln Asp
            340                 345                 350

Glu Cys Glu Gln Leu Glu Arg Ser Phe Ser Gln Asn Pro Cys Leu Val
        355                 360                 365

Glu Ala Ile Ala Ala Lys Met Arg Phe His Arg Gln Leu Phe Ser Gln
    370                 375                 380

Asp Trp Ala Asp Ser Thr Phe Ser Val Val Gln Gln Gln Asn Ser Asn
385                 390                 395                 400

Pro Ala Trp Arg Ala Trp Val Pro Val Val Leu Gly Val Leu Thr Ala
                405                 410                 415

Leu Val Thr Ala Ala Ala Leu Ala Leu Ile Leu Leu Arg Lys Arg Arg
            420                 425                 430

Lys Glu Thr Arg Phe Gly Gln Ala Phe Asp Ser Val Met Ala Arg Gly
        435                 440                 445

Glu Pro Ala Val His Phe Arg Ala Ala Arg Ser Phe Asn Arg Glu Arg
    450                 455                 460

Pro Glu Arg Ile Glu Ala Thr Leu Asp Ser Leu Gly Ile Ser Asp Glu
465                 470                 475                 480

Leu Lys Glu Lys Leu Glu Asp Val Leu Ile Pro Glu Gln Gln Phe Thr
                485                 490                 495

Leu Gly Arg Met Leu Gly Lys Gly Glu Phe Gly Ser Val Arg Glu Ala
            500                 505                 510

Gln Leu Lys Gln Glu Asp Gly Ser Phe Val Lys Val Ala Val Lys Met
        515                 520                 525

Leu Lys Ala Asp Ile Ile Ala Ser Ser Asp Ile Glu Glu Phe Leu Arg
    530                 535                 540

Glu Ala Ala Cys Met Lys Glu Phe Asp His Pro His Val Ala Lys Leu
545                 550                 555                 560

Val Gly Val Ser Leu Arg Ser Arg Ala Lys Gly Arg Leu Pro Ile Pro
                565                 570                 575

Met Val Ile Leu Pro Phe Met Lys His Gly Asp Leu His Ala Phe Leu
            580                 585                 590

Leu Ala Ser Arg Ile Gly Glu Asn Pro Phe Asn Leu Pro Leu Gln Thr
        595                 600                 605

Leu Ile Arg Phe Met Val Asp Ile Ala Cys Gly Met Glu Tyr Leu Ser
    610                 615                 620

Ser Arg Asn Phe Ile His Arg Asp Leu Ala Ala Arg Asn Cys Met Leu
625                 630                 635                 640

Ala Glu Asp Met Thr Val Cys Val Ala Asp Phe Gly Leu Ser Arg Lys
                645                 650                 655

Ile Tyr Ser Gly Asp Tyr Tyr Arg Gln Gly Cys Ala Ser Lys Leu Pro
            660                 665                 670

Val Lys Trp Leu Ala Leu Glu Ser Leu Ala Asp Asn Leu Tyr Thr Val
        675                 680                 685
```

-continued

```
Gln Ser Asp Val Trp Ala Phe Gly Val Thr Met Trp Glu Ile Met Thr
    690                 695                 700

Arg Gly Gln Thr Pro Tyr Ala Gly Ile Glu Asn Ala Glu Ile Tyr Asn
705                 710                 715                 720

Tyr Leu Ile Gly Gly Asn Arg Leu Lys Gln Pro Pro Glu Cys Met Glu
                725                 730                 735

Asp Val Tyr Asp Leu Met Tyr Gln Cys Trp Ser Ala Asp Pro Lys Gln
            740                 745                 750

Arg Pro Ser Phe Thr Cys Leu Arg Met Glu Leu Glu Asn Ile Leu Gly
        755                 760                 765

Gln Leu Ser Val Leu Ser Ala Ser Gln Asp Pro Leu Tyr Ile Asn Ile
    770                 775                 780

Glu Arg Ala Glu Glu Pro Thr Ala Gly Gly Ser Leu Glu Leu Pro Gly
785                 790                 795                 800

Arg Asp Gln Pro Tyr Ser Gly Ala Gly Asp Gly Ser Gly Met Gly Ala
                805                 810                 815

Val Gly Gly Thr Pro Ser Asp Cys Arg Tyr Ile Leu Thr Pro Gly Gly
            820                 825                 830

Leu Ala Glu Gln Pro Gly Gln Ala Glu His Gln Pro Glu Ser Pro Leu
        835                 840                 845

Asn Glu Thr Gln Arg Leu Leu Leu Leu Gln Gln Gly Leu Leu Pro His
    850                 855                 860

Ser Ser Cys Ala Asp Ala Ser Leu Lys Met Ala Asp Pro Asn Arg Phe
865                 870                 875                 880

Arg Gly Lys Asp Leu Pro Val Leu
                885
```

<210> SEQ ID NO 21
<211> LENGTH: 37
<212> TYPE: DNA
<213> ORGANISM: Homo sapiens

<400> SEQUENCE: 21
gcgaggggag cgcggagccc ggcgcctaca gctcgcc 37

<210> SEQ ID NO 22
<211> LENGTH: 20
<212> TYPE: DNA
<213> ORGANISM: Mus musculus

<400> SEQUENCE: 22
gcccgcgacc tccactgctg 20

<210> SEQ ID NO 23
<211> LENGTH: 18
<212> TYPE: DNA
<213> ORGANISM: Mus musculus

<400> SEQUENCE: 23
ctgtggggag cggcggcg 18

<210> SEQ ID NO 24
<211> LENGTH: 20
<212> TYPE: DNA
<213> ORGANISM: Mus musculus

<400> SEQUENCE: 24
cctgaaccta tggtaactgg 20

-continued

```
<210> SEQ ID NO 25
<211> LENGTH: 17
<212> TYPE: DNA
<213> ORGANISM: Mus musculus

<400> SEQUENCE: 25

acccagtcct ccctacc                                                  17
```